US009977034B2

(12) United States Patent
McCreedy et al.

(10) Patent No.: US 9,977,034 B2
(45) Date of Patent: May 22, 2018

(54) BIOMARKERS FOR FATTY LIVER DISEASE AND METHODS USING THE SAME

(71) Applicants: Metabolon, Inc., Durham, NC (US); The Cleveland Clinic Foundation, Cleveland, OH (US)

(72) Inventors: Bruce J. McCreedy, Raleigh, NC (US); Alvin Berger, Raleigh, NC (US); YunFu Hu, Chapel Hill, NC (US); Satish C. Kalhan, Pepper Pike, OH (US)

(73) Assignees: Meabolon, Inc., Morrisville, NC (US); The Cleveland Clinic Foundation, Cleveland, OH (US)

( * ) Notice: Subject to any disclaimer, the term of this patent is extended or adjusted under 35 U.S.C. 154(b) by 0 days. days.

(21) Appl. No.: 14/843,356

(22) Filed: Sep. 2, 2015

(65) Prior Publication Data

US 2015/0377910 A1 Dec. 31, 2015

Related U.S. Application Data

(63) Continuation of application No. 12/771,729, filed on Apr. 30, 2010, which is a continuation-in-part of application No. PCT/US2008/082013, filed on Oct. 31, 2008.

(60) Provisional application No. 60/984,942, filed on Nov. 2, 2007, provisional application No. 61/042,459, filed on Apr. 4, 2008.

(51) Int. Cl.
*G01N 33/68* (2006.01)
*H01J 49/00* (2006.01)

(52) U.S. Cl.
CPC ...... *G01N 33/6893* (2013.01); *H01J 49/0027* (2013.01); *G01N 2500/00* (2013.01); *G01N 2570/00* (2013.01); *G01N 2800/085* (2013.01); *G01N 2800/52* (2013.01); *G01N 2800/56* (2013.01); *G01N 2800/60* (2013.01); *Y10T 436/143333* (2015.01); *Y10T 436/163333* (2015.01); *Y10T 436/200833* (2015.01)

(58) Field of Classification Search
CPC ........... G01N 33/6893; G01N 2500/00; G01N 2570/00; G01N 2800/085; G01N 2800/52; G01N 2800/56; G01N 2800/28; G01N 2800/60; G01N 33/6846; G01N 33/68; H01J 49/0027; Y10T 436/143333; Y10T 436/163333; Y10T 436/200833
See application file for complete search history.

(56) References Cited

U.S. PATENT DOCUMENTS

| | | | | |
|---|---|---|---|---|
| 6,974,704 B2 * | 12/2005 | Nelson | ................. | C12Q 1/6816 435/7.1 |
| 8,187,830 B2 * | 5/2012 | Hu | ..................... | G01N 33/6893 435/14 |
| 2004/0265889 A1 | 12/2004 | Durham et al. | | |
| 2005/0123628 A1 | 6/2005 | Zabrecky | | |
| 2005/0214883 A1 | 9/2005 | Gong et al. | | |
| 2006/0046980 A1 | 3/2006 | Erion et al. | | |
| 2006/0135420 A1 | 6/2006 | Mato De La Paz et al. | | |
| 2006/0160237 A1 | 7/2006 | Du | | |
| 2007/0184476 A1 | 8/2007 | Hsieh et al. | | |
| 2007/0231811 A1 | 10/2007 | Mato De La Paz et al. | | |
| 2009/0075284 A1 * | 3/2009 | Chinnaiyan | ...... | G01N 33/57434 435/6.12 |
| 2009/0111122 A1 | 4/2009 | Yutaka et al. | | |
| 2009/0111136 A1 | 4/2009 | Murayama | | |
| 2010/0068746 A1 * | 3/2010 | Nakajima | ................. | C12Q 1/26 435/25 |
| 2010/0233724 A1 * | 9/2010 | Watkins | ................. | G01N 33/92 435/7.1 |

FOREIGN PATENT DOCUMENTS

| | | |
|---|---|---|
| EP | 1739431 | 1/2007 |
| JP | 61260896 | 11/1986 |
| JP | 2003139753 | 5/2003 |
| WO | 2006/082522 | 8/2006 |
| WO | 2007/122799 | 1/2007 |
| WO | 2007/116975 | 10/2007 |
| WO | 2007/136674 | 11/2007 |
| WO | 2008/021192 | 2/2008 |

OTHER PUBLICATIONS

Curnow et al., Multiplex Bead Immunoassay Analysis of Aqueous Humor Revels Distinct Cytokine Profiles in Uveitis, Investigative Ophthalmology & Visual Science, Nov. 2005, vol. 46, No. 11, pp. 4251-4259.*

Gottschalk et al., Metabolic Characterization of Patients with Alcohol and Non-Alcoholic Steatohepatitis, Proc. Intl. Soc. Mag. Reson. Med. 15, Mar. 2007.*

Guan et al., A simultaneious liquid chromatography/mass spectrometric assay of glutathione, cysteine, homocysteine and thir disulfides in biological samples, Journal of Pharmaceutical and Biomedical Analysis, 31, 2003, pp. 251-261. (Year: 2003).*

Reed et al., High-performance liquid chromatography analysis of nanomole levies of glutathione, glutathione disulfide and related thiols and disulfides, Analytical Biochemistry, 106, 1980, pp. 55-62. (Year: 1980).*

(Continued)

*Primary Examiner* — Gary Counts

(74) *Attorney, Agent, or Firm* — Brinks Gilson & Lione

(57) ABSTRACT

The present invention provides various biomarkers of fatty liver disease, including steatosis and steatohepatitis. The present invention also provides various methods of using the biomarkers, including methods for diagnosis of fatty liver disease, methods of determining predisposition to fatty liver disease, methods of monitoring progression/regression of fatty liver disease, methods of assessing efficacy of compositions for treating fatty liver disease, methods of screening compositions for activity in modulating biomarkers of fatty liver disease, methods of treating fatty liver disease, as well as other methods based on biomarkers of fatty liver disease.

2 Claims, 13 Drawing Sheets

(56) References Cited

OTHER PUBLICATIONS

International Search Report for International Application No. PCT/US2008/082013, filed Oct. 31, 2008, 4 pages.

Araya, J. et al. "Increase in long-chain polyunsaturated fatty acid n-6/n-3 ratio in relation to hepatic steatosis in patients with non-alcoholic fatty liver disease" Clinical Science, 2004, 106, p. 635-643.

Batt et al., "Manifestations of Chemically Induced Liver Damage," Clin. Chem., vol. 41, No. 12, (1995), pp. 1882-1887.

Biffl et al., "Clinical Significance of Bile Acids, Measured by Radioimmunoassay as an Index of Liver Function, and Development of an Intravenous Stimulation Test, Using an Assay for Sulfolithocholylglycine (SLCG)," Acta Medica Austriaca 1979 AT, vol. 6, No. 4, (1979), pp. 113-120. XP008129771.

Bocharova et al., "Clinical Significance of Determining the Blood Serum Concentration of Glycocholic Acid in Patients with Alcoholic Damage to the Liver," Klinicheskaya Meditsina (Moscow), vol. 70, Nos. 7-8, (1992), pp. 41-44. XP008129769.

Collazos, "Glycocholic Acid in Chronic Active Hepatitis and Mild Liver Diseases," Clinical Investigator, vol. 72, No. 1, (1994), pp. 36-39. XP008129768.

De Paiva et al., "Increased Serum Bile Acids as a Possible Biomarker of Hepatotoxicity in Brazilian Workers Exposed to Solvents in Car Repainting Shops," Biomarkers, vol. 10, No. 6, (Nov.-Dec. 2005), pp. 456-463.

European Examination Report, issued in EP 08845659.5, dated Oct. 14, 2011.

Extended European Search Report, issued in EP 08845659.5, dated Mar. 1, 2011.

Musso et al. "Nitrosative stress predicts the presence and severity of nonalcoholic fatty liver at different stages of the development of insulin resistance and metabolic syndrome: possible role of vitamin A intake" Am J. Clin Nutr., 2007, 86:3, p. 661-671.

Pagani et al., "Determination of Serum Bile Acids in Hepatobiliary Diseases. Clinical Applicability," Minerva Medica, vol. 75, Nos. 3-4, (Jan. 28, 1984), pp. 99-107. XP008129766.

Puri et al., "A Lipidomic Analysis of Nonalcoholic Fatty Liver Diesase," Hepatology, vol. 46, No. 4, (Oct. 1, 2007), pp. 1081-1090. XP002595209.

Neghab et al., "Raised Concentration of Serum Bile Acids Following Occupational Exposure to Halogenated Solvents, 1,1,2-trichloro-1,2-2-trifluoroethane and Trichloroethylene," Int Arch Occup Environ Health, vol. 70, (1997), pp. 187-194.

Sokol et al., "Hepatic Oxidant Injury and Gluthathione Depletion During Total Parenteral Nutrition in Weanling Rats," American Journal of Physiology, vol. 270, No. 4, Part 1, (1996), pp. G691-G700. XP008129767.

Palekar et al. "Clinical model for distinguishing nonalcoholic steatohepatitis from simple steatosis in patients with nonalcoholic fatty liver disease", Liver International (Mar. 1, 2006), vol. 26, No. 2, pp. 151-156.

Bragoszewski et al., "Expression of genes encoding mitochondrial proteins can distinguish nonalcoholic steatosis from steatohepatitis", Acta Biochimica Polonica, (Jan. 1, 2007), vol. 54, No. 2, pp. 341-348.

Paxton et al., "Role of branched-chain 2-oxo acid dehydrogenase and pyruvate dehydrogenase in 2-oxobutyrate metabolism", Biochemical Journal, (Mar. 1, 1986), vol. 234, No. 2, pp. 295-303.

* cited by examiner

RF Importance plot, biomarker compounds that are useful to distinguish control subjects and steatosis subjects.

RF Importance plot biomarker compounds that are useful to distinguish Control subjects from steatohepatitis (NASH) subjects.

RF Importance plot, biomarker compounds that are useful to distinguish healthy (control), steatosis, steatohepatitis (SH) subjects.

RP and ROC of Steatosis (Right) vs Control (Left)

RP and ROC of Steatosis (Right box) vs NASH (Left box)

RP and ROC of Control (Left box) vs Steatohepatitis NASH (Right box)

RP and ROC of NASH (Middle box) vs Steatosis (Right box) vs Control (Left box)

BIOMARKERS FOR FATTY LIVER DISEASE AND METHODS USING THE SAME

RELATED APPLICATIONS

This application is a continuation of U.S. application Ser. No. 12/771,729, filed Apr. 30, 2010, which is a continuation-in-part of PCT Application Serial No. PCT/US2008/082013, filed Oct. 31, 2008, designating the United States and published in English, which claims the benefit of the filing date under 35 U.S.C. § 119(e) of Provisional U.S. Patent Application No. 60/984,942, filed Nov. 2, 2007, and Provisional U.S. Patent Application No. 61/042,459, filed Apr. 4, 2008. All of the foregoing applications are hereby incorporated by reference.

FIELD

The invention generally relates to biomarkers for fatty liver disease and methods based on the same biomarkers.

BACKGROUND

Fatty change in the liver results from excessive accumulation of lipids within hepatocytes. Fatty liver is the accumulation of triglycerides and other fats in the liver cells. Fatty liver disease can range from fatty liver alone (simple fatty liver, steatosis) to fatty liver associated with hepatic inflammation (steatohepatitis). Although having fat in the liver is not normal, by itself it probably causes little harm or permanent damage. Steatosis is generally believed to be a benign condition, with rare progression to chronic liver disease. In contrast, steatohepatitis may progress to liver fibrosis and cirrhosis, can be associated with hepatocellular carcinoma and may result in liver-related morbidity and mortality.

Steatosis can occur with the use of alcohol (alcohol-related fatty liver) or in the absence of alcohol. Steatohepatitis may be related to alcohol-induced hepatic damage or may be unrelated to alcohol. If steatohepatitis is present but a history of alcohol use is not, the condition is termed nonalcoholic steatohepatitis (NASH).

In the absence of alcohol the main risk factors for simple fatty liver and NASH are obesity, diabetes, and high triglyceride levels. In NASH, fat builds up in the liver and eventually causes scar tissue. This type of hepatitis appears to be associated with diabetes, protein malnutrition, obesity, coronary artery disease, and treatment with corticosteroid medications. Fibrosis or cirrhosis in the liver is present in 15-50% of patients with NASH. Approximately 30% of patients with fibrosis develop cirrhosis after 10 years.

Fatty liver disease is now the most common cause for elevated liver function tests in the United States. It is now probably the leading reason for mild elevations of transaminases. Steatosis affects approximately 25-35% of the general population. Non-alcoholic fatty liver disease (including steatosis and steatohepatitis) (NAFLD) is found in over 80% of patients who are obese. NASH affects 2 to 5 percent of Americans and has been detected in 1.2-9% of patients undergoing routine liver biopsy. Over 50% of patients undergoing bariatric surgery have NASH. The disease strikes males and females; early studies report >70% of cases were in females but recent studies report 50% of patients are females. Fatty liver occurs in all age groups. In the United States NASH is the most common liver disease among adolescents and is the third most common cause of chronic liver disease in adults (after hepatitis C and alcohol).

Both NASH and NAFLD are becoming more common, possibly because of the greater number of Americans with obesity. In the past 10 years, the rate of obesity has doubled in adults and tripled in children. Obesity also contributes to diabetes and high blood cholesterol, which can further complicate the health of someone with NASH. Diabetes and high blood cholesterol are also becoming more common among Americans.

NASH is usually a silent disease with few or no symptoms. Patients generally feel well in the early stages and only begin to have symptoms—such as fatigue, weight loss, and weakness—once the disease is more advanced or cirrhosis develops. The progression of NASH can take years, even decades. The process can stop and, in some cases, reverse on its own without specific therapy. Or NASH can slowly worsen, causing scarring or "fibrosis" to appear and accumulate in the liver. As fibrosis worsens, cirrhosis develops; the liver becomes seriously scarred, hardened, and unable to function normally. Not every person with NASH develops cirrhosis, but once serious scarring or cirrhosis is present, few treatments can halt the progression. A person with cirrhosis experiences fluid retention, muscle wasting, bleeding from the intestines, and liver failure. Liver transplantation is the only treatment for advanced cirrhosis with liver failure, and transplantation is increasingly performed in people with NASH. NASH ranks as one of the major causes of cirrhosis in America, behind hepatitis C and alcoholic liver disease.

NASH is usually first suspected in a person who is found to have elevations in liver tests that are included in routine blood test panels, such as alanine aminotransferase (ALT) or aspartate aminotransferase (AST). When further evaluation shows no apparent reason for liver disease (such as medications, viral hepatitis, or excessive use of alcohol) and when x-rays or imaging studies of the liver show fat, NASH is suspected. The only means of proving a diagnosis of NASH and separating it from simple fatty liver is a liver biopsy. A liver biopsy requires a needle to be inserted through the skin and the removal of a small piece of the liver. If the tissue shows fat without inflammation and damage, simple fatty liver is diagnosed. NASH is diagnosed when microscopic examination of the tissue shows fat along with inflammation and damage to liver cells. A biopsy is required to determine whether scar tissue has developed in the liver. Currently, no blood tests or scans can reliably provide this information. Therefore there exists a need for a less invasive diagnostic method (i.e. a method that would not require a biopsy).

SUMMARY

The present invention provides methods of diagnosing whether a subject has steatohepatitis, comprising: analyzing a biological sample from a subject to determine the level(s) of one or more biomarkers for steatohepatitis in the sample, where the one or more biomarkers are selected from Tables 1, 3, 4B, 5B, 6B, 9, 10, 11, 12, 13, and 15 and FIGS. 2, 3, 12, and 13 and comparing the level(s) of the one or more biomarkers in the sample to steatohepatitis-positive and/or steatohepatitis-negative reference levels of the one or more biomarkers in order to diagnose whether the subject has steatohepatitis.

The present invention also provides methods of diagnosing whether a subject has steatosis, comprising: analyzing a biological sample from a subject to determine the level(s) of one or more biomarkers for steatosis in the sample, where the one or more biomarkers are selected from Tables 2, 3, 4B, 5B, 6B, 8, 9, 11, 12, 13, and 15 and FIGS. 1, 3, and 12; and comparing the level(s) of the one or more biomarkers in the sample to steatosis-positive and/or steatosis-negative reference levels of the one or more biomarkers in order to diagnose whether the subject has steatosis.

Also provided are methods of determining whether a subject is predisposed to developing steatohepatitis, comprising: analyzing a biological sample from a subject to determine the level(s) of one or more biomarkers for steatohepatitis in the sample, where the one or more biomarkers are selected from Tables 1, 3, 4B, 6B, 9, 10, 11, 12, 13, and 15 and FIGS. 2, 3, 12 and 13; and comparing the level(s) of the one or more biomarkers in the sample to steatohepatitis-positive and/or steatohepatitis-negative reference levels of the one or more biomarkers in order to determine whether the subject is predisposed to developing steatohepatitis.

The present invention further provides methods of determining whether a subject is predisposed to developing steatosis, comprising: analyzing a biological sample from a subject to determine the level(s) of one or more biomarkers for steatosis in the sample, where the one or more biomarkers are selected from Tables 2, 3, 4B, 5B, 8, 9, 11, 12, 13, and 15 and FIGS. 1, 3, and 12; and comparing the level(s) of the one or more biomarkers in the sample to steatosis-positive and/or steatosis-negative reference levels of the one or more biomarkers in order to determine whether the subject is predisposed to developing steatosis.

In addition, the present invention provides methods of monitoring progression/regression of steatohepatitis in a subject comprising: analyzing a first biological sample from a subject to determine the level(s) of one or more biomarkers for steatohepatitis in the sample, where the one or more biomarkers are selected from Tables 1, 3, 4B, 6B, 9, 10, 11, 12, 13, and 15 and FIGS. 2, 3, 12, and 13 and the first sample is obtained from the subject at a first time point; analyzing a second biological sample from a subject to determine the level(s) of the one or more biomarkers, where the second sample is obtained from the subject at a second time point; and comparing the level(s) of one or more biomarkers in the first sample to the level(s) of the one or more biomarkers in the second sample in order to monitor the progression/regression of steatohepatitis in the subject.

The present invention also provides methods of monitoring progression/regression of steatosis in a subject comprising: analyzing a first biological sample from a subject to determine the level(s) of one or more biomarkers for steatosis in the sample, where the one or more biomarkers are selected from Tables 2, 3, 4B, 5B, 8, 9, 11, 12, 13, and 15 and FIGS. 1, 3, and 12 and the first sample is obtained from the subject at a first time point; analyzing a second biological sample from a subject to determine the level(s) of the one or more biomarkers, wherein the second sample is obtained from the subject at a second time point; and comparing the level(s) of one or more biomarkers in the first sample to the level(s) of the one or more biomarkers in the second sample in order to monitor the progression/regression of steatosis in the subject.

Further provided are methods of assessing the efficacy of a composition for treating steatohepatitis comprising: analyzing, from a subject having steatohepatitis and currently or previously being treated with a composition, a biological sample to determine the level(s) of one or more biomarkers for steatohepatitis selected from Tables 1, 3, 4B, 6B, 9, 10, 11, 12, 13, and 15 and FIGS. 2, 3, 12, and 13; and comparing the level(s) of the one or more biomarkers in the sample to (a) levels of the one or more biomarkers in a previously-taken biological sample from the subject, where the previously-taken biological sample was obtained from the subject before being treated with the composition, (b) steatohepatitis-positive reference levels of the one or more biomarkers, and/or (c) steatohepatitis-negative reference levels of the one or more biomarkers.

The present invention further provides methods for assessing the efficacy of a composition in treating steatohepatitis, comprising: analyzing a first biological sample from a subject to determine the level(s) of one or more biomarkers for steatohepatitis selected from Tables 1, 3, 4B, 6B, 9, 10, 11, 12, 13, and 15 and FIGS. 2, 3, 12, and 13, the first sample obtained from the subject at a first time point; administering the composition to the subject; analyzing a second biological sample from the subject to determine the level(s) of the one or more biomarkers, the second sample obtained from the subject at a second time point after administration of the composition; and comparing the level(s) of one or more biomarkers in the first sample to the level(s) of the one or more biomarkers in the second sample in order to assess the efficacy of the composition for treating steatohepatitis.

The present invention also provides methods of assessing the relative efficacy of two or more compositions for treating steatohepatitis comprising: analyzing, from a first subject having steatohepatitis and currently or previously being treated with a first composition, a first biological sample to determine the level(s) of one or more biomarkers selected from Tables 1, 3, 4B, 6B, 9, 10, 11, 12, 13, and 15 and FIGS. 2, 3, 12, and 13; analyzing, from a second subject having steatohepatitis and currently or previously being treated with a second composition, a second biological sample to determine the level(s) of the one or more biomarkers; and comparing the level(s) of one or more biomarkers in the first sample to the level(s) of the one or more biomarkers in the second sample in order to assess the relative efficacy of the first and second compositions for treating steatohepatitis.

Further, the present invention provides methods for screening a composition for activity in modulating one or more biomarkers of steatohepatitis, comprising: contacting one or more cells with a composition; analyzing at least a portion of the one or more cells or a biological sample associated with the cells to determine the level(s) of one or more biomarkers of steatohepatitis selected from Tables 1, 3, 4B, 6B, 9, 10, 11, 12, 13, and 15 and FIGS. 2, 3, 12, and 13; and comparing the level(s) of the one or more biomarkers with predetermined standard levels for the biomarkers to determine whether the composition modulated the level(s) of the one or more biomarkers.

The present invention further provides methods for identifying a potential drug target for steatohepatitis comprising: identifying one or more biochemical pathways associated with one or more biomarkers for steatohepatitis selected from Tables 1, 3, 4B, 6B, 9, 10, 11, 12, 13, and 15 and FIGS. 2, 3, 12, and 13; and identifying a protein affecting at least one of the one or more identified biochemical pathways, the protein being a potential drug target for steatohepatitis.

The present invention also provides methods for treating a subject having steatohepatitis comprising administering to the subject an effective amount of one or more biomarkers selected from Tables 1, 3, 4B, 6B, 9, 10, 11, 12, 13, and 15 and FIGS. 2, 3, 12 and 13 that are decreased in steatohepatitis.

The present invention also provides methods of distinguishing steatosis from NASH in a subject having steatosis, comprising: analyzing a biological sample from a subject to determine the level(s) of one or more biomarkers for steatosis and/or NASH in the sample, where the one or more biomarkers are selected from Tables 1, 2, 3, 4B, 5B, 6B, 8, 9, 10, 11, 12, 13, and 15 and FIGS. 1, 2, 3, 12, and 13; and comparing the level(s) of the one or more biomarkers in the sample to steatosis-positive reference levels that distinguish over NASH and/or to NASH-positive reference levels that distinguish over steatosis in order to determine whether the subject has NASH.

In addition, the present invention provides methods of diagnosing whether a subject has NASH, comprising: analyzing a biological sample from a subject to determine the level(s) of one or more biomarkers for NASH in the sample, where the one or more biomarkers are selected from Tables 1, 2, 3, 4B, 5B, 6B, 8, 9, 10, 11, 12, 13, and 15 and FIGS. 1, 2, 3, 12, and 13 and comparing the level(s) of the one or more biomarkers in the sample to NASH-positive and/or NASH-negative reference levels of the one or more biomarkers in order to diagnose whether the subject has NASH.

The present invention also provides methods of assessing the efficacy of a composition for treating steatosis comprising: analyzing, from a subject having steatosis and currently or previously being treated with a composition, a biological sample to determine the level(s) of one or more biomarkers for steatosis selected from Tables 2, 3, 4B, 5B, 8, 9, 11, 12, 13, and 15 and FIGS. 1, 3, and 12; and comparing the level(s) of the one or more biomarkers in the sample to (a) levels of the one or more biomarkers in a previously-taken biological sample from the subject, where the previously-taken biological sample was obtained from the subject before being treated with the composition, (b) steatosis-positive reference levels of the one or more biomarkers, and/or (c) steatosis-negative reference levels of the one or more biomarkers.

Also provided are methods of assessing the relative efficacy of two or more compositions for treating steatosis comprising: analyzing, from a first subject having steatosis and currently or previously being treated with a first composition, a first biological sample to determine the level(s) of one or more biomarkers selected from Tables 2, 3, 4B, 5B, 8, 9, 11, 12, 13, and 15 and FIGS. 1, 3, and 12; analyzing, from a second subject having steatosis and currently or previously being treated with a second composition, a second biological sample to determine the level(s) of the one or more biomarkers; and comparing the level(s) of one or more biomarkers in the first sample to the level(s) of the one or more biomarkers in the second sample in order to assess the relative efficacy of the first and second compositions for treating steatosis.

The present invention also provides methods for screening a composition for activity in modulating one or more biomarkers of steatosis, comprising: contacting one or more cells with a composition; analyzing at least a portion of the one or more cells or a biological sample associated with the cells to determine the level(s) of one or more biomarkers of steatosis selected from Tables 2, 3, 4B, 5B, 8, 9, 11, 12, 13, and 15 and FIGS. 1, 3, and 12; and comparing the level(s) of the one or more biomarkers with predetermined standard levels for the biomarkers to determine whether the composition modulated the level(s) of the one or more biomarkers.

Also provided are methods for identifying a potential drug target for steatosis comprising: identifying one or more biochemical pathways associated with one or more biomarkers for steatosis selected from Tables 2, 3, 4B, 5B, 8, 9, 11, 12, 13, and 15 and FIGS. 1, 3, and 12; and identifying a protein affecting at least one of the one or more identified biochemical pathways, the protein being a potential drug target for steatosis.

The present invention also provides methods for treating a subject having steatosis comprising administering to the subject an effective amount of one or more biomarkers selected from Tables 2, 3, 4B, 5B, 8, 9, 11, 12, 13, and 15 and FIGS. 1, 3, and 12 that are decreased in steatosis.

BRIEF DESCRIPTION OF THE DRAWINGS

In FIGS. 10A and 10D, for carnitine and butyrylcarnitine, respectively, $P<0.05$ for NASH vs controls and for steatosis vs controls. In FIGS. 10B and 10C, for propionylcarnitine and 2-methylbutyrylcarnitine, respectively, $P<0.05$ for NASH vs controls, but not significant for steatosis vs controls.

DETAILED DESCRIPTION

Figure 1:
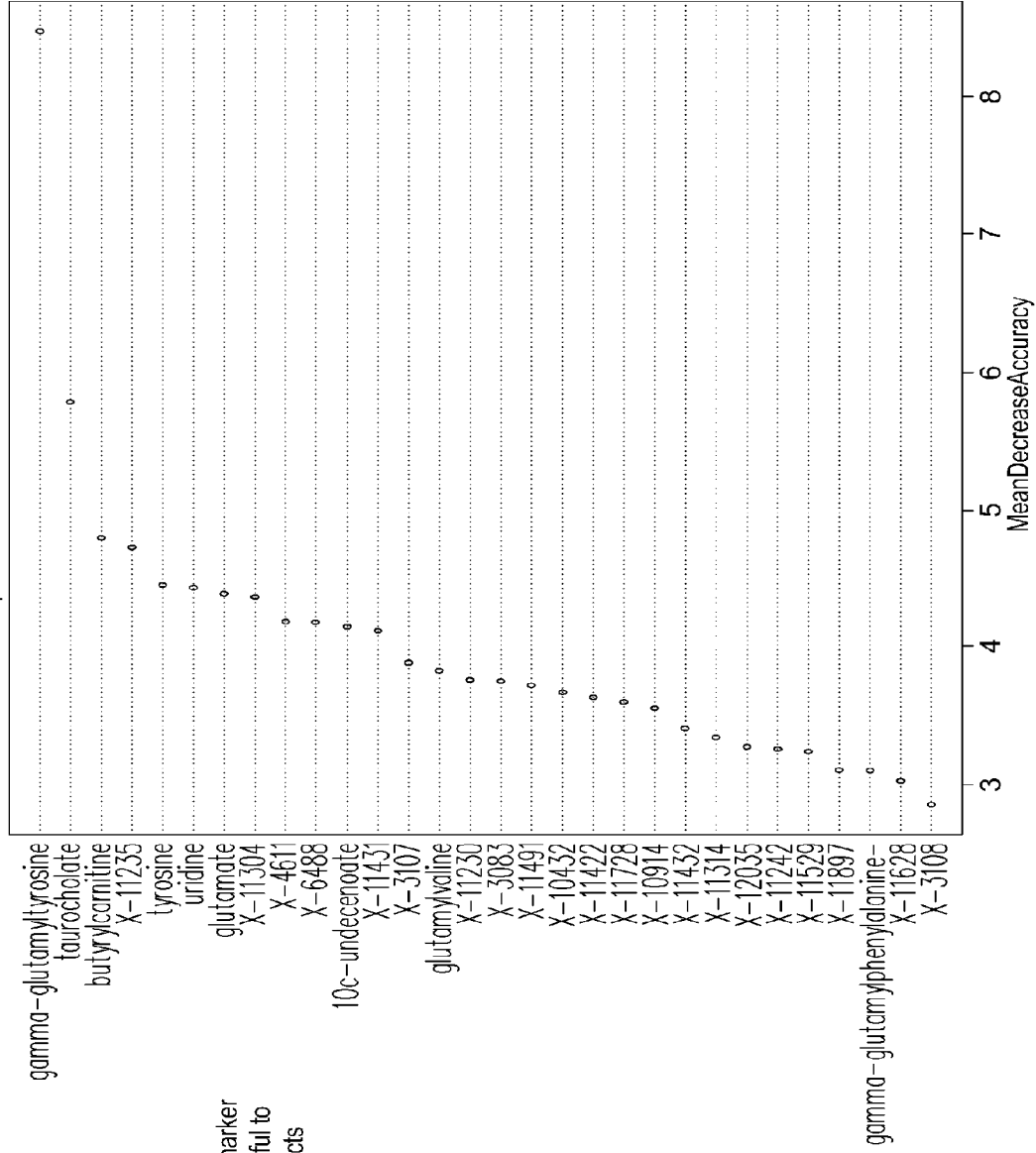
FIG. 1 provides one embodiment of biomarker compounds that are important in distinguishing steatosis subjects and Control subjects.

The present invention relates to biomarkers of steatosis and steatohepatitis, methods for diagnosis (or assisting in the diagnosis) of steatosis and/or steatohepatitis, methods of distinguishing between hepatic steatosis and steatohepatitis, methods of distinguishing between steatosis and NASH, methods of determining predisposition to steatohepatitis, fibrosis and cirrhosis, methods of monitoring progression/regression of steatohepatitis, methods of assessing efficacy of compositions for treating steatohepatitis, methods of screening compositions for activity in modulating biomarkers of steatohepatitis, methods of treating steatohepatitis, as well as other methods based on biomarkers of steatosis and steatohepatitis. Prior to describing this invention in further detail, however, the following terms will first be defined.

Definitions

"Biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (i.e., a p-value less than 0.05 and/or a q-value of less than 0.10 as determined using either Welch's T-test or Wilcoxon's rank-sum Test).

The "level" of one or more biomarkers means the absolute or relative amount or concentration of the biomarker in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, tissue, blood, blood plasma, urine, or cerebral spinal fluid (CSF).

"Subject" means any animal, but is preferably a mammal, such as, for example, a human, monkey, non-human primate, mouse, or rabbit.

A "reference level" of a biomarker means a level of the biomarker that is indicative of a particular disease state, phenotype, or predisposition to developing a particular disease state or phenotype, or lack thereof, as well as combinations of disease states, phenotypes, or predisposition to developing a particular disease state or phenotype, or lack thereof. A "positive" reference level of a biomarker means a level that is indicative of a particular disease state or phenotype. A "negative" reference level of a biomarker means a level that is indicative of a lack of a particular disease state or phenotype. For example, a "NASH-positive reference level" of a biomarker means a level of a biomarker that is indicative of a positive diagnosis of NASH in a subject, and a "NASH-negative reference level" of a biomarker means a level of a biomarker that is indicative of a negative diagnosis of NASH in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched or gender-matched so that comparisons may be made between biomarker levels in samples from subjects of a certain age or gender and reference levels for a particular disease state, phenotype, or lack thereof in a certain age or gender group). Such reference levels may also be tailored to specific techniques that are used to measure levels of biomarkers in biological samples (e.g., LC-MS, GC-MS, etc.), where the levels of biomarkers may differ based on the specific technique that is used.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

"Metabolome" means all of the small molecules present in a given organism.

"Steatosis" refers to fatty liver disease without the presence of inflammation. The condition can occur with the use of alcohol or in the absence of alcohol use.

"Steatohepatitis" refers to fatty liver disease that is associated with inflammation. Steatohepatitis can progress to cirrhosis and can be associated with hepatocellular carcinoma. The condition can occur with the use of alcohol or in the absence of alcohol use.

"Non-alcoholic fatty liver disease" (NAFLD) refers to fatty liver disease (steatosis and steatohepatitis) that occurs in subjects even in the absence of consumption of alcohol in amounts considered harmful to the liver.

"Non-alcoholic steatohepatitis" (NASH) refers to steatohepatitis that occurs in subjects even in the absence of consumption of alcohol in amounts considered harmful to the liver. NASH can progress to cirrhosis and can be associated with hepatocellular carcinoma.

I. Biomarkers

The NAFLD and NASH biomarkers described herein were discovered using metabolomic profiling techniques. Such metabolomic profiling techniques are described in more detail in the Examples set forth below as well as in U.S. Pat. No. 7,005,255 and U.S. patent application Ser. Nos. 11/357,732, 10/695,265 (Publication No. 2005/0014132), Ser. No. 11/301,077 (Publication No. 2006/0134676), Ser. No. 11/301,078 (Publication No. 2006/0134677), Ser. No. 11/301,079 (Publication No. 2006/0134678), and Ser. No. 11/405,033, the entire contents of which are hereby incorporated herein by reference.

Generally, metabolic profiles were determined for biological samples from human subjects diagnosed with steatosis as well as from one or more other groups of human subjects (e.g., healthy control subjects not diagnosed with steatosis), as well as from human subjects diagnosed with NASH. The metabolic profile for biological samples from a subject having steatosis was compared to the metabolic profile for biological samples from the one or more other groups of subjects. Those molecules differentially present, including those molecules differentially present at a level that is statistically significant, in the metabolic profile of samples from subjects with steatosis as compared to another group (e.g., healthy control subjects not diagnosed with steatosis) were identified as biomarkers to distinguish those groups. In addition, those molecules differentially present, including those molecules differentially present at a level that is statistically significant, in the metabolic profile of samples from subjects with steatosis as compared to NASH were also identified as biomarkers to distinguish those groups.

Figure 2:
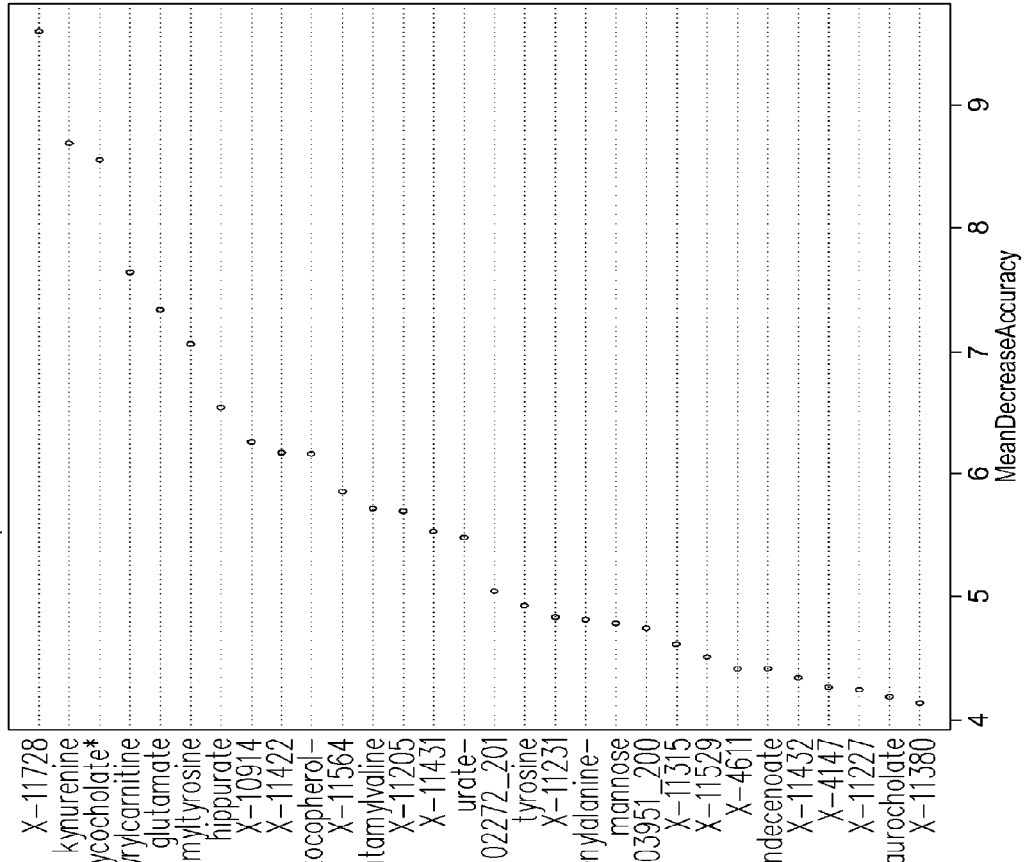
FIG. 2 provides one embodiment of biomarker compounds that are important in distinguishing steatohepatitis subjects from control subjects.
Figure 3:
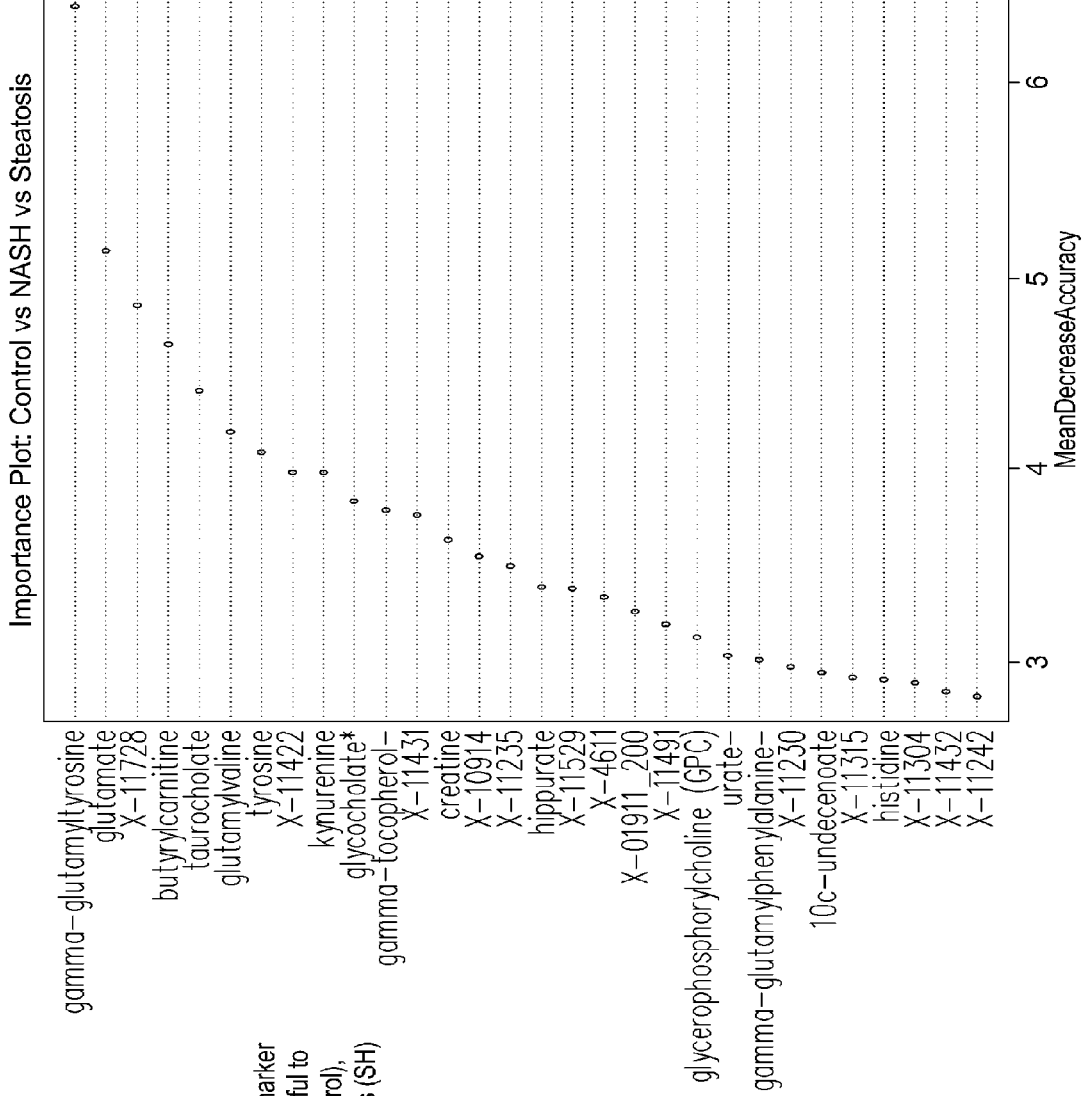
FIG. 3 provides an embodiment of biomarker compounds that are important in distinguishing steatosis, steatohepatitis and control subjects.
Figure 13:
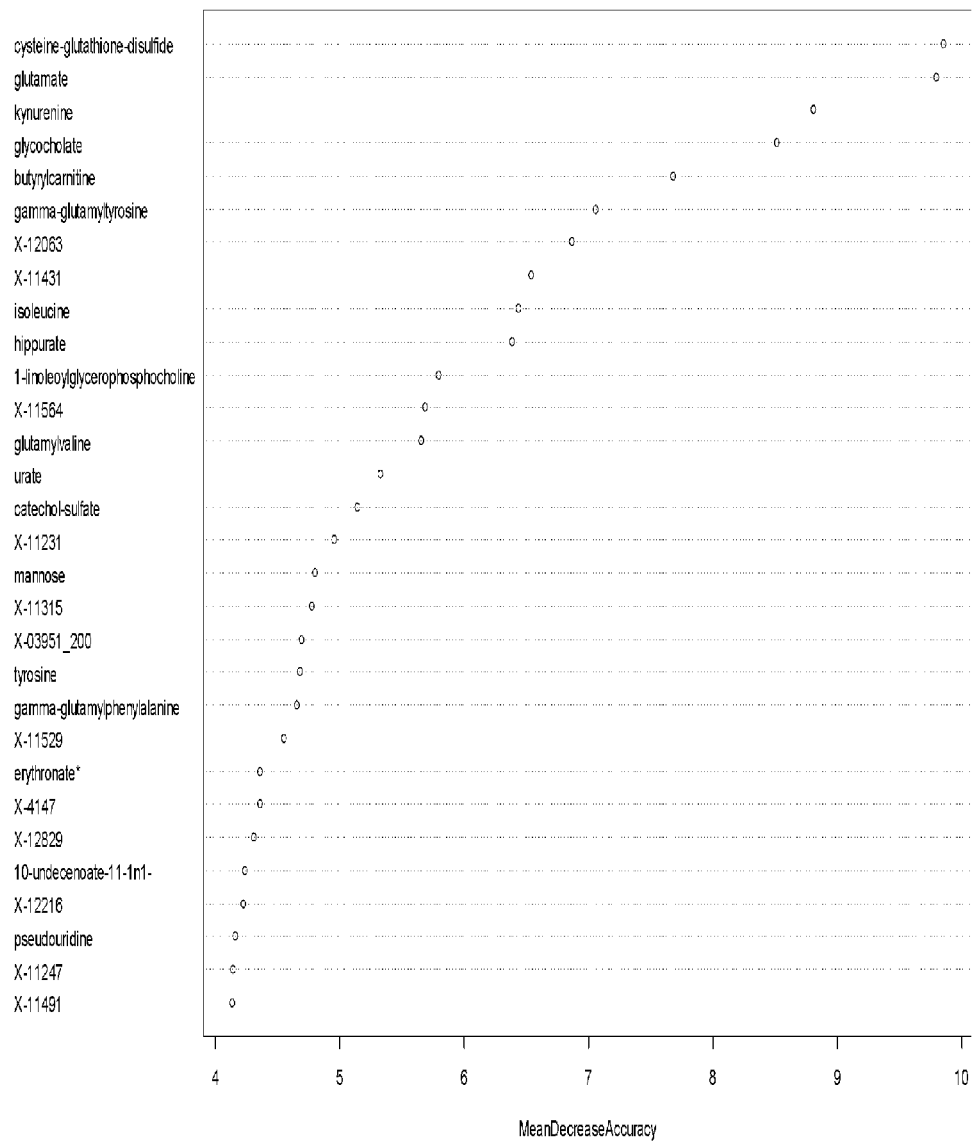
FIG. 13 illustrates a random forest importance plot for controls vs NASH as described in Example 6.

The biomarkers are discussed in more detail herein. The biomarkers that were discovered correspond with the following group(s):

Biomarkers for distinguishing subjects having steatosis vs. control subjects not diagnosed with liver disease (see Tables 2, 4B, 5B, 8, 11, 12, 13, FIG. 1 (gamma-glutamyltyrosine, taurocholate, butyrylcarnitine, Metabolite-11235, Tyrosine, uridine, glutamate, Metabolite-11304, Metabolite-4611, Metabolite-6488, 10c-undecenoate, Metabolite-11431, Metabolite-3107, Glutamylvaline, Metabolite-11230, Metabolite-3083, Metabolite-11491, Metabolite-10432, Metabolite-11422, cysteine-glutathione disulfide (Metabolite-11728), Metabolite-10914, Metabolite-11432, Metabolite-11314, Metabolite-12035, Metabolite-11242, Metabolite-11529, Metabolite-11897, gamma-glutamylphenylalanine-, Metabolite-11628, Metabolite-3108, Alanine, glycocholate, Isobar 47 (taurochenodeoxycholic acid, taurodeoxycholic acid), Isobar 66 (glycochenodeoxycholic acid, glychodeoxycholic acid), Lactate, mannose, Metabolite-10026, Metabolite-10951, Metabolite-2347, Metabolite-2821, Metabolite-3016, Metabolite-3019, Metabolite-3025, Metabolite-3026, Metabolite-3073, Metabolite-3077, Metabolite-3098, Metabolite-3165, Metabolite-3330, Metabolite-4167, Metabolite-4361, Metabolite-4759, Metabolite-4806, Metabolite-5346, Metabolite-5769, Metabolite-8506, Thyroxine, urate), and FIG. 3 (gamma-glutamyltyrosine, glutamate, cysteine-glutathione disulfide (Metabolite-11728), butyrylcarnitine, taurocholate, glutamylvaline tyrosine, Metabolite-11422, kynurenine, glycocholate, gamma-tocopherol, Metabolite-11431, creatine, Metabolite-10914, Metabolite-11235, hippurate, Metabolite-11529, Metabolite-4611, Metabolite-01911, Metabolite-11491, glycerophosphorylcholine (GPC), urate-, gamma-glutamylphenylalanine-, Metabolite-11230, 10c-undecenoate, Metabolite-11315, histidine, Metabolite-11304, Metabolite-11432, Metabolite-11242, alanine, isocitrate, isoleucine, lactate, leucine, mannose, Metabolite-10026, Metabolite-10812, Metabolite-1496, Metabolite-1911, Metabolite-2395, Metabolite-3016, Metabolite-3026, Metabolite-3073, Metabolite-3098, Metabolite-3330, Metabolite-4274, Metabolite-5769, Metabolite-7187, Metabolite-8506, Metabolite-9855, theobromine, thryoxine, urate, valine, xanthine));

Biomarkers for distinguishing subjects having NASH vs. control subjects not diagnosed with liver disease (see Tables 1, 6B, 10, 11, 12, 13, 15, FIGS. 2 and 13 cysteine-glutathione disulfide (Metabolite-11728), Kynurenine, glycocholate, butyrylcarnitine, glutamate, gamma-glutamyltyrosine, hippurate, Metabolite-10914, Metabolite-11422, gamma-tocopherol-, Metabolite-11564, Glutamylvaline, 1-oleoylglycerophosphocholine (Metabolite-11205), Metabolite-11431, urate, Metabolite-02272, Tyrosine, Metabolite-11231, gamma-glutamylphenylalanine, mannose, Metabolite-03951, Metabolite-11315, Metabolite-11529, Metabolite-4611, 10c-undecenoate, Metabolite-11432, Metabolite-4147, Metabolite-11227, Taurocholate, Metabolite-11380, 3-methyl-2-oxobutyric acid, Alanine, glutamine, isocitrate, isoleucine, leucine, meso-erythritol, Metabolite-10026, Metabolite-10812, Metabolite-1086, Metabolite-1110, Metabolite-1335, Metabolite-1496, Metabolite-2041, Metabolite-2272, Metabolite-2395, Metabolite-3073, Metabolite-3087, Metabolite-3098, Metabolite-4274, Metabolite-5769, Metabolite-7187, Valine, xanthine));

Biomarkers for distinguishing subjects having steatohepatitis (NASH) vs. subjects having steatosis (see Tables 3, 4B, 9, 11, 12, 13, and FIG. 3 (gamma-glutamyltyrosine, glutamate, cysteine-glutathione disulfide (Metabolite-11728), butyrylcarnitine, taurocholate, glutamylvaline tyrosine, Metabolite-11422, kynurenine, glycocholate, gamma-tocopherol, Metabolite-11431, creatine, Metabolite-10914, Metabolite-11235, hippurate, Metabolite-11529, Metabolite-4611, Metabolite-01911, Metabolite-11491, glycerophosphorylcholine (GPC), urate-, gamma-glutamylphenylalanine-, Metabolite-11230, 10c-undecenoate, Metabolite-11315, histidine, Metabolite-11304, Metabolite-11432, Metabolite-11242, alanine, isocitrate, isoleucine, lactate, leucine, mannose, Metabolite-10026, Metabolite- 10812, Metabolite-1496, Metabolite-1911, Metabolite-2395, Metabolite-3016, Metabolite-3026, Metabolite-3073, Metabolite-3098, Metabolite-3330, Metabolite-4274, Metabolite-5769, Metabolite-7187, Metabolite-8506, Metabolite-9855, theobromine, thryoxine, urate, valine, xanthine));

Although the identities of some of the biomarkers compounds are not known at this time, such identities are not necessary for the identification of the biomarkers in biological samples from subjects, as the "unnamed" compounds have been sufficiently characterized by analytical techniques to allow such identification. The analytical characterization of all such "unnamed" compounds is listed in the Examples. Such "unnamed" biomarkers are designated herein using the nomenclature "Metabolite" followed by a specific metabolite number.

Any number of biomarkers may be used in the methods disclosed herein. That is, the disclosed methods may include the determination of the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, fifteen or more biomarkers, etc., including a combination of all of the biomarkers in each or all of Tables 1, 2, 3, 4B, 5B, 6B, 8, 9, 11, 12, 13, and 15 and FIG. 1, FIG. 3, FIG. 12, and FIG. 13 or any fraction or combination thereof. In another aspect, the number of biomarkers for use in the disclosed methods include the levels of about thirty or less biomarkers, twenty-five or less, twenty or less, fifteen or less, ten or less, nine or less, eight or less, seven or less, six or less, five or less biomarkers. In another aspect, the number of biomarkers for use in the disclosed methods include the levels of one, two, three, four, five, six, seven, eight, nine, ten, eleven, twelve, thirteen, fourteen, fifteen, twenty, twenty-five, or thirty biomarkers.

In addition, the methods disclosed herein using the biomarkers listed in the tables may be used in combination with clinical diagnostic measures of fatty liver diseases. Combinations with clinical diagnostics may facilitate the disclosed methods, or confirm results of the disclosed methods (for example, facilitating or confirming diagnosis, monitoring progression or regression, and/or determining predisposition to fatty liver diseases).

II. Diagnosis of Steatosis and/or Steatohepatitis

The identification of biomarkers for steatosis allows for the diagnosis of (or for aiding in the diagnosis of) steatosis in subjects presenting one or more symptoms of liver dysfunction. A method of diagnosing (or aiding in diagnosing) whether a subject has steatosis comprises (1) analyzing a biological sample from a subject to determine the level(s) of one or more biomarkers of steatosis in the sample and (2) comparing the level(s) of the one or more biomarkers in the sample to steatosis-positive and/or steatosis-negative reference levels of the one or more biomarkers in order to diagnose (or aid in the diagnosis of) whether the subject has steatosis. The one or more biomarkers that are used are selected from Tables 2, 3, 4B, 5B, 8, 9, 11, 12, 13, FIG. 1, FIG. 3 and combinations thereof. When such a method is used to aid in the diagnosis of steatosis, the results of the method may be used along with other methods (or the results thereof) useful in the clinical determination of whether a subject has steatosis.

In one embodiment for the diagnosis of (or for aiding in the diagnosis of) steatosis, the method comprises (1) analyzing a biological sample from a subject to determine the level(s) of one or more biomarkers of steatosis in the sample and (2) comparing the level(s) of the one or more biomarkers in the sample to steatosis-positive and/or steatosis-negative reference levels of the one or more biomarkers in order to diagnose (or aid in the diagnosis of) whether the subject has steatosis, and the one or more biomarkers that are used are selected from Tables 2, 3, 4B, 5B, 8, 9, 11, 12, 13, FIG. 1, FIG. 3 and combinations thereof.

In an embodiment for the diagnosis of (or for aiding in the diagnosis of) steatohepatitis, the method comprises (1) analyzing a biological sample from a subject to determine the level(s) of one or more biomarkers of steatohepatitis in the sample and (2) comparing the level(s) of the one or more biomarkers in the sample to steatohepatitis-positive and/or steatohepatitis-negative reference levels of the one or more biomarkers in order to diagnose (or aid in the diagnosis of) whether the subject has steatohepatitis, and the one or more biomarkers that are used are selected from Tables 1, 3, 4B, 6B, 9, 10, 11, 12, 13, and 15 and FIG. 2, FIG. 3, FIG. 12, FIG. 13 and combinations thereof.

In an embodiment for the diagnosis of (or for aiding in the diagnosis of) NASH, the method comprises (1) analyzing a biological sample from a subject to determine the level(s) of one or more biomarkers of NASH in the sample and (2) comparing the level(s) of the one or more biomarkers in the sample to NASH-positive and/or NASH-negative reference levels of the one or more biomarkers in order to diagnose (or aid in the diagnosis of) whether the subject has NASH, and the one or more biomarkers that are used are selected from Tables 1, 3, 4B, 6B, 9, 10, 11, 12, 13, and 15 and FIG. 2, FIG. 3, FIG. 12, FIG. 13, and combinations thereof.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzymatic or biochemical reactions, clinical chemistry, enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The levels of one or more of the biomarkers of Tables 1, 2, 3, 4B, 5B, 6B, 8, 9, 10, 11, 12, 13, and 15 and FIG. 1, FIG. 2, FIG. 3, FIG. 12, and FIG. 15 may be determined in the methods of diagnosing and methods of aiding in diagnosing whether a subject has steatosis or steatohepatitis. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Tables 1, 2, 3, 4B, 5B, 6B, 8, 9, 10, 11, 12, 13, and 15 and FIG. 1, FIG. 2, FIG. 3, FIG. 12, and FIG. 13 or any fraction thereof, may be determined and used in such methods. Determining levels of combinations of the biomarkers may allow greater sensitivity and specificity in diagnosing steatosis and aiding in the diagnosis of steatosis, and may allow better differentiation of steatosis from other liver disorders (e.g. fibrosis, cirrhosis, liver cancer, etc.) that may have similar or overlapping biomarkers to steatosis (as compared to a subject not having steatosis). For example, ratios of the levels of certain biomarkers (and non-biomarker compounds) in biological samples may allow greater sensitivity and specificity in diagnosing steatosis and aiding in the diagnosis of steatosis and may allow better differentiation of steatosis from other liver disorders that may have similar or overlapping biomarkers to steatosis (as compared to a subject not having steatosis).

One or more biomarkers that are specific for diagnosing steatosis or steatohepatitis (or aiding in diagnosing steatosis or steatohepatitis) in a certain type of sample (e.g., liver tissue sample, liver biopsy, urine sample, or blood plasma sample) may also be used. For example, when the biological sample is plasma, one or more biomarkers listed in Tables 2, 4B, 5B, 8, 11, 12, 13, FIG. 1, FIG. 3 may be used to diagnose (or aid in diagnosing) whether a subject has steatosis.

After the level(s) of the one or more biomarkers in the sample are determined, the level(s) are compared to steatosis-positive and/or steatosis-negative reference levels (or steatohepatitis-positive and/or steatohepatitis-negative reference levels) to aid in diagnosing or to diagnose whether the subject has steatosis (or steatohepatitis). Levels of the one or more biomarkers in a sample matching the steatosis-positive reference levels (e.g., levels that are the same as the reference levels, substantially the same as the reference levels, above and/or below the minimum and/or maximum of the reference levels, and/or within the range of the reference levels) are indicative of a diagnosis of steatosis in the subject. Levels of the one or more biomarkers in a sample matching the steatosis-negative reference levels (e.g., levels that are the same as the reference levels, substantially the same as the reference levels, above and/or below the minimum and/or maximum of the reference levels, and/or within the range of the reference levels) are indicative of a diagnosis of no steatosis in the subject. In addition, levels of the one or more biomarkers that are differentially present (especially at a level that is statistically significant) in the sample as compared to steatosis-negative reference levels are indicative of a diagnosis of steatosis in the subject. Levels of the one or more biomarkers that are differentially present (especially at a level that is statistically significant) in the sample as compared to steatosis-positive reference levels are indicative of a diagnosis of no steatosis in the subject.

The level(s) of the one or more biomarkers may be compared to steatosis-positive and/or steatosis-negative and/or steatohepatitis-positive and/or steatohepatitis-negative reference levels using various techniques, including a simple comparison (e.g., a manual comparison) of the level(s) of the one or more biomarkers in the biological sample to steatosis-positive and/or steatosis-negative and/or steatohepatitis-positive and/or steatohepatitis-negative reference levels. The level(s) of the one or more biomarkers in the biological sample may also be compared to steatosis-positive and/or steatosis-negative and/or steatohepatitis-positive and/or steatohepatitis-negative reference levels using one or more statistical analyses (e.g., t-test, Welch's T-test, Wilcoxon's rank sum test, ANOVA, recursive partitioning, random forest).

In addition, the biological samples may be analyzed to determine the level(s) of one or more non-biomarker compounds. The level(s) of such non-biomarker compounds may also allow differentiation of steatosis from other liver disorders that may have similar or overlapping biomarkers to steatosis and/or steatohepatitis (as compared to a subject not having a liver disorder). For example, a known non-biomarker compound present in biological samples of subjects having steatosis and subjects not having steatosis could be monitored to verify a diagnosis of steatosis as compared to a diagnosis of another liver disorder when biological samples from subjects having the liver disorder do not have the non-biomarker compound.

The methods of diagnosing (or aiding in diagnosing) whether a subject has steatosis may also be conducted specifically to diagnose (or aid in diagnosing) whether a subject has steatosis and/or steatohepatitis (e.g. NASH). Such methods comprise (1) analyzing a biological sample from a subject to determine the level(s) of one or more biomarkers of steatosis (and/or NASH) in the sample and (2) comparing the level(s) of the one or more biomarkers in the sample to steatosis-positive and/or steatosis-negative reference levels (or NASH-positive and/or NASH-negative reference levels) in order to diagnose (or aid in the diagnosis of) whether the subject has steatosis (or NASH). Biomarker specific for steatosis are listed in Tables 2, 4B, 5B, 8, 11, 12, 13, FIG. 1, FIG. 3 and biomarkers specific for NASH are listed in Tables 1, 4B, 6B, 10, 11, 12, 13, and 15 and FIG. 2, FIG. 3, and FIG. 13.

III. Methods of Distinguishing Steatosis from Steatohepatitis (NASH)

The identification of biomarkers for distinguishing steatosis versus NASH allows steatosis and NASH to be distinguished in patients. A method of distinguishing steatosis from NASH in a subject having NAFLD comprises (1) analyzing a biological sample from a subject to determine the level(s) in the sample of one or more biomarkers of steatosis that distinguish over NASH and/or one or more biomarkers of NASH that distinguish over steatosis, and (2) comparing the level(s) of the one or more biomarkers in the sample to steatosis-positive reference levels that distinguish over NASH and/or NASH-positive reference levels that distinguish over steatosis of the one or more biomarkers in order to determine whether the subject has steatosis or NASH. The one or more biomarkers that may be used include those biomarkers selected from Tables 1, 2, 3, 4B, 5B, 6B, 8, 9, 10, 11, 12, 13, and 15 and FIG. 1, FIG. 2, FIG. 3, FIG. 12, and FIG. 13 and combinations thereof.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzymatic or biochemical reactions, clinical chemistry, enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The levels of one or more of the biomarkers of Tables 1, 2, 3, 4B, 5B, 6B, 8, 9, 10, 11, 12, 13, and 15 and FIG. 1, FIG. 2, FIG. 3, FIG. 12, and FIG. 13 may be determined in the methods of diagnosing and methods of aiding in diagnosing whether a subject has steatohepatitis. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Tables 1, 2, 3, 4B, 5B, 6B, 8, 9, 10, 11, 12, 13, and 15 and FIG. 1, FIG. 2, FIG. 3, FIG. 12, and FIG. 13 or any fraction thereof, may be determined and used in such methods. Determining levels of combinations of the biomarkers may allow greater sensitivity and specificity in distinguishing between steatosis and NASH.

One or more biomarkers that are specific for distinguishing between steatosis and NASH in a certain type of sample (e.g., liver tissue sample, urine sample, or blood plasma sample) may also be used. For example, when the biological sample is blood plasma, one or more biomarkers listed in Tables 1, 2, 3, 4B, 5B, 6B, 8, 9, 10, 11, 12, 13, FIG. 1, FIG. 2, FIG. 3 may be used.

After the level(s) of the one or more biomarkers in the sample are determined, the level(s) are compared to steatosis-positive reference levels that distinguish over NASH-negative and/or NASH-positive reference levels that distinguish over steatosis of the one or more biomarkers in order to determine whether the subject has steatosis or NASH. Levels of the one or more biomarkers in a sample matching the steatosis-positive reference levels that distinguish over NASH (e.g., levels that are the same as the reference levels, substantially the same as the reference levels, above and/or below the minimum and/or maximum of the reference levels, and/or within the range of the reference levels) are indicative of steatosis in the subject. Levels of the one or more biomarkers in a sample matching the NASH-positive reference levels that distinguish over steatosis (e.g., levels that are the same as the reference levels, substantially the same as the reference levels, above and/or below the minimum and/or maximum of the reference levels, and/or within the range of the reference levels) are indicative of NASH in the subject. If the level(s) of the one or more biomarkers are more similar to the steatosis-positive reference levels that distinguish over NASH (or less similar to the NASH-positive reference levels), then the results are indicative of steatosis in the subject. If the level(s) of the one or more biomarkers are more similar to the NASH-positive reference levels that distinguish over steatosis (or less similar to the steatosis-positive reference levels), then the results are indicative of NASH in the subject.

The level(s) of the one or more biomarkers may be compared to steatosis-positive reference levels that distinguish over NASH and/or NASH-positive reference levels that distinguish over steatosis using various techniques, including a simple comparison (e.g., a manual comparison) of the level(s) of the one or more biomarkers in the biological sample to steatosis-positive and/or NASH-positive reference levels. The level(s) of the one or more biomarkers in the biological sample may also be compared to steatosis-positive reference levels that distinguish over NASH and/or NASH-positive reference levels that distinguish over steatosis using one or more statistical analyses (e.g., t-test, Welch's T-test, Wilcoxon's rank sum test, ANOVA, recursive partitioning, random forest).

In addition, the biological samples may be analyzed to determine the level(s) of one or more non-biomarker compounds. The level(s) of such non-biomarker compounds may also allow differentiation of steatosis from NASH.

IV. Methods of Determining Predisposition to Steatohepatitis and/or Steatosis

The identification of biomarkers for steatosis and steatohepatitis also allows for the determination of whether a subject having no symptoms of steatohepatitis or steatosis is predisposed to developing steatohepatitis or steatosis. For example, a method of determining whether a subject having no symptoms of steatohepatitis is predisposed to developing steatohepatitis comprises (1) analyzing a biological sample from a subject to determine the level(s) of one or more biomarkers listed in Tables 1, 3, 4B, 6B, 9, 10, 11, 12, 13, and 15 and FIG. 2, FIG. 3, FIG. 12, and FIG. 13 in the sample and (2) comparing the level(s) of the one or more biomarkers in the sample to steatohepatitis-positive and/or steatohepatitis-negative reference levels of the one or more biomarkers in order to determine whether the subject is predisposed to developing steatohepatitis. The results of the method may be used along with other methods (or the results thereof) useful in the clinical determination of whether a subject is predisposed to developing steatohepatitis.

As described above in connection with methods of diagnosing (or aiding in the diagnosis of) steatohepatitis, any suitable method may be used to analyze the biological sample in order to determine the level(s) of the one or more biomarkers in the sample.

As with the methods of diagnosing (or aiding in the diagnosis of) steatohepatitis or steatosis described above, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers, for example, in Tables 1, 3, 4B, 6B, 9, 10, 11, 12, 13, and 15 and FIG. 2, FIG. 3, FIG. 12, and FIG. 13 or any fraction thereof, may be determined and used in methods of determining whether a subject having no symptoms of steatohepatitis is predisposed to developing steatohepatitis.

After the level(s) of the one or more biomarkers in the sample are determined, the level(s) are compared to, for example, steatohepatitis-positive and/or steatohepatitis-negative reference levels in order to predict whether the subject is predisposed to developing steatohepatitis. Levels of the one or more biomarkers in a sample matching the steatohepatitis-positive reference levels (e.g., levels that are the same as the reference levels, substantially the same as the reference levels, above and/or below the minimum and/or maximum of the reference levels, and/or within the range of the reference levels) are indicative of the subject being predisposed to developing steatohepatitis. Levels of the one or more biomarkers in a sample matching the steatohepatitis-negative reference levels (e.g., levels that are the same as the reference levels, substantially the same as the reference levels, above and/or below the minimum and/or maximum of the reference levels, and/or within the range of the reference levels) are indicative of the subject not being predisposed to developing steatohepatitis. In addition, levels of the one or more biomarkers that are differentially present (especially at a level that is statistically significant) in the sample as compared to steatohepatitis-negative reference levels are indicative of the subject being predisposed to developing steatohepatitis. Levels of the one or more biomarkers that are differentially present (especially at a level that is statistically significant) in the sample as compared to steatohepatitis-positive reference levels are indicative of the subject not being predisposed to developing steatohepatitis.

Furthermore, it may also be possible to determine reference levels specific to assessing whether or not a subject that does not have steatohepatitis is predisposed to developing steatohepatitis. For example, it may be possible to determine reference levels of the biomarkers for assessing different degrees of risk (e.g., low, medium, high) in a subject for developing steatohepatitis. Such reference levels could be used for comparison to the levels of the one or more biomarkers in a biological sample from a subject.

As with the methods described above, the level(s) of the one or more biomarkers may be compared to steatohepatitis-positive and/or steatohepatitis-negative reference levels using various techniques, including a simple comparison, one or more statistical analyses, and combinations thereof.

As with the methods of diagnosing (or aiding in diagnosing) whether a subject has steatohepatitis and/or steatosis, the methods of determining whether a subject having no symptoms of steatohepatitis or steatosis is predisposed to developing steatosis or steatohepatitis may further comprise analyzing the biological sample to determine the level(s) of one or more non-biomarker compounds.

The methods of determining whether a subject having no symptoms of steatohepatitis is predisposed to developing steatohepatitis may also be conducted specifically to determine whether a subject having no symptoms of steatohepatitis is predisposed to developing NASH. Biomarkers specific for steatosis are listed in Tables 2, 4B, 5B, 8, 11, 12, 13, FIG. 1, FIG. 3 and biomarkers specific for NASH are listed in Tables 1, 4B, 6B, 10, 11, 12, 13, and 15 and FIG. 2, FIG. 3, FIG. 12, and FIG. 13.

In addition, methods of determining whether a subject having steatosis is predisposed to developing NASH may be conducted using one or more biomarkers selected from Tables 1, 4B, 6B, 10, 11, 12, 13, and 15 and FIG. 2, FIG. 3, FIG. 12, and FIG. 13.

V. Methods of Monitoring Progression/Regression of Steatosis and/or Steatohepatitis The identification of biomarkers for steatosis and steatohepatitis also allows for monitoring progression/regression of steatosis and/or steatohepatitis in a subject. For example, a method of monitoring the progression/regression of steatosis in a subject comprises (1) analyzing a first biological sample from a subject to determine the level(s) of one or more biomarkers for steatosis selected from Tables 2, 3, 4B, 6B, 8, 9, 11, 12, 13, FIG. 1, FIG. 3, the first sample obtained from the subject at a first time point, (2) analyzing a second biological sample from a subject to determine the level(s) of the one or more biomarkers, the second sample obtained from the subject at a second time point, and (3) comparing the level(s) of one or more biomarkers in the first sample to the level(s) of the one or more biomarkers in the second sample in order to monitor the progression/regression of steatosis in the subject. The results of the method are indicative of the course of steatosis (i.e., progression or regression, if any change) in the subject.

The change (if any) in the level(s) of the one or more biomarkers over time may be indicative of progression or regression of steatosis in the subject. In order to characterize the course of steatosis in the subject, the level(s) of the one or more biomarkers in the first sample, the level(s) of the one or more biomarkers in the second sample, and/or the results of the comparison of the levels of the biomarkers in the first and second samples may be compared to steatosis-positive, steatosis-negative, NAFLD-positive, NAFLD-negative, high-grade steatosis-positive, and/or NASH-negative reference levels as well as steatosis-positive reference levels that distinguish over NASH and/or NASH-positive reference levels that distinguish over steatosis. If the comparisons indicate that the level(s) of the one or more biomarkers are increasing or decreasing over time (e.g., in the second sample as compared to the first sample) to become more similar to the steatosis-positive reference levels (or less similar to the steatosis-negative reference levels), to the NASH reference levels, or, when the subject initially has steatosis, to the NASH-positive reference levels that distinguish over steatosis, then the results are indicative of steatosis progression. If the comparisons indicate that the level(s) of the one or more biomarkers are increasing or decreasing over time to become more similar to the steatosis-negative reference levels (or less similar to the steatosis-positive reference levels), or, when the subject initially has NASH, to steatosis reference levels and/or to steatosis-positive reference levels that distinguish over NASH, then the results are indicative of steatosis regression.

As with the other methods described herein, the comparisons made in the methods of monitoring progression/regression of steatosis in a subject may be carried out using various techniques, including simple comparisons, one or more statistical analyses, and combinations thereof.

The results of the method may be used along with other methods (or the results thereof) useful in the clinical monitoring of progression/regression of steatosis in a subject.

As described above in connection with methods of diagnosing (or aiding in the diagnosis of) steatosis, any suitable method may be used to analyze the biological samples in order to determine the level(s) of the one or more biomarkers in the samples. In addition, the level(s) of one or more biomarkers, including a combination of all of the biomarkers in Tables 2, 4B, 5B, 8, 11, 12, 13, and 15 and FIG. 1, FIG. 3, FIG. 12, and FIG. 13 or any fraction thereof, may be determined and used in methods of monitoring progression/regression of steatosis in a subject.

Such methods could be conducted to monitor the course of steatosis in subjects having steatosis or could be used in subjects not having steatosis (e.g., subjects suspected of being predisposed to developing steatosis) in order to monitor levels of predisposition to steatosis.

Such methods could be conducted to monitor the course of steatohepatitis in subjects having steatohepatitis or could be used in subjects not having steatohepatitis (e.g., subjects suspected of being predisposed to developing steatohepatitis) in order to monitor levels of predisposition to steatohepatitis. The levels(s) of one or more biomarkers, including a combination of all of the biomarkers in Tables 1, 3, 4B, 6B, 9, 10, 11, 12, 13, and 15 and FIGS. 2, 3, 12, and FIG. 13, or any fraction thereof, may be determined and used in methods of monitoring progression/regression of steatohepatitis in a subject.

VI. Methods of Assessing Efficacy of Compositions for Treating Steatohepatitis and/or Steatosis The identification of biomarkers for steatohepatitis and steatosis also allows for assessment of the efficacy of a composition for treating steatohepatitis and/or steatosis as well as the assessment of the relative efficacy of two or more compositions for treating steatohepatitis and/or steatosis. Such assessments may be used, for example, in efficacy studies as well as in lead selection of compositions for treating steatohepatitis or steatosis.

For example, a method of assessing the efficacy of a composition for treating steatohepatitis comprises (1) analyzing, from a subject having steatohepatitis and currently or previously being treated with a composition, a biological sample to determine the level(s) of one or more biomarkers selected from Tables 1, 3, 4B, 6B, 9, 10, 11, 12, 13, and 15 and FIG. 2, FIG. 3, FIG. 12, and FIG. 13, and (2) comparing the level(s) of the one or more biomarkers in the sample to (a) level(s) of the one or more biomarkers in a previously-taken biological sample from the subject, wherein the previously-taken biological sample was obtained from the subject before being treated with the composition, (b) steatohepatitis-positive reference levels (including NASH-positive reference levels) of the one or more biomarkers, (c) steatohepatitis-negative reference levels (including NASH-negative reference levels) of the one or more biomarkers, (d) NASH-positive reference levels that distinguish over steatosis, and/or (e) steatosis-positive reference levels that distinguish over NASH. The results of the comparison are indicative of the efficacy of the composition for treating steatohepatitis.

Thus, in order to characterize the efficacy of the composition for treating steatohepatitis, the level(s) of the one or more biomarkers in the biological sample are compared to (1) steatohepatitis-positive reference levels, (2) steatohepatitis-negative reference levels, (3) previous levels of the one or more biomarkers in the subject before treatment with the composition, (4) NASH-positive reference levels that distinguish over steatosis, and/or (5) steatosis-positive reference levels that distinguish over NASH.

When comparing the level(s) of the one or more biomarkers in the biological sample (from a subject having steatohepatitis and currently or previously being treated with a composition) to steatohepatitis-positive reference levels and/or steatohepatitis-negative reference levels, level(s) in the sample matching the steatohepatitis-negative reference levels (e.g., levels that are the same as the reference levels, substantially the same as the reference levels, above and/or below the minimum and/or maximum of the reference levels, and/or within the range of the reference levels) are indicative of the composition having efficacy for treating steatohepatitis. Levels of the one or more biomarkers in the sample matching the steatohepatitis-positive reference levels (e.g., levels that are the same as the reference levels, substantially the same as the reference levels, above and/or below the minimum and/or maximum of the reference levels, and/or within the range of the reference levels) are indicative of the composition not having efficacy for treating steatohepatitis. The comparisons may also indicate degrees of efficacy for treating steatohepatitis based on the level(s) of the one or more biomarkers.

When comparing the level(s) of the one or more biomarkers in the biological sample (from a subject having NASH and currently or previously being treated with a composition) NASH-positive reference levels that distinguish over steatosis and/or steatosis-positive reference levels that distinguish over NASH, level(s) in the sample matching the NASH-positive reference levels that distinguish over steatosis (e.g., levels that are the same as the reference levels, substantially the same as the reference levels, above and/or below the minimum and/or maximum of the reference levels, and/or within the range of the reference levels) are indicative of the composition having efficacy for treating steatohepatitis. Levels of the one or more biomarkers in the sample matching the NASH-positive reference levels that distinguish over steatosis (e.g., levels that are the same as the reference levels, substantially the same as the reference levels, above and/or below the minimum and/or maximum of the reference levels, and/or within the range of the reference levels) are indicative of the composition not having efficacy for treating steatohepatitis.

When the level(s) of the one or more biomarkers in the biological sample (from a subject having steatohepatitis and currently or previously being treated with a composition) are compared to level(s) of the one or more biomarkers in a previously-taken biological sample from the subject before treatment with the composition, any changes in the level(s) of the one or more biomarkers are indicative of the efficacy of the composition for treating steatohepatitis. That is, if the comparisons indicate that the level(s) of the one or more biomarkers have increased or decreased after treatment with the composition to become more similar to the steatohepatitis-negative reference levels (or less similar to the steatohepatitis-positive reference levels) or, when the subject initially has steatosis, the level(s) have increased or decreased to become more similar to NASH-positive reference levels that distinguish over steatosis (or less similar to the steatosis-positive reference levels that distinguish over NASH), then the results are indicative of the composition having efficacy for treating steatohepatitis. If the comparisons indicate that the level(s) of the one or more biomarkers have not increased or decreased after treatment with the composition to become more similar to the steatohepatitis-negative reference levels (or less similar to the steatohepatitis-positive reference levels) or, when the subject initially has NASH, the level(s) have not increased or decreased to become more similar to steatosis-positive reference levels that distinguish over NASH (or less similar to the NASH-positive reference levels that distinguish over steatosis), then the results are indicative of the composition not having efficacy for treating steatohepatitis. The comparisons may also indicate degrees of efficacy for treating steatohepatitis based on the amount of changes observed in the level(s) of the one or more biomarkers after treatment. In order to help characterize such a comparison, the changes in the level(s) of the one or more biomarkers, the level(s) of the one or more biomarkers before treatment, and/or the level(s) of the one or more biomarkers in the subject currently or previously being treated with the composition may be compared to steatohepatitis-positive reference levels (including low grade and NASH-positive reference levels), steatohepatitis-negative reference levels (including low grade and NASH-negative reference levels), steatosis-positive reference levels that distinguish over NASH, and/or NASH-positive reference levels that distinguish over steatosis.

Another method for assessing the efficacy of a composition in treating steatohepatitis comprises (1) analyzing a first biological sample from a subject to determine the level(s) of one or more biomarkers selected from Tables 1, 3, 4B, 6B, 9, 10, 11, 12, 13, and 15 and FIG. 2, FIG. 3, FIG. 12, and FIG. 13, the first sample obtained from the subject at a first time point, (2) administering the composition to the subject, (3) analyzing a second biological sample from a subject to determine the level(s) of the one or more biomarkers, the second sample obtained from the subject at a second time point after administration of the composition, and (4) comparing the level(s) of one or more biomarkers in the first sample to the level(s) of the one or more biomarkers in the second sample in order to assess the efficacy of the composition for treating steatohepatitis. As indicated above, if the comparison of the samples indicates that the level(s) of the one or more biomarkers have increased or decreased after administration of the composition to become more similar to the steatohepatitis-negative reference levels (or less similar to the steatohepatitis-positive reference levels) or, when the subject initially has NASH, if the level(s) have increased or decreased to become more similar to steatosis-positive reference levels that distinguish over NASH (or less similar to the NASH-positive reference levels that distinguish over steatosis), then the results are indicative of the composition having efficacy for treating steatohepatitis. If the comparisons indicate that the level(s) of the one or more biomarkers have not increased or decreased after treatment with the composition to become more similar to the steatohepatitis-negative reference levels (or less similar to the steatohepatitis-positive reference levels) or, when the subject initially has NASH, the level(s) have not increased or decreased to become more similar to steatosis-positive reference levels that distinguish over NASH (or less similar to the NASH-positive reference levels that distinguish over steatosis), then the results are indicative of the composition not having efficacy for treating steatohepatitis.

The comparison may also indicate a degree of efficacy for treating steatohepatitis based on the amount of changes observed in the level(s) of the one or more biomarkers after administration of the composition as discussed above.

A method of assessing the relative efficacy of two or more compositions for treating steatohepatitis comprises (1) analyzing, from a first subject having steatohepatitis and currently or previously being treated with a first composition, a first biological sample to determine the level(s) of one or more biomarkers selected from Tables 1, 3, 4B, 6B, 9, 10, 11, 12, 13, and 15 and FIG. 2, FIG. 3, FIG. 12, and FIG. 13 (2) analyzing, from a second subject having steatohepatitis and currently or previously being treated with a second composition, a second biological sample to determine the level(s) of the one or more biomarkers, and (3) comparing the level(s) of one or more biomarkers in the first sample to the level(s) of the one or more biomarkers in the second sample in order to assess the relative efficacy of the first and second compositions for treating steatohepatitis. The results are indicative of the relative efficacy of the two compositions, and the results (or the levels of the one or more biomarkers in the first sample and/or the level(s) of the one or more biomarkers in the second sample) may be compared to steatohepatitis-positive reference levels (including low grade and NASH-positive reference levels), steatohepatitis-negative reference levels (including low grade and NASH-negative reference levels), steatosis-positive reference levels that distinguish over NASH, and/or NASH-positive reference levels that distinguish over steatosis to aid in characterizing the relative efficacy.

Each of the methods of assessing efficacy may be conducted on one or more subjects or one or more groups of subjects (e.g., a first group being treated with a first composition and a second group being treated with a second composition).

As with the other methods described herein, the comparisons made in the methods of assessing efficacy (or relative efficacy) of compositions for treating steatohepatitis and/or steatosis may be carried out using various techniques, including simple comparisons, one or more statistical analyses, and combinations thereof. Any suitable method may be used to analyze the biological samples in order to determine the level(s) of the one or more biomarkers in the samples. In addition, the level(s) of one or more biomarkers, including a combination of all of the biomarkers in Tables 1, 3, 4B, 6B, 9, 10, 11, 12, 13, and 15 and FIG. 2, FIG. 3, FIG. 12, and FIG. 13 or any fraction thereof, may be determined and used in methods of assessing efficacy (or relative efficacy) of compositions for treating steatohepatitis.

Finally, the methods of assessing efficacy (or relative efficacy) of one or more compositions for treating steatohepatitis may further comprise analyzing the biological sample to determine the level(s) of one or more non-biomarker compounds. The non-biomarker compounds may then be compared to reference levels of non-biomarker compounds for subjects having (or not having) steatohepatitis.

VII. Methods of Screening a Composition for Activity in Modulating Biomarkers Associated with Steatohepatitis and/or Steatosis The identification of biomarkers for steatohepatitis and steatosis also allows for the screening of compositions for activity in modulating biomarkers associated with steatohepatitis and/or steatosis, which may be useful in treating steatohepatitis and/or steatosis. For example, methods of screening compositions useful for treatment of steatohepatitis comprise assaying test compositions for activity in modulating the levels of one or more biomarkers in Tables 1, 3, 4B, 6B, 9, 10, 11, 12, 13, and 15 and FIG. 2, FIG. 3, FIG. 12, and FIG. 13. Such screening assays may be conducted in vitro and/or in vivo, and may be in any form known in the art useful for assaying modulation of such biomarkers in the presence of a test composition such as, for example, cell culture assays, organ culture assays, and in vivo assays (e.g., assays involving animal models).

In one embodiment, a method for screening a composition for activity in modulating one or more biomarkers of steatohepatitis comprises (1) contacting one or more cells with a composition, (2) analyzing at least a portion of the one or more cells or a biological sample associated with the cells to determine the level(s) of one or more biomarkers of steatohepatitis selected from Tables 1, 3, 4B, 6B, 9, 10, 11, 12, 13, and 15 and FIG. 2, FIG. 3, FIG. 12, and FIG. 13; and (3) comparing the level(s) of the one or more biomarkers with predetermined standard levels for the one or more biomarkers to determine whether the composition modulated the level(s) of the one or more biomarkers. As discussed above, the cells may be contacted with the composition in vitro and/or in vivo. The predetermined standard levels for the one or more biomarkers may be the levels of the one or more biomarkers in the one or more cells in the absence of the composition. The predetermined standard levels for the one or more biomarkers may also be the level(s) of the one or more biomarkers in control cells not contacted with the composition.

In addition, the methods may further comprise analyzing at least a portion of the one or more cells or a biological sample associated with the cells to determine the level(s) of one or more non-biomarker compounds of steatohepatitis and/or steatosis. The levels of the non-biomarker compounds may then be compared to predetermined standard levels of the one or more non-biomarker compounds.

Any suitable method may be used to analyze at least a portion of the one or more cells or a biological sample associated with the cells in order to determine the level(s) of the one or more biomarkers (or levels of non-biomarker compounds). Suitable methods include chromatography (e.g., HPLC, gas chromatograph, liquid chromatography), mass spectrometry (e.g., MS, MS-MS), enzymatic or biochemical reactions, clinical chemistry, ELISA, antibody linkage, other immunochemical techniques, and combinations thereof. Further, the level(s) of the one or more biomarkers (or levels of non-biomarker compounds) may be measured indirectly, for example, by using an assay that measures the level of a compound (or compounds) that correlates with the level of the biomarker(s) (or non-biomarker compounds) that are desired to be measured.

VIII. Method of Identifying Potential Drug Targets

The identification of biomarkers for steatohepatitis and steatosis also allows for the identification of potential drug targets for steatohepatitis and/or steatosis. For example, a method for identifying a potential drug target for steatohepatitis comprises (1) identifying one or more biochemical pathways associated with one or more biomarkers for steatohepatitis selected from Tables 1, 3, 4B, 6B, 9, 10, 11, 12, 13, and 15 and FIG. 2, FIG. 3, FIG. 12, and FIG. 13, and (2) identifying a protein (e.g., an enzyme) affecting at least one of the one or more identified biochemical pathways, the protein being a potential drug target for steatohepatitis.

Another method for identifying a potential drug target for steatohepatitis comprises (1) identifying one or more biochemical pathways associated with one or more biomarkers for steatohepatitis selected from Tables 1, 3, 4B, 6B, 9, 10, 11, 12, 13, and 15 and FIG. 2, FIG. 3, FIG. 12, and FIG. 13, and one or more non-biomarker compounds of steatohepatitis and (2) identifying a protein affecting at least one of the one or more identified biochemical pathways, the protein being a potential drug target for steatohepatitis.

One or more biochemical pathways (e.g., biosynthetic and/or metabolic (catabolic) pathway) are identified that are associated with one or more biomarkers (or non-biomarker compounds). After the biochemical pathways are identified, one or more proteins affecting at least one of the pathways are identified. Preferably, those proteins affecting more than one of the pathways are identified.

A build-up of one metabolite (e.g., a pathway intermediate) may indicate the presence of a 'block' downstream of the metabolite and the block may result in a low/absent level of a downstream metabolite (e.g. product of a biosynthetic pathway). In a similar manner, the absence of a metabolite could indicate the presence of a 'block' in the pathway upstream of the metabolite resulting from inactive or non-functional enzyme(s) or from unavailability of biochemical intermediates that are required substrates to produce the product. Alternatively, an increase in the level of a metabolite could indicate a genetic mutation that produces an aberrant protein which results in the over-production and/or accumulation of a metabolite which then leads to an alteration of other related biochemical pathways and result in dysregulation of the normal flux through the pathway; further, the build-up of the biochemical intermediate metabolite may be toxic or may compromise the production of a necessary intermediate for a related pathway. It is possible that the relationship between pathways is currently unknown and this data could reveal such a relationship.

The proteins identified as potential drug targets may then be used to identify compositions that may be potential candidates for treating steatohepatitis, including compositions for gene therapy.

IX. Methods of Treating Steatohepatitis and/or Steatosis

The identification of biomarkers for steatohepatitis and steatosis also allows for the treatment of steatohepatitis and/or steatosis. For example, in order to treat a subject having steatohepatitis, an effective amount of one or more steatohepatitis biomarkers that are lowered in steatohepatitis as compared to a healthy subject not having steatohepatitis may be administered to the subject. The biomarkers that may be administered may comprise one or more of the biomarkers in Tables 1, 3, 4B, 6B, 9, 10, 11, 12, 13, 15 and FIG. 2, FIG. 3, FIG. 12, and FIG. 13 that are decreased in steatohepatitis. In some embodiments, the biomarkers that are administered are one or more biomarkers listed in Tables 1, 3, 4B, 6B, 9, 10, 11, 12, 13, and 15 and FIG. 2, FIG. 3, FIG. 12, and FIG. 13 that are decreased in steatohepatitis and that have a p-value less than 0.10. In other embodiments, the biomarkers that are administered are one or biomarkers listed in Tables 1, 3, 4B, 6B, 9, 10, 11, 12, 13, and 15 and FIG. 2, FIG. 3, FIG. 12, and FIG. 13 that are decreased in steatohepatitis by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent).

X. Methods of Using the Steatohepatitis and Steatosis Biomarkers for Other Liver Disorders It is believed that some of the biomarkers for steatosis and steatohepatitis described herein may also be biomarkers for liver disorders (e.g. liver fibrosis, cirrhosis, liver cancer, etc.) in general. Therefore, it is believed that at least some of the steatosis biomarkers or steatohepatitis biomarkers may be used in the methods described herein for liver disorders in general. That is, the methods described herein with respect to steatosis and/or steatohepatitis may also be used for diagnosing (or aiding in the diagnosis of) a liver disorder, methods of monitoring progression/regression of a liver disorder, methods of assessing efficacy of compositions for treating a liver disorder, methods of screening a composition for activity in modulating biomarkers associated with a liver disorder, methods of identifying potential drug targets for liver disorder, and methods of treating a liver disorder. Such methods could be conducted as described herein with respect to steatosis.

XI. Other Methods

Other methods of using the biomarkers discussed herein are also contemplated. For example, the methods described in U.S. Pat. No. 7,005,255 and U.S. patent application Ser. No. 10/695,265 may be conducted using a small molecule profile comprising one or more of the biomarkers disclosed herein.

In any of the methods listed herein, the biomarkers that are used may be selected from those biomarkers in Tables 1, 2, 3, 4B, 5B, 6B, 8, 9, 10, 11, 12, 13, and 15 and FIGS. 1, 2, 3, 12, and 13, having p-values of less than 0.05 and/or those biomarkers in Tables 1, 2, 3, 4B, 5B, 6B, 8, 9, 10, 11, 12, 13, and 15 and FIGS. 1, 2, 3, 12, and 13 having q-values of less than 0.10. The biomarkers that are used in any of the methods described herein may also be selected from those biomarkers in Tables 1, 2, 3, 4B, 5B, 6B, 8, 9, 10, 11, 12, 13, and 15 and FIGS. 1, 2, 3, 12, and 13 that are decreased in steatosis and/or steatohepatitis (as compared to the control) or that are decreased in remission (as compared to control or steatosis and/or steatohepatitis) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); and/or those biomarkers in Tables 1, 2, 3, 4B, 5B, 6B, 8, 9, 10, 11, 12, 13, and 15 and FIG. 1, FIG. 2, FIG. 3, FIG. 12, and FIG. 13 that are increased in steatosis and/or steatohepatitis (as compared to the control or remission) or that are increased in remission (as compared to the control or steatosis or steatohepatitis) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more.

EXAMPLES

The invention will be further explained by the following illustrative examples that are intended to be non-limiting.

I. General Methods

A. Identification of Metabolic Profiles for Steatosis and Steatohepatitis

Each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify novel and chemically unnamed compounds.

B. Statistical Analysis

The data was analyzed using statistical tests of significance to identify molecules (either known, named metabolites or unnamed metabolites) present at differential levels in a definable population or subpopulation (e.g., biomarkers for steatosis biological samples compared to control biological samples or compared to patients in remission from steatosis) useful for distinguishing between the definable populations (e.g., steatosis and control, steatohepatitis (NASH) and control, steatosis and NASH). Other molecules (either known, named metabolites or unnamed metabolites) in the definable population or subpopulation were also identified. For significance tests, Analysis of variance (ANOVA), analysis of covariance (ANCOVA) and Wilcoxon signed rank test were used to statistically analyze the data. For classification tests, Random Forest and Recursive Partitioning were used to analyze the data.

C. Biomarker Identification

Various peaks identified in the analyses (e.g. GC-MS, LC-MS, MS-MS), including those identified as statistically significant, were subjected to a mass spectrometry based chemical identification process.

Example 1

Biomarkers were discovered by (1) analyzing blood plasma samples from different groups of human subjects to determine the levels of metabolites in the samples and then (2) statistically analyzing the results to determine those metabolites that were differentially present in the two groups.

The plasma samples used for the analysis were 25 control samples that were from healthy subjects, 11 samples from patients with steatosis and 24 samples from patients with NASH. Subjects for all groups included males and females. After the levels of metabolites were determined, the data was analyzed using significance tests (ANOVA, ANCOVA, Wilcoxon).

ANOVA was used to identify significant differences in the mean levels of metabolites between two populations (i.e., Steatosis vs. Control, NASH vs. Control, Steatosis vs. NASH).

Biomarkers:

As listed below in Tables 1, 2 and 3, biomarkers were discovered that were differentially present between plasma samples from steatosis patients and Control subjects, biomarkers that were discovered that were differentially present between plasma samples from patients with NASH and from Control subjects and biomarkers that were discovered that were differentially present between plasma samples from steatohepatitis (NASH) and plasma samples from subjects with steatosis.

Tables 1, 2 and 3 include, for each listed biomarker, the p-value and q-value determined in the statistical analysis of the data concerning the biomarkers in the steatosis mean level as compared to the control mean level, the NASH mean level as compared to the control mean level, and the steatohepatitis (NASH) mean level as compared to the steatosis mean level. Library indicates the chemical library that was used to identify the compounds. The number 50 refer to the GC library and the numbers 61, 200 and 201 refer to the LC library. Comp ID refers to the identification number for the compound in our internal chemical compound database. The data is presented as a percent change based upon the ratio of means and indicates biomarkers that increase or decrease in NASH relative to control (Table 1), in steatosis relative to control (Table 2) and/or in NASH relative to steatosis (Table 3).

TABLE 1

Biomarkers from subjects with steatohepatitis (NASH) compared to Control subjects

| ID | Biomarker | Library | p-value | q-value | % Change |
|---|---|---|---|---|---|
| 12751 | Metabolite-3073 | 50 | 1.36E−07 | 1.08E−05 | 129% |
| 32322 | glutamate | 50 | 1.52E−07 | 3.11E−05 | 137% |
| 1113 | isocitrate | 61 | 3.94E−07 | 0.000021 | 85% |
| 1125 | isoleucine | 50 | 6.7E−07 | 2.27E−05 | 52% |
| 18706 | Metabolite-5769 | 61 | 7.12E−07 | 2.27E−05 | 64% |
| 33073 | cysteine-glutathione disulfide (Metabolite-11728) | 200 | 1.36E−06 | 0.0001 | −57% |
| 60 | leucine | 50 | 3.12E−06 | 0.0001 | 11% |
| 16511 | Metabolite-4274 | 50 | 3.22E−06 | 0.0001 | 61% |
| 32868 | glycocholate* | 201 | 8.56E−06 | 0.0005 | 331% |
| 32393 | glutamylvaline | 200 | 8.94E−06 | 0.0005 | 33% |
| 1126 | alanine | 50 | 0.000011 | 0.0002 | 40% |
| 1299 | tyrosine | 61 | 1.77E−05 | 0.0003 | 30% |
| 24285 | Metabolite-10026 | 61 | 2.22E−05 | 0.0003 | 52% |
| 2734 | gamma-glutamyltyrosine | 200 | 2.23E−05 | 0.0009 | 29% |
| 15140 | kynurenine | 61 | 2.96E−05 | 0.0004 | 33% |
| 31489 | Metabolite-10914 | 50 | 4.45E−05 | 0.0014 | −45% |
| 1647 | glutamine | 50 | 0.0001 | 0.0007 | 37% |
| 8509 | Metabolite-2041 | 61 | 0.0001 | 0.0008 | 34% |
| 12780 | Metabolite-3098 | 50 | 0.0001 | 0.0007 | 40% |
| 17068 | Metabolite-4627 | 61 | 0.0001 | 0.0009 | 250% |
| 20267 | Metabolite-7187 | 61 | 0.0001 | 0.001 | 85% |
| 32701 | urate- | 200 | 0.0001 | 0.0023 | 22% |
| 33362 | gamma-glutamylphenylalanine- | 200 | 0.0001 | 0.0023 | 29% |
| 33420 | gamma-tocopherol- | 50 | 0.0001 | 0.0023 | 87% |
| 12774 | Metabolite-3094 | 50 | 0.0001 | 0.0023 | 52% |
| 16865 | Metabolite-4522 | 50 | 0.0001 | 0.0011 | 30% |
| 20699 | erythritol | 50 | 0.0001 | 0.0007 | 36% |

TABLE 1-continued

Biomarkers from subjects with steatohepatitis (NASH) compared to Control subjects

| ID | Biomarker | Library | p-value | q-value | % Change |
|---|---|---|---|---|---|
| 30821 | Metabolite-10812 | 50 | 0.0001 | 0.0007 | 21% |
| 2761 | thyroxine | 61 | 0.0002 | 0.0013 | 46% |
| 6847 | Metabolite-1496 | 61 | 0.0002 | 0.0014 | 50% |
| 13600 | Metabolite-3330 | 61 | 0.0002 | 0.0014 | 362% |
| 18882 | Isobar-47-includes-taurochenodeoxycholic acid-and-taurodeoxycholic acid | 61 | 0.0002 | 0.0014 | 268% |
| 32497 | 10c-undecenoate | 201 | 0.0002 | 0.003 | −9% |
| 32675 | Metabolite-03951 | 200 | 0.0002 | 0.003 | 25% |
| 32881 | Metabolite-11564 | 201 | 0.0002 | 0.003 | 33% |
| 584 | Mannose | 50 | 0.0002 | 0.0012 | 29% |
| 1336 | palmitate (16:0) | 50 | 0.0002 | 0.0012 | 10% |
| 16650 | Metabolite-4360 | 50 | 0.0002 | 0.0012 | 213% |
| 5628 | Metabolite-1086 | 61 | 0.0003 | 0.0016 | 105% |
| 24233 | Metabolite-9855 | 61 | 0.0003 | 0.0017 | 146% |
| 18497 | taurocholate | 201 | 0.0003 | 0.0042 | 303% |
| 22570 | Metabolite-9033 | 50 | 0.0003 | 0.0017 | 1% |
| 5687 | Metabolite-1110 | 61 | 0.0004 | 0.0021 | −71% |
| 59 | histidine | 201 | 0.0004 | 0.0042 | −14% |
| 32863 | Metabolite-11546 | 201 | 0.0004 | 0.0042 | 223% |
| 33133 | Metabolite-11788 | 200 | 0.0004 | 0.0042 | 20% |
| 64 | phenylalanine | 61 | 0.0004 | 0.002 | 13% |
| 31595 | Metabolite-10951 | 61 | 0.0005 | 0.0022 | 60% |
| 12783 | Metabolite-3101 | 50 | 0.0005 | 0.0042 | 61% |
| 15990 | glycerophosphorylcholine (GPC) | 200 | 0.0005 | 0.0042 | −28% |
| 17028 | Metabolite-4611 | 50 | 0.0005 | 0.0046 | 35% |
| 32632 | Metabolite-11315 | 200 | 0.0005 | 0.0042 | −32% |
| 12767 | Metabolite-3087 | 50 | 0.0006 | 0.0025 | 46% |
| 12791 | Metabolite-3109 | 50 | 0.0006 | 0.0025 | −28% |
| 32564 | Metabolite-11247 | 201 | 0.0006 | 0.0048 | −67% |
| 32808 | Metabolite-11491 | 201 | 0.0006 | 0.0048 | 130% |
| 527 | lactate | 50 | 0.0006 | 0.0025 | 26% |
| 21047 | 3-methyl-2-oxobutyrate | 61 | 0.0006 | 0.0025 | 10% |
| 7933 | Metabolite-1911 | 61 | 0.0007 | 0.0027 | 112% |
| 31510 | Metabolite-10932 | 61 | 0.0007 | 0.0028 | 34% |
| 32735 | Metabolite-01911 | 200 | 0.0007 | 0.0052 | 99% |
| 1358 | stearate (18:0) | 50 | 0.0008 | 0.0029 | −1% |
| 3147 | xanthine | 61 | 0.0009 | 0.0031 | 91% |
| 27801 | Metabolite-10589 | 61 | 0.0009 | 0.0031 | 64% |
| 1494 | 5-oxoproline | 50 | 0.0009 | 0.0031 | 0% |
| 32552 | Metabolite-11235 | 201 | 0.001 | 0.0065 | 90% |
| 32739 | Metabolite-11422 | 201 | 0.001 | 0.0066 | 31% |
| 599 | pyruvate | 50 | 0.001 | 0.0065 | 44% |
| 25602 | Metabolite-10432 | 50 | 0.001 | 0.0065 | 73% |
| 10551 | Metabolite-2347 | 61 | 0.0011 | 0.0036 | 214% |
| 16016 | Metabolite-3994 | 61 | 0.0011 | 0.0037 | −45% |
| 32846 | Metabolite-11529 | 201 | 0.0011 | 0.0071 | 151% |
| 13296 | Metabolite-3230 | 61 | 0.0013 | 0.004 | 25% |
| 32519 | 1-linoleoylglycerophosphocholine (Metabolite-11205) | 200 | 0.0013 | 0.0077 | −28% |
| 32549 | Metabolite-02269 | 201 | 0.0014 | 0.0077 | −67% |
| 32550 | Metabolite-02272 | 201 | 0.0014 | 0.0077 | −28% |
| 8210 | Metabolite-1981 | 61 | 0.0015 | 0.0048 | −41% |
| 15753 | hippurate | 201 | 0.0016 | 0.0085 | −32% |
| 32656 | Metabolite-11339 | 201 | 0.0017 | 0.0087 | −10% |
| 13214 | Metabolite-3183 | 61 | 0.0018 | 0.0055 | 30% |
| 32544 | Metabolite-11227 | 201 | 0.0019 | 0.0096 | 13% |
| 10286 | Metabolite-2272 | 61 | 0.002 | 0.006 | −26% |
| 22803 | Isobar-66-includes-glycochenodeoxycholic acid-glycodeoxycholic acid | 61 | 0.002 | 0.006 | 195% |
| 10245 | Metabolite-2269- | 61 | 0.0021 | 0.006 | −62% |
| 32548 | Metabolite-11231 | 201 | 0.0022 | 0.0108 | 82% |
| 32559 | Metabolite-11242 | 201 | 0.0022 | 0.0108 | 60% |
| 1110 | arachidonate-20-4-n-6- | 50 | 0.0023 | 0.0064 | 11% |
| 32637 | Metabolite-11320 | 201 | 0.0024 | 0.0115 | −27% |
| 10715 | Metabolite-2395 | 61 | 0.0025 | 0.0068 | 107% |
| 32813 | Metabolite-11496 | 201 | 0.0027 | 0.0122 | −18% |
| 32412 | butyrylcarnitine | 200 | 0.0029 | 0.0129 | 27% |
| 10672 | Metabolite-2390 | 61 | 0.0031 | 0.0084 | 35% |

TABLE 1-continued

Biomarkers from subjects with steatohepatitis (NASH) compared to Control subjects

| ID | Biomarker | Library | p-value | q-value | % Change |
|---|---|---|---|---|---|
| 15529 | Metabolite-3951 | 61 | 0.0034 | 0.009 | 27% |
| 16308 | Metabolite-4147 | 50 | 0.0034 | 0.015 | 43% |
| 32641 | Metabolite-11324 | 201 | 0.0037 | 0.0159 | −25% |
| 32786 | Metabolite-11469 | 200 | 0.0039 | 0.0163 | −68% |
| 32346 | glycochenodeoxycholate | 201 | 0.004 | 0.0165 | 102% |
| 20488 | glucose | 50 | 0.004 | 0.0105 | 18% |
| 607 | urocanate | 200 | 0.0041 | 0.0165 | −20% |
| 7941 | Metabolite-1914 | 61 | 0.0043 | 0.0112 | −69% |
| 32748 | Metabolite-11431 | 201 | 0.0045 | 0.0179 | 73% |
| 21421 | Metabolite-8214 | 50 | 0.0051 | 0.013 | 30% |
| 15122 | glycerol | 50 | 0.0053 | 0.0131 | 18% |
| 15996 | aspartate | 50 | 0.0055 | 0.021 | 40% |
| 18657 | Metabolite-5726 | 61 | 0.0057 | 0.0137 | 65% |
| 32910 | Metabolite-11593 | 201 | 0.0057 | 0.021 | 23% |
| 33131 | Metabolite-11786 | 200 | 0.0057 | 0.021 | −34% |
| 17627 | Metabolite-4986 | 50 | 0.0057 | 0.0137 | −26% |
| 22600 | Metabolite-9043 | 50 | 0.0057 | 0.0137 | 28% |
| 30728 | Metabolite-10797 | 61 | 0.0064 | 0.015 | 72% |
| 32547 | Metabolite-11230 | 201 | 0.0065 | 0.0232 | 70% |
| 32854 | Metabolite-11537 | 200 | 0.0066 | 0.0232 | −47% |
| 32752 | Metabolite-11435 | 201 | 0.0067 | 0.0233 | 68% |
| 12644 | Metabolite-3016 | 50 | 0.0072 | 0.0164 | 14% |
| 18118 | Metabolite-5346 | 50 | 0.0072 | 0.0164 | 31% |
| 27710 | N-acetylglycine | 50 | 0.0076 | 0.017 | −32% |
| 32749 | Metabolite-11432 | 201 | 0.0079 | 0.027 | 71% |
| 18291 | 3-4-5-trimethoxycinnamic acid | 61 | 0.008 | 0.0178 | −64% |
| 19462 | Metabolite-6446 | 50 | 0.0083 | 0.0181 | 24% |
| 3141 | Betaine | 200 | 0.0084 | 0.0283 | −16% |
| 10414 | Metabolite-2291 | 61 | 0.0086 | 0.0186 | −79% |
| 33386 | Metabolite-12035 | 50 | 0.0086 | 0.0284 | 42% |
| 16496 | Metabolite-4251 | 50 | 0.0087 | 0.0186 | 36% |
| 1769 | Cortisone | 201 | 0.0089 | 0.0287 | −22% |
| 15500 | carnitine | 200 | 0.009 | 0.0287 | 10% |
| 18369 | gamma-glutamylleucine | 200 | 0.0093 | 0.0294 | 19% |
| 32848 | Metabolite-11531 | 201 | 0.0095 | 0.0296 | 78% |
| 16518 | Metabolite-4276 | 50 | 0.0098 | 0.0205 | 79% |
| 32545 | Metabolite-11228 | 201 | 0.0099 | 0.0303 | 79% |
| 19323 | docosahexaenoate-DHA- | 50 | 0.0101 | 0.0209 | −27% |
| 19490 | Metabolite-6488 | 50 | 0.0102 | 0.0308 | 54% |
| 32684 | Metabolite-11367 | 201 | 0.0105 | 0.0313 | −37% |
| 27738 | threonate | 50 | 0.0106 | 0.0216 | −25% |
| 1301 | lysine | 50 | 0.0107 | 0.0216 | 12% |
| 33242 | Metabolite-11897 | 201 | 0.011 | 0.0318 | 61% |
| 9905 | Metabolite-2231 | 61 | 0.0112 | 0.0223 | 17% |
| 27288 | Metabolite-10517 | 50 | 0.0114 | 0.0325 | 39% |
| 1431 | p-hydroxyphenyllactate-HPLA- | 50 | 0.0115 | 0.0226 | 34% |
| 25522 | Metabolite-10407 | 50 | 0.0116 | 0.0226 | 25% |
| 32515 | valine* | 200 | 0.0117 | 0.0327 | 10% |
| 22154 | bradykinin | 200 | 0.0118 | 0.0327 | 1226% |
| 32751 | Metabolite-11434 | 201 | 0.0125 | 0.0341 | 33% |
| 10247 | Metabolite-2270 | 61 | 0.0127 | 0.0244 | −68% |
| 19397 | Metabolite-6326 | 50 | 0.0132 | 0.0251 | 24% |
| 15958 | phenylacetate | 201 | 0.0134 | 0.0362 | −23% |
| 15506 | choline | 61 | 0.0138 | 0.026 | −3% |
| 10737 | Isobar-1-includes-mannose-fructose-glucose-galactose-alpha-L-sorbopyranose-Inositol-D-allose-D--altrose-D-psicone-L--gulose-allo-inositol | 61 | 0.014 | 0.026 | 9% |
| 587 | gluconate | 50 | 0.0142 | 0.0261 | 22% |
| 33154 | Metabolite-11809 | 200 | 0.0145 | 0.0387 | −18% |
| 12782 | Metabolite-3100 | 50 | 0.0152 | 0.0276 | 64% |
| 33227 | Metabolite-11882 | 201 | 0.0154 | 0.0406 | −41% |
| 31787 | 3-carboxyl-4-methyl-5-propyl-2-furanpropanoic acid | 201 | 0.017 | 0.0436 | −43% |
| 32197 | 3-(4-hydroxyphenyl)lactate | 201 | 0.0178 | 0.0449 | 25% |
| 9130 | Metabolite-2139 | 61 | 0.0198 | 0.0355 | 26% |
| 33087 | peptide-RPPGFSPF | 200 | 0.0212 | 0.0516 | 818% |
| 32682 | Metabolite-11365 | 201 | 0.0216 | 0.0521 | −17% |
| 32746 | Metabolite-11429 | 201 | 0.0221 | 0.0526 | 18% |
| 16337 | Metabolite-4167 | 61 | 0.0222 | 0.0394 | 32% |

TABLE 1-continued

Biomarkers from subjects with steatohepatitis (NASH) compared to Control subjects

| ID | Biomarker | Library | p-value | q-value | % Change |
|---|---|---|---|---|---|
| 5689 | Metabolite-1111 | 61 | 0.0225 | 0.0395 | 66% |
| 27727 | glutathione, oxidized (GSSG) | 200 | 0.0228 | 0.0536 | −69% |
| 11923 | Metabolite-2821 | 61 | 0.025 | 0.0432 | 21% |
| 14837 | Metabolite-3707 | 61 | 0.0251 | 0.0432 | −39% |
| 13142 | Metabolite-3165 | 61 | 0.0263 | 0.0446 | 14% |
| 32769 | Metabolite-11452 | 201 | 0.0267 | 0.0622 | 51% |
| 606 | uridine | 61 | 0.0274 | 0.0461 | −8% |
| 18591 | Metabolite-5646 | 61 | 0.0278 | 0.0463 | −34% |
| 10087 | Metabolite-2249 | 61 | 0.029 | 0.0477 | 34% |
| 32551 | Metabolite-11234 | 201 | 0.0302 | 0.069 | 26% |
| 33228 | 1-arachidonoylglycerophosphocholine (Metabolite-11883) | 200 | 0.0303 | 0.069 | −24% |
| 12656 | Metabolite-3025 | 50 | 0.0308 | 0.0502 | 13% |
| 22261 | Isobar-60-includes-s-2-hydroxybutyric acid-2-hydroxyisobutyric acid | 61 | 0.0312 | 0.0502 | 55% |
| 32405 | 3-indolepropionate | 200 | 0.0313 | 0.0704 | −36% |
| 10156 | Metabolite-2259 | 61 | 0.0314 | 0.0502 | 73% |
| 7650 | Metabolite-1834 | 61 | 0.0328 | 0.0518 | 47% |
| 32741 | Metabolite-11424 | 200 | 0.0329 | 0.0732 | 15% |
| 32757 | Metabolite-11440 | 201 | 0.0339 | 0.074 | 39% |
| 33012 | Metabolite-11674 | 200 | 0.0339 | 0.074 | 13% |
| 12658 | Metabolite-3026 | 50 | 0.0343 | 0.0537 | 15% |
| 32110 | Metabolite-11086 | 50 | 0.0344 | 0.0742 | −14% |
| 1284 | threonine | 50 | 0.0352 | 0.0546 | −7% |
| 32648 | Metabolite-11331 | 201 | 0.0356 | 0.0758 | −4% |
| 32517 | 1-oleoylglycerophosphocholine (Metabolite-11203) | 200 | 0.0359 | 0.0758 | −17% |
| 10092 | Metabolite-2250 | 61 | 0.0363 | 0.0557 | 55% |
| 63 | cholesterol | 50 | 0.0373 | 0.0561 | 12% |
| 1507 | palmitoleate | 50 | 0.0376 | 0.0561 | 28% |
| 12768 | Metabolite-3088 | 50 | 0.0376 | 0.0561 | −18% |
| 32578 | Metabolite-11261 | 200 | 0.0389 | 0.0806 | 26% |
| 8796 | Metabolite-2074 | 61 | 0.0391 | 0.0578 | 90% |
| 33140 | Metabolite-11795 | 200 | 0.04 | 0.082 | 24% |
| 21127 | 1-palmitoylglycerol-1-monopalmitin- | 50 | 0.0424 | 0.0621 | 13% |
| 27256 | Metabolite-10500 | 50 | 0.0432 | 0.0871 | 15% |
| 13024 | Metabolite-3139 | 61 | 0.0433 | 0.0628 | 33% |
| 32599 | Metabolite-11282 | 201 | 0.0434 | 0.0871 | 39% |
| 30633 | Metabolite-10785 | 61 | 0.044 | 0.0633 | −22% |
| 9491 | Metabolite-2185 | 61 | 0.0445 | 0.0634 | 25% |
| 32880 | Metabolite-11563 | 201 | 0.0449 | 0.0893 | −16% |
| 594 | nicotinamide | 61 | 0.045 | 0.0636 | −13% |
| 12663 | Metabolite-3030 | 50 | 0.0457 | 0.0638 | −11% |
| 30281 | Metabolite-10743 | 50 | 0.047 | 0.0644 | −17% |
| 17390 | Metabolite-4806 | 50 | 0.0478 | 0.0644 | 21% |
| 12790 | Metabolite-3108 | 50 | 0.048 | 0.0946 | 24% |
| 19370 | Metabolite-6268 | 50 | 0.048 | 0.0644 | 4% |
| 6413 | Metabolite-1342 | 61 | 0.0481 | 0.0644 | −13% |
| 18015 | Metabolite-3113 | 61 | 0.0487 | 0.0644 | −15% |
| 17033 | Metabolite-4613 | 61 | 0.049 | 0.0644 | 53% |
| 12645 | Metabolite-3017 | 50 | 0.0499 | 0.0644 | −13% |
| 17304 | Metabolite-4759 | 61 | 0.0502 | 0.0644 | 26% |
| 22895 | Metabolite-9299 | 50 | 0.0503 | 0.0644 | −9% |
| 12647 | Metabolite-3019 | 50 | 0.0513 | 0.0646 | 12% |
| 16045 | Metabolite-4006 | 50 | 0.0513 | 0.0646 | 26% |
| 24077 | Metabolite-9727 | 50 | 0.0519 | 0.0647 | 19% |
| 27275 | Metabolite-10507 | 50 | 0.0527 | 0.0653 | −11% |
| 32315 | serine | 50 | 0.0532 | 0.1028 | −15% |
| 31401 | Metabolite-10892 | 50 | 0.0543 | 0.1029 | 36% |
| 32452 | propionylcarnitine | 200 | 0.055 | 0.1029 | 18% |
| 21631 | Metabolite-8403 | 50 | 0.0552 | 0.1029 | 19% |
| 32348 | 2-aminobutyrate | 200 | 0.0561 | 0.1036 | −13% |
| 16019 | Metabolite-3995 | 61 | 0.0584 | 0.0716 | −24% |
| 32776 | 2-methylbutyrylcarnitine (Metabolite-11459) | 200 | 0.0584 | 0.1065 | 19% |
| 10629 | Metabolite-2386 | 61 | 0.0587 | 0.0716 | 26% |
| 1572 | Glycerate | 50 | 0.0588 | 0.1065 | −16% |
| 12035 | pelargonate-9-0- | 50 | 0.0592 | 0.0716 | −1% |
| 31529 | Metabolite-10941 | 61 | 0.0597 | 0.0717 | 18% |

TABLE 1-continued

Biomarkers from subjects with steatohepatitis (NASH) compared to Control subjects

| ID | Biomarker | Library | p-value | q-value | % Change |
|---|---|---|---|---|---|
| 32762 | Metabolite-11445 | 201 | 0.06 | 0.1078 | -55% |
| 32691 | Metabolite-11374 | 200 | 0.0607 | 0.108 | 19% |
| 528 | alpha-keto-glutarate | 61 | 0.0625 | 0.0744 | 28% |
| 32792 | Metabolite-11475 | 201 | 0.0631 | 0.1115 | 54% |
| 32572 | Metabolite-11255 | 200 | 0.0644 | 0.112 | -51% |
| 6398 | Metabolite-1335 | 61 | 0.0645 | 0.0763 | 41% |
| 27718 | creatine | 200 | 0.0652 | 0.112 | 17% |
| 16666 | Metabolite-4365 | 50 | 0.0656 | 0.112 | -22% |
| 18335 | quinate | 50 | 0.0656 | 0.112 | -52% |
| 12666 | Metabolite-3033 | 50 | 0.0683 | 0.08 | -11% |
| 1366 | trans-4-hydroxyproline | 50 | 0.0699 | 0.0809 | 35% |
| 32385 | Metabolite-11180 | 50 | 0.0702 | 0.1172 | -10% |
| 18477 | glycodeoxycholate | 201 | 0.0704 | 0.1172 | 247% |
| 10501 | Metabolite-2321 | 61 | 0.0709 | 0.0815 | -25% |
| 32328 | hexanoylcarnitine | 200 | 0.0713 | 0.1177 | 17% |
| 22133 | DL-hexanoyl-carnitine | 61 | 0.0719 | 0.082 | 28% |
| 32596 | Metabolite-02250 | 200 | 0.0722 | 0.1178 | 36% |
| 32740 | Metabolite-11423 | 201 | 0.0725 | 0.1178 | 13% |
| 12785 | Metabolite-3103 | 50 | 0.0743 | 0.1195 | 42% |
| 32697 | Metabolite-11380 | 200 | 0.0747 | 0.1195 | 13% |
| 13557 | Metabolite-3323 | 61 | 0.0779 | 0.0883 | 71% |
| 32761 | Metabolite-11444 | 201 | 0.0805 | 0.1278 | 31% |
| 32952 | Metabolite-02277 | 201 | 0.0819 | 0.1286 | -75% |
| 32945 | Metabolite-11628 | 201 | 0.0822 | 0.1286 | 38% |
| 32338 | glycine | 50 | 0.084 | 0.1292 | -15% |
| 1712 | hydrocortisone | 201 | 0.0854 | 0.1292 | -19% |
| 21418 | Isobar-56-includes-DL-pipecolic acid-1-amino-1-cyclopentanecarboxylic acid | 61 | 0.0856 | 0.0958 | -24% |
| 1105 | linoleate | 50 | 0.0858 | 0.0958 | 11% |
| 32638 | Metabolite-11321 | 201 | 0.0867 | 0.1296 | -12% |
| 12919 | Metabolite-3130 | 61 | 0.0889 | 0.0978 | 67% |
| 33203 | Metabolite-11858 | 201 | 0.0893 | 0.1321 | -63% |
| 33366 | Metabolite-12020 | 200 | 0.0896 | 0.1321 | -27% |
| 22842 | cholate | 201 | 0.0996 | 0.144 | 125% |
| 32814 | Metabolite-11497 | 201 | 0.1001 | 0.144 | -7% |
| 32743 | bradykinin, hydroxyproline form- | 200 | 0.1007 | 0.144 | 158% |
| 32671 | Metabolite-11354 | 200 | 0.1009 | 0.144 | -13% |
| 25459 | Metabolite-10395 | 50 | 0.1012 | 0.144 | -14% |
| 12067 | undecanoate | 201 | 0.1035 | 0.1452 | -5% |
| 18868 | Metabolite-5847 | 50 | 0.1035 | 0.1452 | 70% |
| 21762 | Metabolite-8506 | 61 | 0.1759 | 0.1569 | -16% |

TABLE 2

Biomarkers from subjects with Steatosis compared to Control subjects.

| ID | Biomarker | Library | p-value | q-value | % Change |
|---|---|---|---|---|---|
| 18706 | Metabolite-5769 | 61 | 2.09E-06 | 0.0004 | 80% |
| 12644 | Metabolite-3016 | 50 | 2.08E-05 | 0.0021 | 30% |
| 12751 | Metabolite-3073 | 50 | 0.0001 | 0.0043 | 102% |
| 24285 | Metabolite-10026 | 61 | 0.0001 | 0.0031 | 64% |
| 1125 | isoleucine | 50 | 0.0002 | 0.0076 | 48% |
| 18882 | Isobar-47-includes-taurochenodeoxycholic acid-and-taurodeoxycholic acid | 61 | 0.0003 | 0.0076 | 309% |
| 18476 | glycocholate | 61 | 0.0004 | 0.0092 | 248% |
| 32322 | glutamate | 50 | 0.0005 | 0.0384 | -91% |
| 32497 | 10c-undecenoate | 201 | 0.0005 | 0.0384 | 11% |
| 31489 | Metabolite-10914 | 50 | 0.0006 | 0.0384 | 47% |
| 33073 | cysteine-glutathione disulfide (Metabolite-11728) | 200 | 0.0006 | 0.0384 | 53% |
| 12658 | Metabolite-3026 | 50 | 0.0007 | 0.0136 | 30% |
| 33386 | Metabolite-12035 | 50 | 0.0007 | 0.0384 | -80% |
| 584 | mannose | 50 | 0.001 | 0.0177 | -25% |
| 1299 | tyrosine | 200 | 0.0011 | 0.0499 | -27% |
| 17068 | Metabolite-4627 | 61 | 0.0012 | 0.0203 | 263% |
| 12780 | Metabolite-3098 | 50 | 0.0015 | 0.0208 | 34% |
| 60 | leucine | 50 | 0.0015 | 0.0208 | -13% |
| 18118 | Metabolite-5346 | 50 | 0.0016 | 0.0208 | 42% |

TABLE 2-continued

Biomarkers from subjects with Steatosis compared to Control subjects.

| ID | Biomarker | Library | p-value | q-value | % Change |
|---|---|---|---|---|---|
| 32393 | glutamylvaline | 200 | 0.0016 | 0.0577 | −28% |
| 2734 | gamma-glutamyltyrosine | 200 | 0.0018 | 0.0577 | −24% |
| 11923 | Metabolite-2821 | 61 | 0.0019 | 0.0227 | 38% |
| 27801 | Metabolite-10589 | 61 | 0.002 | 0.0231 | 80% |
| 32846 | Metabolite-11529 | 201 | 0.002 | 0.0577 | −172% |
| 32701 | urate- | 200 | 0.0021 | 0.0577 | −23% |
| 10672 | Metabolite-2390 | 61 | 0.0023 | 0.0245 | 57% |
| 1649 | valine | 50 | 0.0024 | 0.0247 | 37% |
| 32749 | Metabolite-11432 | 201 | 0.003 | 0.0722 | −106% |
| 13142 | Metabolite-3165 | 61 | 0.0031 | 0.029 | 25% |
| 7650 | Metabolite-1834 | 61 | 0.0035 | 0.029 | 144% |
| 10715 | Metabolite-2395 | 61 | 0.0035 | 0.029 | 661% |
| 10551 | Metabolite-2347 | 61 | 0.0036 | 0.029 | 154% |
| 22133 | DL-hexanoyl-carnitine | 61 | 0.0036 | 0.029 | 317% |
| 59 | histidine | 201 | 0.0036 | 0.0804 | 14% |
| 16337 | Metabolite-4167 | 61 | 0.0038 | 0.029 | 66% |
| 22803 | Isobar-66-includes-glycochenodeoxycholic acid-glycodeoxycholic acid | 61 | 0.0039 | 0.029 | 194% |
| 10737 | Isobar-1-includes-mannose-fructose-glucose-galactose-alpha-L-sorbopyranose-Inositol-D-allose-D--altrose-D-psicone-L--gulose-allo-inositol | 61 | 0.004 | 0.029 | 13% |
| 25602 | Metabolite-10432 | 50 | 0.0044 | 0.0867 | −62% |
| 12770 | Metabolite-3090 | 50 | 0.0045 | 0.0867 | −67% |
| 9491 | Metabolite-2185 | 61 | 0.0048 | 0.0338 | 50% |
| 606 | uridine | 201 | 0.0049 | 0.0882 | 22% |
| 12656 | Metabolite-3025 | 50 | 0.0052 | 0.0354 | 22% |
| 32776 | 2-methylbutyrylcarnitine (Metabolite-11459) | 200 | 0.006 | 0.0975 | −40% |
| 21047 | 3-methyl-2-oxobutyric acid | 61 | 0.0062 | 0.0409 | 20% |
| 32748 | Metabolite-11431 | 201 | 0.0062 | 0.0975 | −82% |
| 32641 | Metabolite-11324 | 201 | 0.0065 | 0.0975 | 29% |
| 18369 | gamma-glutamylleucine | 61 | 0.0065 | 0.0414 | −18% |
| 22600 | Metabolite-9043 | 50 | 0.0068 | 0.0414 | −51% |
| 1126 | alanine | 50 | 0.0071 | 0.0414 | 26% |
| 32412 | butyrylcarnitine | 200 | 0.0073 | 0.1038 | −38% |
| 16511 | Metabolite-4274 | 50 | 0.0089 | 0.0489 | 39% |
| 17304 | Metabolite-4759 | 61 | 0.0094 | 0.0503 | 48% |
| 17028 | Metabolite-4611 | 50 | 0.0095 | 0.1279 | −31% |
| 32548 | Metabolite-11231 | 201 | 0.0102 | 0.1281 | −75% |
| 13214 | Metabolite-3183 | 61 | 0.0109 | 0.0524 | 28% |
| 30821 | Metabolite-10812 | 50 | 0.0112 | 0.0524 | −20% |
| 16016 | Metabolite-3994 | 61 | 0.0113 | 0.0524 | −45% |
| 21762 | Metabolite-8506 | 61 | 0.0118 | 0.0536 | 50% |
| 33362 | gamma-glutamylphenylalanine- | 200 | 0.0122 | 0.1281 | −23% |
| 9130 | Metabolite-2139 | 61 | 0.0126 | 0.0557 | 40% |
| 13600 | Metabolite-3330 | 61 | 0.013 | 0.0557 | 139% |
| 31401 | Metabolite-10892 | 50 | 0.0132 | 0.1281 | −64% |
| 32552 | Metabolite-11235 | 201 | 0.0134 | 0.1281 | −53% |
| 64 | phenylalanine | 61 | 0.0134 | 0.0557 | −9% |
| 32564 | Metabolite-11247 | 201 | 0.0135 | 0.1281 | 62% |
| 19490 | Metabolite-6488 | 50 | 0.0139 | 0.1281 | −47% |
| 32578 | Metabolite-11261 | 200 | 0.0144 | 0.1281 | −54% |
| 16308 | Metabolite-4147 | 50 | 0.0145 | 0.1281 | −48% |
| 32754 | Metabolite-11437 | 201 | 0.0148 | 0.1281 | 50% |
| 32547 | Metabolite-11230 | 201 | 0.0151 | 0.1281 | −83% |
| 32808 | Metabolite-11491 | 201 | 0.0154 | 0.1281 | −86% |
| 12783 | Metabolite-3101 | 50 | 0.0158 | 0.1281 | −39% |
| 1769 | cortisone | 201 | 0.0162 | 0.1281 | 28% |
| 32945 | Metabolite-11628 | 201 | 0.0179 | 0.1339 | −68% |
| 2761 | thyroxine | 61 | 0.018 | 0.0734 | 31% |
| 12647 | Metabolite-3019 | 50 | 0.0184 | 0.0734 | 17% |
| 12763 | Metabolite-3083 | 50 | 0.0186 | 0.1339 | −36% |
| 32881 | Metabolite-11564 | 201 | 0.0186 | 0.1339 | −26% |
| 15500 | carnitine | 200 | 0.0189 | 0.1339 | −11% |
| 16865 | Metabolite-4522 | 50 | 0.0192 | 0.075 | 22% |
| 1494 | 5-oxoproline | 50 | 0.0197 | 0.075 | 20% |
| 30805 | Metabolite-10810 | 50 | 0.0198 | 0.1349 | −75% |
| 32753 | Metabolite-09789 | 201 | 0.0201 | 0.1349 | 51% |
| 1642 | caprate-10-0- | 201 | 0.0219 | 0.1425 | 7% |
| 32854 | Metabolite-11537 | 200 | 0.0223 | 0.1425 | 46% |
| 32863 | Metabolite-11546 | 201 | 0.0257 | 0.1608 | −116% |

TABLE 2-continued

Biomarkers from subjects with Steatosis compared to Control subjects.

| ID | Biomarker | Library | p-value | q-value | % Change |
|---|---|---|---|---|---|
| 9905 | Metabolite-2231 | 61 | 0.0262 | 0.0921 | 18% |
| 12790 | Metabolite-3108 | 50 | 0.0276 | 0.1669 | −26% |
| 527 | lactate | 50 | 0.0276 | 0.0952 | −20% |
| 32926 | Metabolite-11609 | 201 | 0.028 | 0.1669 | −44% |
| 8509 | Metabolite-2041 | 61 | 0.0298 | 0.0996 | 22% |
| 8210 | Metabolite-1981 | 61 | 0.0309 | 0.1016 | −35% |
| 32519 | 1-linoleoylglycerophosphocholine (Metabolite-11205) | 200 | 0.0312 | 0.1764 | 22% |
| 32813 | Metabolite-11496 | 201 | 0.0347 | 0.1875 | 16% |
| 32698 | Metabolite-11381__200 | 200 | 0.036 | 0.1875 | −22% |
| 32631 | Metabolite-11314 | 200 | 0.0365 | 0.1875 | −11% |
| 32517 | 1-oleoylglycerophosphocholine (Metabolite-11203) | 200 | 0.037 | 0.1875 | 26% |
| 32807 | Metabolite-11490 | 201 | 0.04 | 0.1972 | −125% |
| 18497 | taurocholate | 201 | 0.0404 | 0.1972 | −115% |
| 15140 | L-kynurenine | 61 | 0.0407 | 0.1275 | 24% |
| 12782 | Metabolite-3100 | 50 | 0.0422 | 0.1978 | −49% |
| 27727 | glutathione, oxidized (GSSG) | 200 | 0.0426 | 0.1978 | 72% |
| 32621 | Metabolite-11304 | 200 | 0.0427 | 0.1978 | −43% |
| 13557 | Metabolite-3323 | 61 | 0.0447 | 0.135 | 68% |
| 31595 | Metabolite-10951 | 61 | 0.0451 | 0.135 | 27% |
| 20699 | erythritol | 50 | 0.0452 | 0.2057 | −23% |
| 32878 | Metabolite-11561 | 201 | 0.0477 | 0.2137 | −32% |
| 1113 | isocitrate | 61 | 0.0497 | 0.144 | 34% |
| 32910 | Metabolite-11593 | 201 | 0.0507 | 0.2233 | −20% |
| 17390 | Metabolite-4806 | 50 | 0.0519 | 0.1462 | 27% |
| 32752 | Metabolite-11435 | 201 | 0.0533 | 0.2263 | −41% |
| 1647 | glutamine | 50 | 0.0534 | 0.147 | 21% |
| 33242 | Metabolite-11897 | 201 | 0.0544 | 0.2263 | −38% |
| 32452 | propionylcarnitine | 200 | 0.0545 | 0.2263 | −27% |
| 32978 | Metabolite-11656 | 200 | 0.0547 | 0.2263 | 6% |
| 27710 | N-acetylglycine | 50 | 0.0581 | 0.155 | −29% |
| 12785 | Metabolite-3103 | 50 | 0.0581 | 0.2331 | −48% |
| 33228 | 1-arachidonoylglycerophosphocholine (Metabolite-11883) | 200 | 0.0581 | 0.2331 | 18% |
| 1336 | palmitate | 50 | 0.0586 | 0.155 | 14% |
| 594 | nicotinamide | 200 | 0.0598 | 0.2337 | 16% |
| 15996 | aspartate | 50 | 0.0606 | 0.2337 | −29% |
| 10245 | Metabolite-2269- | 61 | 0.0622 | 0.1602 | −42% |
| 33131 | Metabolite-11786 | 200 | 0.0626 | 0.2367 | 33% |
| 32559 | Metabolite-11242 | 201 | 0.0641 | 0.2372 | −27% |
| 15529 | Metabolite-3951 | 61 | 0.0658 | 0.1647 | 22% |
| 5687 | Metabolite-1110 | 61 | 0.0702 | 0.1672 | −43% |
| 19370 | Metabolite-6268 | 50 | 0.0707 | 0.1672 | 25% |
| 32549 | Metabolite-02269 | 201 | 0.0733 | 0.2653 | 44% |
| 12789 | Metabolite-3107 | 50 | 0.0741 | 0.2653 | −59% |
| 528 | alpha-keto-glutarate | 61 | 0.0742 | 0.1717 | −27% |
| 31510 | Metabolite-10932 | 61 | 0.0764 | 0.1746 | 21% |
| 19985 | Metabolite-6957 | 50 | 0.0799 | 0.2678 | −20% |
| 10247 | Metabolite-2270 | 61 | 0.0802 | 0.1773 | −64% |
| 18868 | Metabolite-5847 | 50 | 0.0804 | 0.2678 | −67% |
| 32675 | Metabolite-03951__200 | 200 | 0.0812 | 0.2678 | −15% |
| 20488 | glucose | 50 | 0.0819 | 0.1773 | 11% |
| 18335 | quinate | 50 | 0.0822 | 0.2678 | 20% |
| 15676 | 3-methyl-2-oxovalerate | 201 | 0.0827 | 0.2678 | −17% |
| 25601 | Metabolite-10431 | 50 | 0.0828 | 0.2678 | −41% |
| 12593 | Metabolite-2973 | 50 | 0.0852 | 0.2678 | −22% |
| 32838 | Metabolite-11521 | 200 | 0.0856 | 0.2678 | −35% |
| 19397 | Metabolite-6326 | 50 | 0.086 | 0.1815 | 19% |
| 31787 | 3-carboxyl-4-methyl-5-propyl-2-furanpropanoic acid | 201 | 0.0861 | 0.2678 | 53% |
| 12604 | Metabolite-2981 | 50 | 0.0864 | 0.2678 | −15% |
| 21631 | Metabolite-8403 | 50 | 0.0885 | 0.2678 | −26% |
| 1515 | salicylic acid | 50 | 0.0887 | 0.2678 | −140% |
| 1301 | lysine | 200 | 0.09 | 0.2687 | −14% |
| 32511 | EDTA* | 201 | 0.0942 | 0.2759 | −7% |
| 32971 | Metabolite-11654 | 200 | 0.0945 | 0.2759 | −36% |
| 12767 | Metabolite-3087 | 50 | 0.096 | 0.1954 | 35% |
| 32795 | Metabolite-11478 | 201 | 0.0982 | 0.2796 | −35% |
| 32793 | Metabolite-11476 | 200 | 0.0988 | 0.2796 | 6% |

TABLE 3

Biomarkers from subjects with Steatosis compared to Steatohepatitis subjects.

| ID | Biomarker | Library | p-value | q-value | % Change |
|---|---|---|---|---|---|
| 21762 | Metabolite-8506 | 61 | 0.0006 | 0.1449 | −44% |
| 528 | alpha-keto-glutarate | 61 | 0.0017 | 0.1921 | 75% |
| 6847 | Metabolite-1496 | 61 | 0.0025 | 0.1921 | 49% |
| 16650 | Metabolite-4360 | 50 | 0.0033 | 0.1921 | −144% |
| 18591 | Metabolite-5646 | 61 | 0.0041 | 0.1921 | −53% |
| 27718 | creatine | 200 | 0.0071 | 1 | −50% |
| 599 | pyruvate | 61 | 0.0087 | 0.253 | −42% |
| 32621 | Metabolite-11304 | 200 | 0.0124 | 1 | 31% |
| 1113 | isocitrate | 61 | 0.0151 | 0.3249 | 38% |
| 15506 | choline | 61 | 0.0163 | 0.3249 | −28% |
| 32729 | Metabolite-11412 | 200 | 0.0166 | 1 | −14% |
| 10501 | Metabolite-2321 | 61 | 0.0183 | 0.3249 | −40% |
| 12644 | Metabolite-3016 | 50 | 0.0186 | 0.3249 | −13% |
| 32735 | Metabolite-01911 | 200 | 0.0199 | 1 | −99% |
| 15753 | hippurate | 201 | 0.0255 | 1 | 44% |
| 30805 | Metabolite-10810 | 50 | 0.0302 | 1 | 37% |
| 12768 | Metabolite-3088 | 50 | 0.0305 | 0.4178 | −25% |
| 10629 | Metabolite-2386 | 61 | 0.0335 | 0.4178 | 25% |
| 33209 | Metabolite-11864 | 201 | 0.0376 | 1 | 45% |
| 32855 | Metabolite-11538 | 201 | 0.0429 | 1 | 34% |
| 32416 | alpha linolenate (18:3(n-3)) | 201 | 0.0486 | 1 | 32% |
| 16518 | Metabolite-4276 | 50 | 0.0499 | 0.481 | 63% |
| 20267 | Metabolite-7187 | 61 | 0.0521 | 0.481 | 37% |
| 19462 | Metabolite-6446 | 50 | 0.0552 | 0.481 | 22% |
| 33420 | gamma-tocopherol- | 50 | 0.0556 | 1 | −54% |
| 1515 | salicylic acid | 50 | 0.0569 | 1 | 60% |
| 32567 | Metabolite-11250 | 200 | 0.0573 | 1 | 40% |
| 32769 | Metabolite-11452 | 201 | 0.0608 | 1 | −79% |
| 12774 | Metabolite-3094 | 50 | 0.0625 | 1 | −24% |
| 32632 | Metabolite-11315 | 200 | 0.0651 | 1 | 21% |
| 32741 | Metabolite-11424 | 200 | 0.0655 | 1 | −13% |
| 12658 | Metabolite-3026 | 50 | 0.0658 | 0.525 | −12% |
| 32110 | Metabolite-11086 | 50 | 0.0659 | 1 | 17% |
| 30728 | Metabolite-10797 | 61 | 0.0693 | 0.525 | 65% |
| 32625 | Metabolite-11308 | 201 | 0.0697 | 1 | 27% |
| 15140 | kynurenine | 200 | 0.0702 | 1 | −14% |
| 12645 | Metabolite-3017 | 50 | 0.0709 | 0.525 | −22% |
| 33154 | Metabolite-11809 | 200 | 0.0711 | 1 | 19% |
| 12067 | undecanoate | 201 | 0.072 | 1 | 6% |
| 5628 | Metabolite-1086 | 61 | 0.0723 | 0.525 | 45% |
| 19402 | Metabolite-6346 | 50 | 0.077 | 1 | −20% |
| 32631 | Metabolite-11314 | 200 | 0.0779 | 1 | 8% |
| 7933 | Metabolite-1911 | 61 | 0.0792 | 0.5308 | 75% |
| 32797 | Metabolite-11480 | 201 | 0.0818 | 1 | −213% |
| 18254 | paraxanthine | 200 | 0.0824 | 1 | −69% |
| 32912 | Metabolite-11595 | 201 | 0.0834 | 1 | 25% |
| 32717 | Metabolite-11400 | 200 | 0.0855 | 1 | 39% |
| 33133 | Metabolite-11788 | 200 | 0.0862 | 1 | −11% |
| 22261 | Isobar-60-includes-s-2-hydroxybutyric acid-2-hydroxyisobutyric acid | 61 | 0.0869 | 0.5308 | 42% |
| 19374 | Metabolite-6270 | 50 | 0.09 | 1 | 27% |
| 6398 | Metabolite-1335 | 61 | 0.0908 | 0.5308 | 28% |
| 12770 | Metabolite-3090 | 50 | 0.0919 | 1 | 28% |

TABLE 3-continued

Biomarkers from subjects with Steatosis compared to Steatohepatitis subjects.

| ID | Biomarker | Library | p-value | q-value | % Change |
|---|---|---|---|---|---|
| 18392 | theobromine | 200 | 0.0956 | 1 | −118% |
| 32978 | Metabolite-11656 | 200 | 0.0961 | 1 | −6% |
| 32761 | Metabolite-11444 | 201 | 0.0962 | 1 | −11% |
| 31548 | peptide-DSGEGDFXAEGGGVR | 200 | 0.0981 | 1 | −323% |
| 3141 | betaine | 200 | 0.0986 | 1 | 14% |
| 606 | uridine | 201 | 0.0987 | 1 | −17% |
| 24233 | Metabolite-9855 | 61 | 0.0996 | 0.5308 | 99% |

Example 2 Random Forest Classification of Subjects

Random forest analyses were used for classification of samples into groups (e.g. disease or healthy, steatosis or healthy, steatohepatitis or healthy, steatosis or NASH). Random forests give an estimate of how well we can classify individuals in a new data set into each group, in contrast to a t-test, which tests whether the unknown means for two populations are different or not. Random forests create a set of classification trees based on continual sampling of the experimental units and compounds. Then each observation is classified based on the majority votes from all the classification trees.

Random forest results show that the samples can be classified correctly with varying degrees of accuracy using the biomarkers listed in Tables 1, 2, and/or 3. The confusion matrices demonstrate that using plasma samples steatosis subjects, steatohepatitis subjects and control subjects can be distinguished (Table 4), steatosis subjects can be distinguished from control subjects (Table 5), steatohepatitis subjects can be distinguished from control subjects (Table 6) and steatosis subjects can be distinguished from steatohepatitis subjects (Table 7). The "Out-of-Bag" (OOB) Error rate gives an estimate of how accurately new observations can be predicted using the random forest model (e.g., whether a sample is from a subject having steatosis or a control subject).

TABLE 4

Confusion Matrix showing Control subjects, Steatosis subjects and NASH subjects can be distinguished from each other.
Confusion Matrix: Control vs. Steatosis vs. NASH

| | Control_Predicted | Steatosis_Predicted | NASH_Predicted | Error |
|---|---|---|---|---|
| Control | 23 | 0 | 2 | 8% |
| Steatosis | 3 | 9 | 12 | 63% |
| NASH | 2 | 4 | 5 | 55% |
| Out_of_bag_error | | | 38% | |

Based on the OOB Error rate of 38%, the Random Forest model that was created could be used to predict whether a subject has steatosis, steatohepatitis, or no fatty liver disease with about 62% accuracy from analysis of the levels of the biomarkers in samples from the subject. The biomarkers that are the most important biomarkers for distinguishing the groups are listed in Table 4B and displayed in FIG. 3.

TABLE 4B

Most important biomarkers to distinguish control, steatosis and steatohepatitis subjects from Random Forest Importance Plot shown in FIG. 3.

| ID | Biomarker |
|---|---|
| 2734 | gamma-glutamyltyrosine |
| 32322 | glutamate |
| 33073 | cysteine-glutathione disulfide (Metabolite-11728) |
| 32412 | butyrylcarnitine |
| 18497 | taurocholate |
| 32393 | glutamylvaline |
| 1299 | tyrosine |
| 32739 | Metabolite-11422 |
| 15140 | kynurenine |
| 32868 | glycocholate* |
| 33420 | gamma-tocopherol- |
| 32748 | Metabolite-11431 |
| 27718 | creatine |
| 31489 | Metabolite-10914 |
| 32552 | Metabolite-11235 |
| 15753 | hippurate |
| 32846 | Metabolite-11529 |
| 17028 | Metabolite-4611 |
| 32735 | Metabolite-01911__200 |
| 32808 | Metabolite-11491 |
| 15990 | glycerophosphorylcholine (GPC) |
| 32701 | urate- |
| 33362 | gamma-glutamylphenylalanine- |
| 32547 | Metabolite-11230 |
| 32497 | 10c-undecenoate |
| 32632 | Metabolite-11315 |
| 59 | histidine |
| 32621 | Metabolite-11304 |
| 32749 | Metabolite-11432 |
| 32559 | Metabolite-11242 |
| 1126 | alanine |
| 1113 | isocitrate |
| 1125 | isoleucine |
| 527 | lactate |
| 60 | leucine |
| 584 | mannose |
| 24285 | Metabolite-10026 |
| 30821 | Metabolite-10812 |
| 6847 | Metabolite-1496 |
| 7933 | Metabolite-1911 |
| 10715 | Metabolite-2395 |
| 12644 | Metabolite-3016 |
| 12658 | Metabolite-3026 |
| 12751 | Metabolite-3073 |
| 12780 | Metabolite-3098 |
| 13600 | Metabolite-3330 |
| 16511 | Metabolite-4274 |
| 18706 | Metabolite-5769 |
| 20267 | Metabolite-7187 |
| 21762 | Metabolite-8506 |
| 24233 | Metabolite-9855 |
| 18392 | theobromine |
| 2761 | thryoxine |
| 1604 | urate |
| 1649 | valine |
| 3147 | xanthine |

TABLE 5

Confusion Matrix showing Control subjects can be distinguished from Steatosis subjects.
Confusion Matrix: Control vs. Steatosis

| | Control_Predicted | Steatosis_Predicted | Error |
|---|---|---|---|
| Control | 22 | 3 | 12% |
| Steatosis | 1 | 10 | 9% |
| Out_of_bag_error | | 11% | |

Based on the OOB Error rate of 11%, the Random Forest model that was created could be used to predict whether a subject has steatosis or no fatty liver disease with about 89% accuracy from analysis of the levels of the biomarkers in samples from the subject. The biomarkers that are the most important biomarkers for distinguishing the groups are listed in Table 5B and displayed in FIG. 1.

TABLE 5 B

Most important biomarkers from Random Forest Importance Plot shown in FIG. 1.

| ID | Biomarker |
|---|---|
| 2734 | gamma-glutamyltyrosine |
| 18497 | taurocholate |
| 32412 | butyrylcarnitine |
| 32552 | Metabolite-11235 |
| 1299 | tyrosine |
| 606 | uridine |
| 32322 | glutamate |
| 32621 | Metabolite-11304 |
| 17028 | Metabolite-4611 |
| 19490 | Metabolite-6488 |
| 32497 | 10c-undecenoate |
| 32748 | Metabolite-11431 |
| 12789 | Metabolite-3107 |
| 32393 | glutamylvaline |
| 32547 | Metabolite-11230 |
| 12763 | Metabolite-3083 |
| 32808 | Metabolite-11491 |
| 25602 | Metabolite-10432 |
| 32739 | Metabolite-11422 |
| 33073 | cysteine-glutathione disulfide (Metabolite-11728) |
| 31489 | Metabolite-10914 |
| 32749 | Metabolite-11432 |
| 32631 | Metabolite-11314 |
| 33386 | Metabolite-12035 |
| 32559 | Metabolite-11242 |
| 32846 | Metabolite-11529 |
| 33242 | Metabolite-11897 |
| 33362 | gamma-glutamylphenylalanine- |
| 32945 | Metabolite-11628 |
| 12790 | Metabolite-3108 |
| 1126 | alanine |
| 18476 | glycocholate |
| | Isobar 47 (taurochenodeoxycholic acid, taurodeoxycholic acid) |
| | Isobar 66 (glycochenodeoxycholic acid, glychodeoxycholic acid) |
| 57 | lactate |
| 584 | mannose |
| 24285 | Metabolite-10026 |
| 31595 | Metabolite-10951 |
| 10551 | Metabolite-2347 |
| 11923 | Metabolite-2821 |
| 12644 | Metabolite-3016 |
| 12647 | Metabolite-3019 |
| 12656 | Metabolite-3025 |
| 12658 | Metabolite-3026 |
| 12751 | Metabolite-3073 |
| | Metabolite-3077 |
| 12780 | Metabolite-3098 |
| 13142 | Metabolite-3165 |
| 13600 | Metabolite-3330 |
| 16337 | Metabolite-4167 |
| | Metabolite-4361 |
| 17304 | Metabolite-4759 |

TABLE 5 B-continued

Most important biomarkers from Random Forest Importance Plot shown in FIG. 1.

| ID | Biomarker |
|---|---|
| 17390 | Metabolite-4806 |
| 18118 | Metabolite-5346 |
| 18706 | Metabolite-5769 |
| 21762 | Metabolite-8506 |
| 2761 | thyroxine |
| 1604 | urate |

TABLE 6

Confusion Matrix showing Control subjects can be distinguished from NASH subjects.
Confusion Matrix: Control vs. NASH

| | Control_Predicted | NASH_Predicted | Error |
|---|---|---|---|
| Control | 23 | 2 | 8% |
| NASH | 2 | 22 | 8% |
| Out_of_bag_error | | 8% | |

Based on the OOB Error rate of 8%, the Random Forest model that was created could be used to predict whether a subject has steatohepatitis or no fatty liver disease with about 92% accuracy from analysis of the levels of the biomarkers in samples from the subject. The biomarkers that are the most important biomarkers for distinguishing the groups are listed in Table 6B and displayed in the importance plot in FIG. 2.

TABLE 6B

Most important biomarkers from Random Forest Importance Plot shown in FIG. 2.

| ID | Biomarker |
|---|---|
| 33073 | cysteine-glutathione disulfide (Metabolite-11728) |
| 15140 | kynurenine |
| 32868 | glycocholate* |
| 32412 | butyrylcarnitine |
| 32322 | glutamate |
| 2734 | gamma-glutamyltyrosine |
| 15753 | hippurate |
| 31489 | Metabolite-10914 |
| 32739 | Metabolite-11422 |
| 33420 | gamma-tocopherol- |
| 32881 | Metabolite-11564 |
| 32393 | glutamylvaline |
| 32519 | 1-linoleoylglycerophosphocholine (Metabolite-11205) |
| 32748 | Metabolite-11431 |
| 32701 | urate- |
| 32550 | Metabolite-02272_201 |
| 1299 | tyrosine |
| 32548 | Metabolite-11231 |
| 33362 | gamma-glutamylphenylalanine- |
| 584 | mannose |
| 32675 | Metabolite-03951_200 |
| 32632 | Metabolite-11315 |
| 32846 | Metabolite-11529 |
| 17028 | Metabolite-4611 |
| 32497 | 10c-undecenoate |
| 32749 | Metabolite-11432 |
| 16308 | Metabolite-4147 |
| 32544 | Metabolite-11227 |
| 18497 | taurocholate |
| 32697 | Metabolite-11380 |
| 21047 | 3-methyl-2-oxobutyric acid |
| 1126 | alanine |
| 1647 | glutamine |

TABLE 6B-continued

Most important biomarkers from Random Forest Importance Plot shown in FIG. 2.

| ID | Biomarker |
|---|---|
| 1113 | isocitrate |
| 1125 | isoleucine |
| 60 | leucine |
| 20699 | meso-erythritol |
| 24285 | Metabolite-10026 |
| 30821 | Metabolite-10812 |
| 5628 | Metabolite-1086 |
| 5687 | Metabolite-1110 |
| 6398 | Metabolite-1335 |
| 6847 | Metabolite-1496 |
| 8509 | Metabolite-2041 |
| 10286 | Metabolite-2272 |
| 10715 | Metabolite-2395 |
| 12751 | Metabolite-3073 |
| 12767 | Metabolite-3087 |
| 12780 | Metabolite-3098 |
| 16511 | Metabolite-4274 |
| 18706 | Metabolite-5769 |
| 20267 | Metabolite-7187 |
| 1649 | valine |
| 3147 | xanthine |

TABLE 7

Confusion Matrix showing Steatosis subjects can be distinguished from steatohepatitis (NASH) subjects.
Confusion Matrix: Steatosis vs. NASH

| | Steatosis_Predicted | NASH_Predicted | Error |
|---|---|---|---|
| Steatosis | 10 | 14 | 58% |
| NASH | 5 | 6 | 45% |
| Out_of_bag_error | | 54% | |

Based on the OOB Error rate of 54%, the Random Forest model that was created could be used to predict whether a subject has steatosis or steatohepatitis with about 46% accuracy from analysis of the levels of the biomarkers in samples from the subject.

The compounds that are the most important biomarkers for distinguishing the groups are shown in the importance plots in FIGS. 1, 2, 3. FIG. 1 lists the biomarker compounds that are most important in distinguishing steatosis subjects and Control subjects. Listed in FIG. 2 are the biomarker compounds that are most important in distinguishing steatohepatitis subjects from control subjects. Listed in FIG. 3 are the biomarker compounds that are most important in distinguishing steatosis, steatohepatitis and control subjects.

Example 3 Recursive Partitioning Classification and Receiver Operator Curves (ROC)

Recursive partitioning was performed to uncover the biomarkers that can best differentiate the 2 groups of subjects. It relates a 'dependent' variable (e.g. Group or Y) to a collection of independent ('predictor') variables (e.g. metabolites or X) in order to uncover—or simply understand—the elusive relationship, Y=f(X). It was performed with the JMP program (SAS) to generate a decision tree. The significance level of each "split" of data into the nodes or branches of the tree was computed as p-values, which discern the quality of the split relative to a random event. It was given as LogWorth, which is the negative log 10 of a raw p-value.

Figure 4:
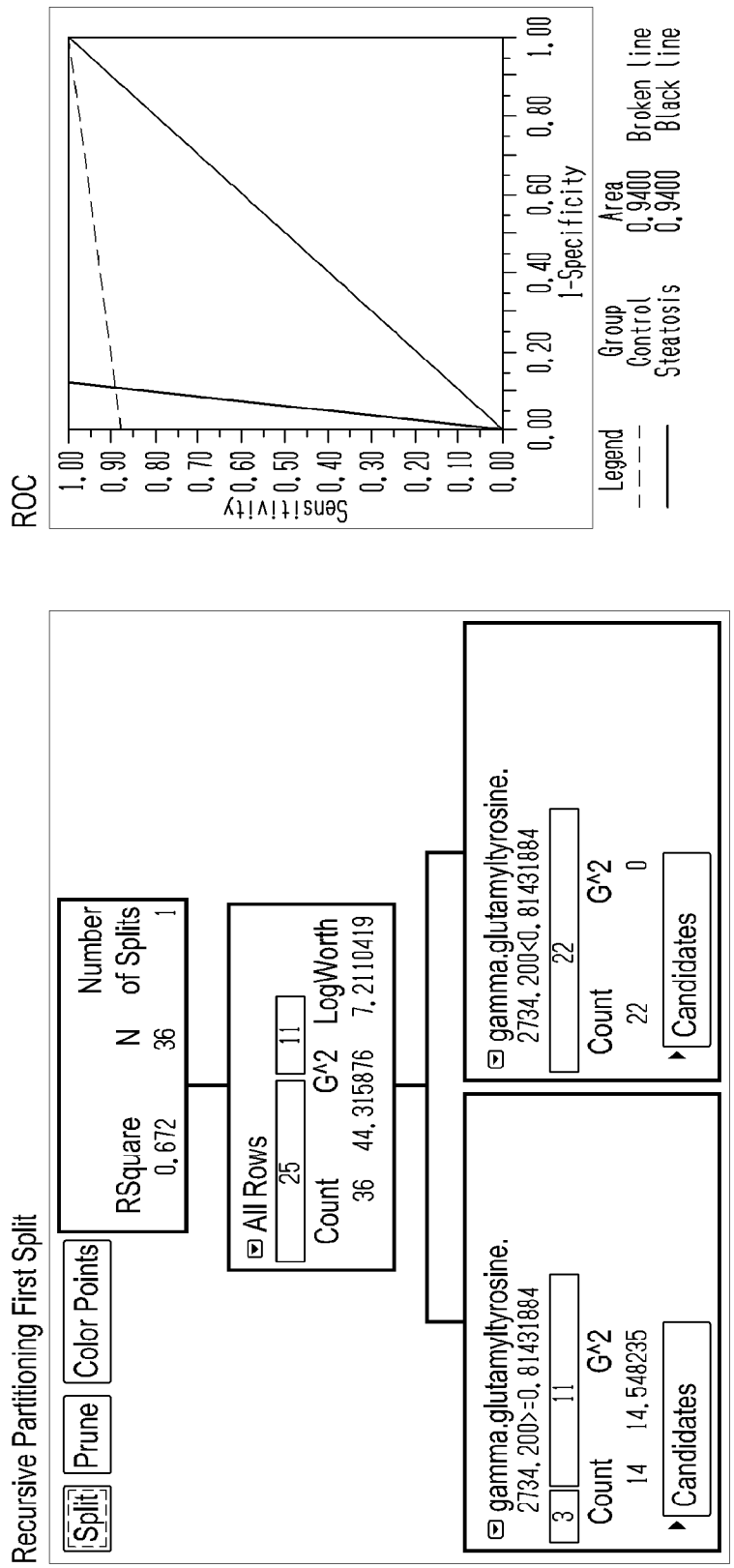
FIG. 4 provides one example of recursive partitioning results showing the classification of Control and steatosis subjects using the biomarkers identified in Table 8.
Figure 5:
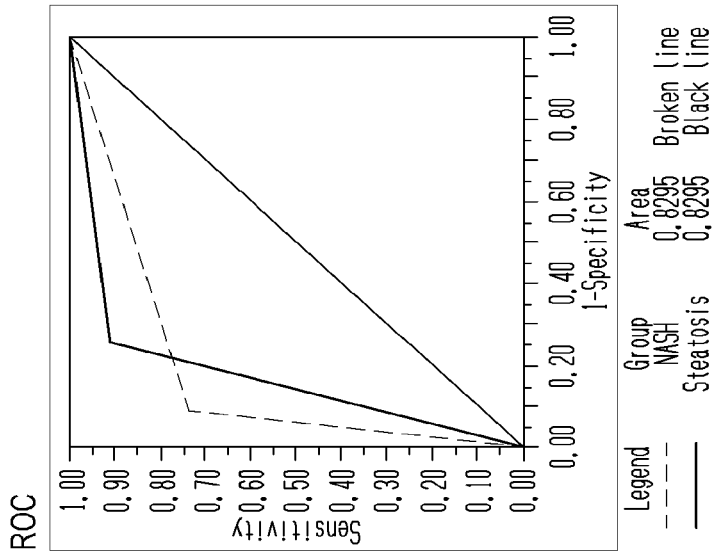
FIG. 5 provides an example of recursive partitioning results showing the classification of steatosis and steatohepatitis (NASH, SH) using the biomarkers listed in Table 9.
Figure 5:
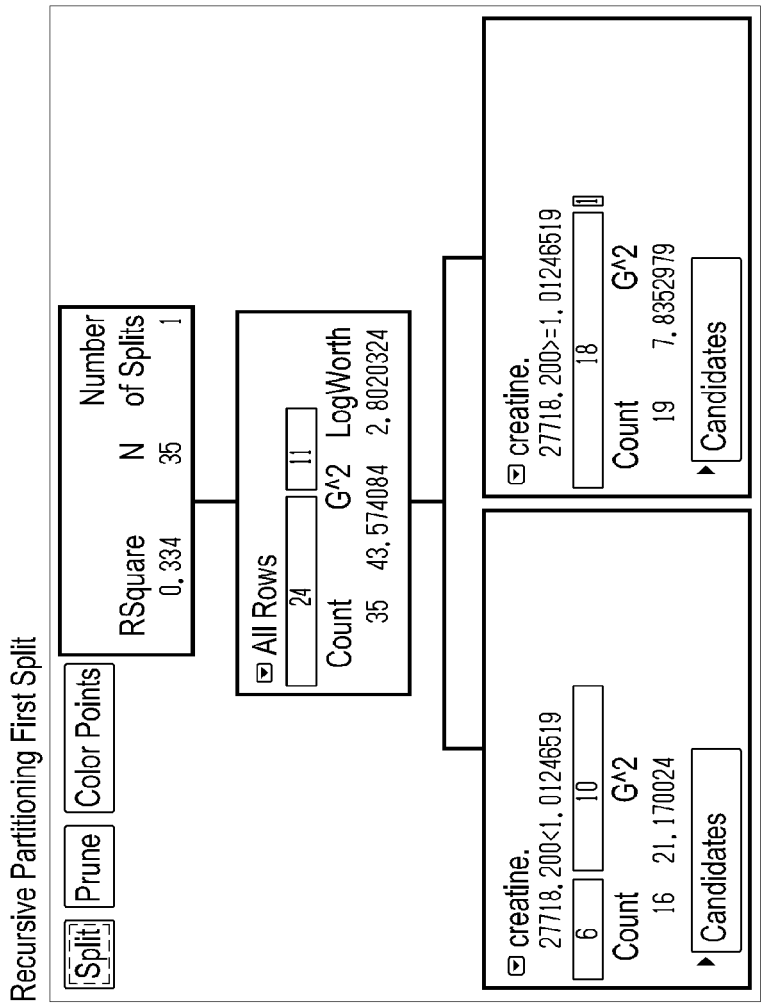
Figure 6:
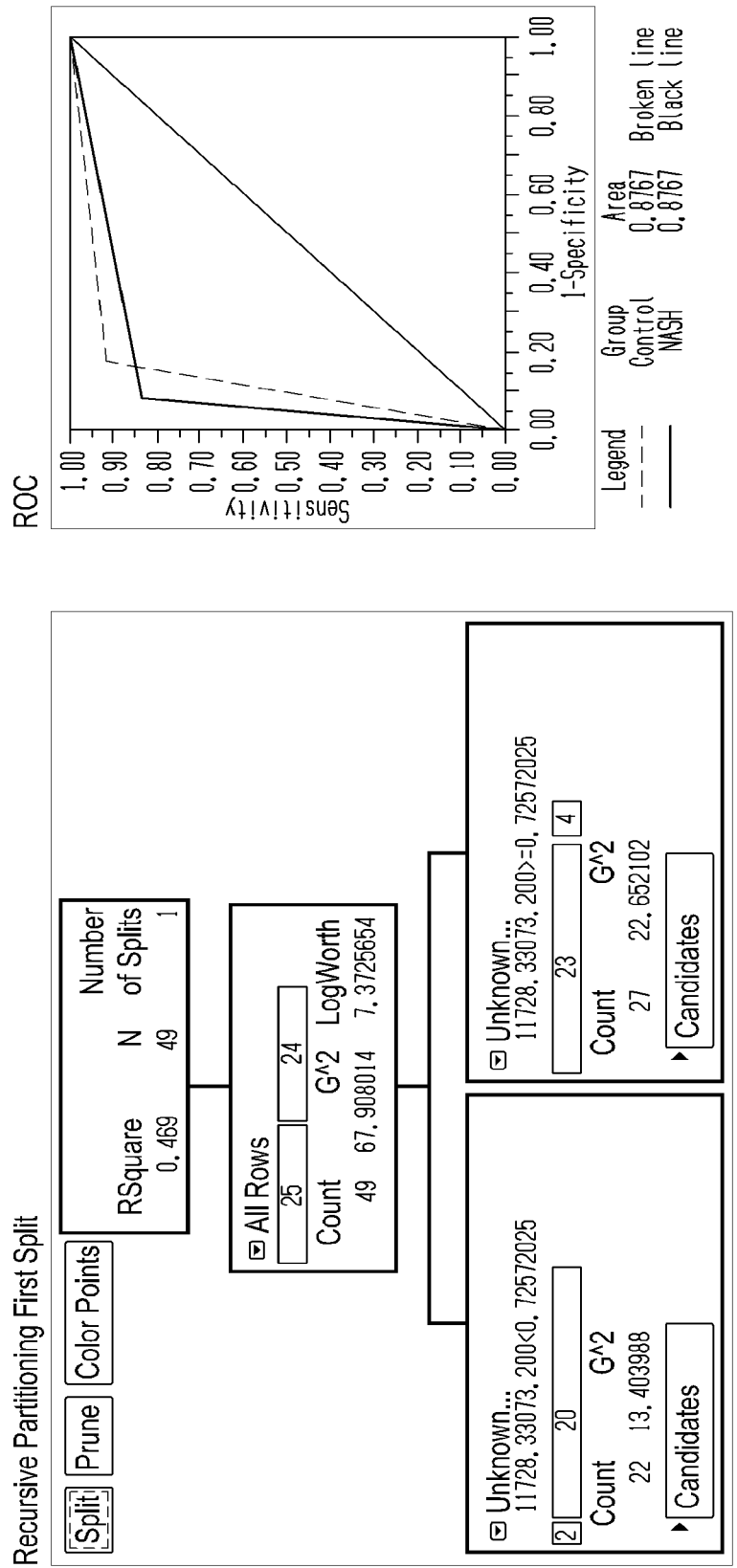
FIG. 6 provides an example of recursive partitioning results showing the classification of control and steatohepatitis using the biomarkers listed in Table 10.

The recursive partitioning results showing the classification of Control and steatosis subjects is shown in FIG. 4. The biomarkers that contribute to the classification are listed in Table 8. The recursive partitioning results showing the classification of steatosis and steatohepatitis (NASH, SH) are shown in FIG. 5 and the biomarkers used in the classification are listed in Table 9. The recursive partitioning results showing the classification of control and steatohepatitis are shown in FIG. 6 and the biomarkers are listed in Table 10. The recursive partitioning results showing the use of the biomarkers to classify steatosis, steatohepatitis and control subjects are shown in FIG. 7 and the biomarkers are listed in Table 11.

The sensitivity and specificity of a given biomarker was determined by the Receiver Operating Characteristic curve (or ROC curve), which plots the true positive rate against the false positive rate for the different possible cutpoints of the specific biomarker. The area under the curve is a measure of test accuracy. An area of 1 represents a perfect test while an area of 0.5 represents a worthless test. A rough guide for classifying the accuracy of a diagnostic test is the traditional academic point system:

0.90-1=excellent
0.80-0.90=good
0.70-0.80=fair
0.60-0.70=poor
0.50-0.60=fail

Figure 7:
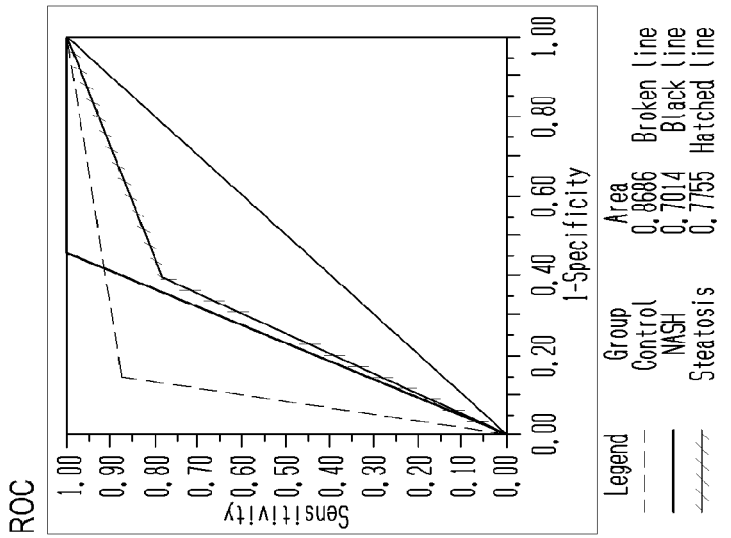
FIG. 7 provides an example of recursive partitioning results showing the use of the biomarkers to classify steatosis, steatohepatitis and control subjects using the biomarkers listed in Table 11.
Figure 7:
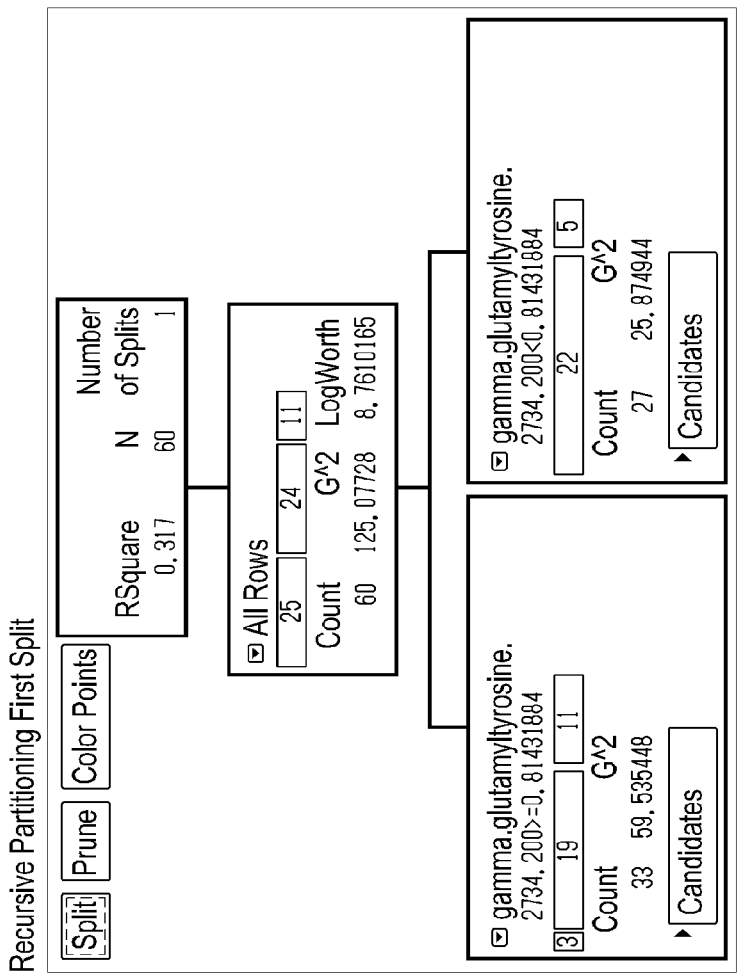

ROC curves are shown in FIGS. 4, 5, 6 and 7. The control subjects are separated from steatosis subjects with an accuracy of >90 (FIG. 4). The steatosis and steatohepatitis subjects can be distinguished with >82% accuracy (FIG. 5). The Control and steatohepatitis subjects are classified >87% accuracy (FIG. 6). The three groups can be classified using the biomarkers with >70% (NASH), >77% (Steatosis), >86% accuracy (control) (FIG. 7).

TABLE 8

Recursive Partitioning Biomarkers, Steatosis vs control.

| ID | COMPOUND | Library | LogWorth | Candidate G^2 |
|---|---|---|---|---|
| 2734 | gamma glutamyltyrosine | 200 | 7.2110 | 29.7676 |
| 18497 | taurocholate | 201 | 4.5487 | 20.2589 |
| 32599 | Metabolite-11282 | 201 | 3.4916 | 17.2822 |
| 20699 | erythritol | 50 | 3.4916 | 17.2822 |
| 32552 | Metabolite-11235 | 201 | 3.3649 | 16.7903 |
| 32322 | glutamate | 50 | 3.3649 | 16.7903 |
| 32393 | glutamylvaline | 200 | 3.0618 | 15.2513 |
| 12763 | Metabolite-3083 | 50 | 3.0147 | 15.2513 |
| 32497 | 10c undecenoate | 201 | 2.9895 | 15.3210 |
| 19490 | Metabolite-6488 | 50 | 2.9743 | 15.2513 |
| 1299 | tyrosine | 200 | 2.9718 | 15.2513 |
| 33242 | Metabolite-11897 | 201 | 2.9718 | 15.2513 |
| 32748 | Metabolite-11431 | 201 | 2.9601 | 15.2052 |
| 32621 | Metabolite-11304 | 200 | 2.8266 | 14.6774 |
| 606 | uridine | 201 | 2.8266 | 14.6774 |
| 17028 | Metabolite-4611 | 50 | 2.8266 | 14.6774 |
| 12789 | Metabolite-3107 | 50 | 2.4680 | 12.6627 |
| 32808 | Metabolite-11491 | 201 | 2.3944 | 12.6627 |
| 32412 | butyrylcarnitine | 200 | 2.3372 | 12.6627 |
| 32547 | Metabolite-11230 | 201 | 2.3242 | 12.6627 |
| 12790 | Metabolite-3108 | 50 | 2.2779 | 12.4746 |
| 33073 | cysteine-glutathione disulfide (Metabolite-11728) | 200 | 2.2201 | 12.1291 |
| 32739 | Metabolite-11422 | 201 | 2.1932 | 12.1291 |
| 30805 | Metabolite-10810 | 50 | 2.1932 | 12.1291 |
| 32776 | 2-methylbutyrylcarnitine (Metabolite-11459) | 200 | 2.1488 | 11.9121 |
| 32697 | Metabolite-11380 | 200 | 2.1443 | 11.9121 |
| 32701 | urate | 200 | 2.1403 | 11.9121 |
| 32559 | Metabolite-11242 | 201 | 2.1279 | 11.8611 |
| 32631 | Metabolite-11314 | 200 | 2.1279 | 11.8611 |
| 32945 | Metabolite-11628 | 201 | 2.1279 | 11.8611 |
| 33386 | Metabolite-12035 | 50 | 2.0266 | 11.2117 |

TABLE 9

RP Biomarker Candidates, steatosis vs. steatohepatitis.

| ID | COMPOUND | Library | LogWorth | Candidate G^2 |
|---|---|---|---|---|
| 27718 | creatine | 200 | 2.8020 | 14.5688 |
| 12067 | undecanoate | 201 | 2.7871 | 14.5095 |
| 32729 | Metabolite-11412 | 200 | 2.5472 | 13.5499 |
| 32855 | Metabolite-11538 | 201 | 2.5472 | 13.5499 |
| 32735 | Metabolite-01911_200 | 200 | 2.4708 | 13.0756 |
| 32621 | Metabolite-11304 | 200 | 2.1940 | 12.1162 |
| 27275 | Metabolite-10507 | 50 | 2.0579 | 11.5561 |

TABLE 10

RP Biomarkers of steatohepatitis (NASH) vs Control.

| ID | COMPOUND | Library | LogWorth | Candidate G^2 |
|---|---|---|---|---|
| 33073 | cysteine-glutathione disulfide (Metabolite-11728) | 200 | 7.3726 | 31.8519 |
| 32868 | glycocholate | 201 | 6.5169 | 28.4230 |
| 15140 | kynurenine | 200 | 6.4082 | 27.7714 |
| 2734 | gamma glutamyltyrosine | 200 | 5.5940 | 24.5076 |
| 32412 | butyrylcarnitine | 200 | 5.4888 | 24.6395 |
| 15753 | hippurate | 201 | 5.2301 | 23.5921 |
| 32322 | glutamate | 50 | 4.5652 | 21.1976 |
| 33420 | gamma tocopherol | 50 | 4.5330 | 21.1976 |
| 32748 | Metabolite-11431 | 201 | 4.3254 | 20.3263 |
| 32739 | Metabolite-11422 | 201 | 4.2214 | 19.9467 |
| 32393 | glutamylvaline | 200 | 3.9888 | 19.1924 |
| 32550 | Metabolite-02272 | 201 | 3.9860 | 19.0839 |
| 31489 | Metabolite-10914 | 50 | 3.8423 | 18.5637 |
| 32519 | 1-linoleoylglycerophosphocholine (Metabolite-11205) | 200 | 3.8117 | 18.4417 |
| 33133 | Metabolite-11788 | 200 | 3.6919 | 17.9988 |
| 32632 | Metabolite-11315 | 200 | 3.6913 | 17.9988 |
| 32548 | Metabolite-11231 | 201 | 3.6260 | 17.7540 |
| 16308 | Metabolite-4147 | 50 | 3.6255 | 17.7540 |
| 32881 | Metabolite-11564 | 201 | 3.5761 | 17.5685 |
| 32675 | Metabolite-03951 | 200 | 3.5752 | 17.5685 |
| 32697 | Metabolite-11380 | 200 | 3.4581 | 17.1290 |
| 32863 | Metabolite-11546 | 201 | 3.4182 | 16.9876 |
| 17028 | Metabolite-4611 | 50 | 3.3802 | 16.8375 |
| 584 | mannose | 50 | 3.3005 | 16.5389 |
| 33362 | gamma glutamylphenylalanine | 200 | 3.1967 | 16.1427 |
| 32749 | Metabolite-11432 | 201 | 3.1952 | 16.1427 |
| 32701 | urate | 200 | 3.1486 | 15.9669 |
| 32846 | Metabolite-11529 | 201 | 3.1224 | 15.8433 |
| 1299 | tyrosine | 200 | 3.1159 | 15.8433 |
| 32544 | Metabolite-11227 | 201 | 3.1019 | 15.7905 |
| 32564 | Metabolite-11247 | 201 | 2.9040 | 15.0281 |
| 32517 | 1-oleoylglycerophosphocholine (Metabolite-11203) | 200 | 2.9012 | 15.0281 |
| 32808 | Metabolite-11491 | 201 | 2.8993 | 14.9830 |
| 33012 | Metabolite-11674 | 200 | 2.8909 | 14.9830 |
| 31787 | 3-carboxyl-4-methyl-5-propyl-2-furanpropanoic acid | 201 | 2.8894 | 14.9830 |
| 20699 | erythritol | 50 | 2.8894 | 14.9830 |
| 32110 | Metabolite-11086 | 50 | 2.8894 | 14.9830 |
| 12783 | Metabolite-3101 | 50 | 2.8894 | 14.9830 |

TABLE 10-continued

RP Biomarkers of steatohepatitis (NASH) vs Control.

| ID | COMPOUND | Library | LogWorth | Candidate G^2 |
|---|---|---|---|---|
| 19402 | Metabolite-6346 | 50 | 2.8894 | 14.9830 |
| 18497 | taurocholate | 201 | 2.6891 | 13.9546 |
| 59 | histidine | 201 | 2.6508 | 14.0671 |
| 12774 | Metabolite-3094 | 50 | 2.6508 | 14.0671 |
| 32682 | Metabolite-11365 | 201 | 2.6217 | 13.9546 |
| 33227 | Metabolite-11882 | 201 | 2.5727 | 13.7651 |
| 15990 | glycerophosphorylcholine (GPC) | 200 | 2.5636 | 13.7298 |
| 32547 | Metabolite-11230 | 201 | 2.5131 | 13.5334 |
| 32497 | X10c undecanoate | 201 | 2.4846 | 13.4226 |
| 32549 | Metabolite-02269 | 201 | 2.4738 | 13.3217 |
| 32552 | Metabolite-11235 | 201 | 2.4690 | 13.3619 |
| 32385 | Metabolite-11180 | 50 | 2.4078 | 13.0513 |
| 32621 | Metabolite-11304 | 200 | 2.3922 | 13.0617 |
| 20488 | glucose | 50 | 2.3922 | 13.0617 |
| 16865 | Metabolite-4522 | 50 | 2.3036 | 12.7022 |
| 64 | phenylalanine | 200 | 2.2026 | 12.3145 |
| 32637 | Metabolite-11320 | 201 | 2.1916 | 12.2709 |
| 32813 | Metabolite-11496 | 201 | 2.1916 | 12.2709 |
| 32854 | Metabolite-11537 | 200 | 2.1916 | 12.2709 |
| 27256 | Metabolite-10500 | 50 | 2.1916 | 12.2709 |
| 32346 | glycochenodeoxycholate | 201 | 2.1443 | 11.9681 |
| 32656 | Metabolite-11339 | 201 | 2.0482 | 11.6993 |
| 16650 | Metabolite-4360 | 50 | 2.0204 | 11.5103 |
| 607 | urocanate | 200 | 2.0135 | 10.2237 |
| 32559 | Metabolite-11242 | 201 | 2.0012 | 11.5103 |

TABLE 11

RP Biomarkers of Steatosis vs Steatohepatitis (NASH) Vs Control.

| ID | COMPOUND | Library | LogWorth | Candidate G^2 |
|---|---|---|---|---|
| 2734 | gamma glutamyltyrosine | 200 | 8.7610 | 39.6669 |
| 33073 | cysteine-glutathione disulfide (Metabolite-11728) | 200 | 6.9137 | 33.1250 |
| 32868 | glycocholate | 201 | 5.6594 | 28.4476 |
| 32412 | butyrylcarnitine | 200 | 5.5221 | 27.9670 |
| 15140 | kynurenine | 200 | 5.4648 | 27.7794 |
| 32322 | glutamate | 50 | 5.4202 | 27.6254 |
| 18497 | taurocholate | 201 | 4.8465 | 25.6695 |
| 32748 | Metabolite-11431 | 201 | 4.5458 | 24.5681 |
| 32393 | glutamylvaline | 200 | 4.4325 | 24.1102 |
| 1299 | tyrosine | 200 | 4.4170 | 24.1102 |
| 15753 | hippurate | 201 | 4.2727 | 23.5947 |
| 32739 | Metabolite-11422 | 201 | 3.9941 | 22.5914 |
| 17028 | Metabolite-4611 | 50 | 3.7736 | 21.7885 |
| 33420 | gamma tocopherol | 50 | 3.6961 | 21.4058 |
| 20699 | erythritol | 50 | 3.4424 | 20.5670 |
| 31489 | Metabolite-10914 | 50 | 3.4147 | 20.4362 |
| 32552 | Metabolite-11235 | 201 | 3.4135 | 20.4592 |
| 32697 | Metabolite-11380 | 200 | 3.2207 | 19.7221 |
| 32519 | 1-linoleoylglycerophosphocholine (Metabolite-11205) | 200 | 3.2148 | 19.7148 |
| 32749 | Metabolite-11432 | 201 | 3.1735 | 19.5592 |
| 33362 | gamma glutamylphenylalanine | 200 | 3.1317 | 19.2619 |
| 32846 | Metabolite-11529 | 201 | 3.1175 | 19.1830 |
| 32550 | Metabolite-02272_201 | 201 | 3.0781 | 19.1976 |
| 32808 | Metabolite-11491 | 201 | 2.9873 | 18.6852 |
| 32547 | Metabolite-11230 | 201 | 2.9438 | 18.6852 |
| 16308 | Metabolite-4147 | 50 | 2.8966 | 18.4875 |
| 32548 | Metabolite-11231 | 201 | 2.8923 | 18.4875 |
| 33133 | Metabolite-11788 | 200 | 2.8602 | 18.3636 |
| 32735 | Metabolite-01911_200 | 200 | 2.8564 | 18.1394 |
| 32863 | Metabolite-11546 | 201 | 2.8379 | 18.1709 |
| 32881 | Metabolite-11564 | 201 | 2.8103 | 18.1709 |
| 33242 | Metabolite-11897 | 201 | 2.8094 | 18.1676 |
| 32675 | Metabolite-03951_200 | 200 | 2.7808 | 18.0072 |
| 59 | histidine | 201 | 2.7802 | 18.0542 |
| 32632 | Metabolite-11315 | 200 | 2.7704 | 17.9993 |
| 27718 | creatine | 200 | 2.6480 | 17.5391 |
| 32701 | urate | 200 | 2.6462 | 17.5321 |
| 584 | mannose | 50 | 2.6462 | 17.5321 |
| 32599 | Metabolite-11282 | 201 | 2.5826 | 17.2822 |
| 32559 | Metabolite-11242 | 201 | 2.5799 | 17.2717 |
| 32497 | 10c undecenoate | 201 | 2.5001 | 16.9560 |
| 606 | uridine | 201 | 2.4079 | 16.5890 |
| 32621 | Metabolite-11304 | 200 | 2.4027 | 16.5683 |
| 12783 | Metabolite-3101 | 50 | 2.4027 | 16.5683 |
| 32564 | Metabolite-11247 | 201 | 2.3935 | 16.4772 |
| 32517 | 1-oleoylglycerophosphocholine (Metabolite-11203) | 200 | 2.3800 | 16.4772 |
| 12763 | Metabolite-3083 | 50 | 2.3715 | 16.2338 |
| 32544 | Metabolite-11227 | 201 | 2.3539 | 16.3727 |

TABLE 11-continued

RP Biomarkers of Steatosis vs Steatohepatitis (NASH) Vs Control.

| ID | COMPOUND | Library | LogWorth | Candidate $\hat{G}2$ |
|---|---|---|---|---|
| 19490 | Metabolite-6488 | 50 | 2.3240 | 16.2338 |
| 12067 | undecanoate | 201 | 2.3176 | 16.2264 |
| 32854 | Metabolite-11537 | 200 | 2.2206 | 15.7775 |
| 32813 | Metabolite-11496 | 201 | 2.2068 | 15.7775 |
| 32945 | Metabolite-11628 | 201 | 2.1937 | 15.7238 |
| 32110 | Metabolite-11086 | 50 | 2.1659 | 15.6103 |
| 19402 | Metabolite-6346 | 50 | 2.1659 | 15.6103 |
| 31787 | 3-carboxyl-4-methyl-5-propyl-2-furanpropanoic acid | 201 | 2.1292 | 15.4023 |
| 32729 | Metabolite-11412 | 200 | 2.1279 | 15.4545 |
| 32549 | Metabolite-02269 | 201 | 2.0837 | 15.0750 |
| 15990 | glycerophosphorylcholine GPC | 200 | 2.0516 | 15.1396 |
| 33012 | Metabolite-11674 | 200 | 2.0280 | 14.9832 |
| 32385 | Metabolite-11180 | 50 | 2.0268 | 14.8693 |

Example 4 Biomarkers and Gender

Biomarkers were discovered by (1) analyzing blood plasma samples from different groups of female human subjects and from different groups of male human subjects to determine the levels of metabolites in the samples and then (2) statistically analyzing the results to determine those metabolites that were differentially present in the two groups.

For males, the plasma samples used for the analysis were 7 control samples that were from healthy subjects, 6 samples from patients with steatosis and 8 samples from patients with steatohepatitis. For females, the plasma samples used for the analysis were 18 control samples that were from healthy subjects, 5 samples from patients with steatosis and 16 samples from patients with steatohepatitis. In both the male and the female studies, after the levels of metabolites were determined, the data was analyzed using significance tests (ANOVA, ANCOVA, Wilcoxon).

ANOVA was used to identify significant differences in the mean levels of metabolites between two populations (i.e., Steatosis vs. Control, Steatohepatitis vs. Control, Steatosis vs. Steatohepatitis).

Biomarkers:

As listed below in Tables 12 (male subjects) and 13 (female subjects), biomarkers were discovered that were differentially present between plasma samples from steatosis patients and Control subjects, biomarkers that were discovered that were differentially present between plasma samples from patients with steatohepatitis and from Control subjects and biomarkers that were discovered that were differentially present between plasma samples from steatosis and plasma samples from subjects with steatohepatitis (i.e. NASH).

Tables 12 and 13 include, for each listed biomarker, the p-value and the q-value determined in the statistical analysis of the data concerning the biomarkers in the steatosis mean level as compared to the control mean level, the NASH mean level as compared to the control mean level, and the steatosis mean level as compared to the NASH mean level. Library indicates the chemical library that was used to identify the compounds. The number 50 refer to the GC library and the number 61 refers to the LC library. Comp ID refers to the identification number for the compound in our internal chemical compound database.

Table 12 lists biomarkers for males, including, for each biomarker, the p-value and q-value for the specified comparisons of groups as described above.

TABLE 12

Biomarkers from male subjects with Steatosis compared to Control subjects, steatohepatitis (NASH) compared to Control subjects and Steatosis compared to steatohepatitis (NASH) subjects.

| COMPOUND | COMP_ID | LIBRARY | Control vs. NASH | | Control vs. STEATOSIS | | NASH vs. STEATOSIS | |
|---|---|---|---|---|---|---|---|---|
| | | | p-value | q-value | p-value | q-value | p-value | q-value |
| stearate | 1358 | 50 | 4.00E−04 | 0.0633 | 0.0128 | 0.2286 | 0.3457 | 0.7893 |
| palmitate | 1336 | 50 | 9.00E−04 | 0.0633 | 0.0091 | 0.1836 | 0.5612 | 0.8289 |
| isoleucine | 1125 | 50 | 0.0011 | 0.0633 | 0.0025 | 0.1264 | 0.9729 | 0.8893 |
| glutamate | 57 | 50 | 0.0011 | 0.0633 | 0.0305 | 0.2368 | 0.3124 | 0.7803 |
| Metabolite-9033 | 22570 | 50 | 0.0021 | 0.0872 | 0.2901 | 0.66 | 0.0507 | 0.6206 |
| Metabolite-3087 | 12767 | 50 | 0.0031 | 0.0872 | 0.1491 | 0.4771 | 0.1507 | 0.7628 |
| valine | 1649 | 50 | 0.0034 | 0.0872 | 0.0243 | 0.2368 | 0.5868 | 0.832 |
| isoleucine | 18118 | 50 | 0.0036 | 0.0872 | 0.0019 | 0.1264 | 0.6472 | 0.8475 |
| glutamate | 12751 | 50 | 0.0036 | 0.0872 | 0.0472 | 0.2804 | 0.4112 | 0.8022 |
| Metabolite-4274 | 16511 | 50 | 0.0038 | 0.0872 | 0.106 | 0.3961 | 0.2349 | 0.7803 |
| linoleate | 1105 | 50 | 0.0049 | 0.0872 | 0.051 | 0.2862 | 0.4508 | 0.8145 |
| leucine | 60 | 50 | 0.0054 | 0.0872 | 0.0175 | 0.2368 | 0.8025 | 0.8527 |
| Metabolite-5769 | 18706 | 61 | 0.0054 | 0.0872 | 0.0025 | 0.1264 | 0.626 | 0.8421 |
| isocitrate | 1113 | 61 | 0.0055 | 0.0872 | 0.094 | 0.3845 | 0.3151 | 0.7803 |
| Metabolite-2041 | 8509 | 61 | 0.0059 | 0.0872 | 0.0536 | 0.2922 | 0.4791 | 0.8182 |
| Metabolite-2270 | 10247 | 61 | 0.0061 | 0.0872 | 0.0206 | 0.2368 | 0.7827 | 0.8519 |
| Metabolite- | 31510 | 61 | 0.007 | 0.0872 | 0.0338 | 0.2455 | 0.6578 | 0.8475 |

TABLE 12-continued

Biomarkers from male subjects with Steatosis compared to Control subjects, steatohepatitis (NASH) compared to Control subjects and Steatosis compared to steatohepatitis (NASH) subjects.

| COMPOUND | COMP_ID | LIBRARY | Control vs. NASH | | Control vs. STEATOSIS | | NASH vs. STEATOSIS | |
|---|---|---|---|---|---|---|---|---|
| | | | p-value | q-value | p-value | q-value | p-value | q-value |
| 10932 | | | | | | | | |
| alanine | 1126 | 50 | 0.0072 | 0.0872 | 0.0298 | 0.2368 | 0.7063 | 0.8475 |
| tyrosine | 12780 | 50 | 0.0073 | 0.0872 | 0.0272 | 0.2368 | 0.7393 | 0.8519 |
| Metabolite-8214 | 21421 | 50 | 0.0085 | 0.0948 | 0.0925 | 0.3845 | 0.398 | 0.8022 |
| glucose | 20488 | 50 | 0.0095 | 0.0948 | 0.0911 | 0.3845 | 0.4236 | 0.8022 |
| Metabolite-10439 | 25609 | 50 | 0.0098 | 0.0948 | 0.0341 | 0.2455 | 0.7445 | 0.8519 |
| Metabolite-1496 | 6847 | 61 | 0.0098 | 0.0948 | 0.9827 | 0.8655 | 0.0124 | 0.348 |
| choline | 15506 | 61 | 0.01 | 0.0948 | 0.6398 | 0.7767 | 0.0429 | 0.6206 |
| glutamine | 1647 | 50 | 0.0116 | 0.1058 | 0.1325 | 0.4409 | 0.3566 | 0.7893 |
| Metabolite-9855 | 24233 | 61 | 0.0121 | 0.1061 | 0.8754 | 0.8551 | 0.0105 | 0.3457 |
| Metabolite-7187 | 20267 | 61 | 0.0145 | 0.1218 | 0.4129 | 0.698 | 0.1218 | 0.7385 |
| Metabolite-5646 | 18591 | 61 | 0.0157 | 0.1272 | 0.4187 | 0.698 | 0.0021 | 0.2874 |
| 3-methyl-2-oxobutyric acid | 21047 | 61 | 0.0164 | 0.1281 | 0.1039 | 0.3961 | 0.5063 | 0.8289 |
| Metabolite-4096 | 16186 | 61 | 0.0169 | 0.1281 | 0.1525 | 0.4771 | 0.3895 | 0.8005 |
| Metabolite-9727 | 24077 | 50 | 0.0185 | 0.1342 | 0.0298 | 0.2368 | 0.9767 | 0.8893 |
| Metabolite-1911 | 7933 | 61 | 0.0189 | 0.1342 | 0.6182 | 0.7691 | 0.0064 | 0.2874 |

Table 13 lists biomarkers for females, including, for each biomarker, the p-value and the q-value for the specified comparisons of groups as described above.

TABLE 13

Biomarkers from female subjects with Steatosis compared to Control subjects, steatohepatitis (NASH) compared to Control subjects and Steatosis compared to steatohepatitis (NASH) subjects.

| COMPOUND | COMP_ID | LIB_ID | Control vs. NASH | | Control vs. STEATOSIS | | NASH vs. STEATOSIS | |
|---|---|---|---|---|---|---|---|---|
| | | | p-value | q-value | p-value | q-value | p-value | q-value |
| glutamate | 57 | 50 | 1.73E−08 | 3.22E−06 | 0.0023 | 0.0904 | 0.2067 | 0.6864 |
| urate | 1604 | 50 | 3.32E−07 | 3.08E−05 | 0.0278 | 0.2958 | 0.1005 | 0.6474 |
| glutamate | 12751 | 50 | 8.91E−07 | 1.00E−04 | 0.0036 | 0.0977 | 0.4745 | 0.6864 |
| Metabolite-5769 | 18706 | 61 | 4.24E−06 | 2.00E−04 | 8.00E−04 | 0.0661 | 0.9332 | 0.7199 |
| isocitrate | 1113 | 61 | 8.14E−06 | 3.00E−04 | 0.255 | 0.4932 | 0.0342 | 0.4905 |
| Metabolite-10026 | 24285 | 61 | 1.94E−05 | 6.00E−04 | 0.0231 | 0.2804 | 0.4083 | 0.6864 |
| glycocholate | 18476 | 61 | 2.91E−05 | 8.00E−04 | 0.0172 | 0.2557 | 0.5271 | 0.6864 |
| L-kynurenine | 15140 | 61 | 1.00E−04 | 0.0013 | 0.9893 | 0.73 | 0.0051 | 0.432 |
| Metabolite-3330 | 13600 | 61 | 1.00E−04 | 0.0016 | 0.1335 | 0.3923 | 0.1878 | 0.6864 |
| leucine | 60 | 50 | 1.00E−04 | 0.0016 | 0.104 | 0.3726 | 0.241 | 0.6864 |
| valine | 1649 | 50 | 1.00E−04 | 0.0019 | 0.0938 | 0.3726 | 0.288 | 0.6864 |
| isoleucine | 1125 | 50 | 1.00E−04 | 0.0013 | 0.0574 | 0.3465 | 0.3262 | 0.6864 |
| Metabolite-1110 | 5687 | 61 | 1.00E−04 | 0.0016 | 0.0032 | 0.0977 | 0.8124 | 0.6937 |
| Metabolite-10951 | 31595 | 61 | 2.00E−04 | 0.0026 | 0.2368 | 0.4917 | 0.1503 | 0.6474 |
| Metabolite-4522 | 16865 | 50 | 2.00E−04 | 0.0021 | 0.0689 | 0.359 | 0.3877 | 0.6864 |
| Metabolite-4274 | 16511 | 50 | 2.00E−04 | 0.0021 | 0.0431 | 0.3397 | 0.516 | 0.6864 |
| Isobar-47-includes-taurochenodeoxycholic acid-and-taurodeoxycholic acid | 18882 | 61 | 2.00E−04 | 0.0021 | 0.032 | 0.3148 | 0.5941 | 0.6868 |
| tyrosine | 1299 | 61 | 3.00E−04 | 0.0026 | 0.0548 | 0.3465 | 0.492 | 0.6864 |
| alanine | 1126 | 50 | 4.00E−04 | 0.0036 | 0.1507 | 0.414 | 0.2717 | 0.6864 |
| thyroxine | 2761 | 61 | 5.00E−04 | 0.0043 | 0.2645 | 0.5014 | 0.1712 | 0.6644 |
| Metabolite-2347 | 10551 | 61 | 5.00E−04 | 0.0048 | 0.0022 | 0.0904 | 0.4853 | 0.6864 |
| Metabolite-10812 | 30821 | 50 | 7.00E−04 | 0.0058 | 0.1583 | 0.421 | 0.3247 | 0.6864 |
| Metabolite-2269- | 10245 | 61 | 7.00E−04 | 0.0056 | 0.0025 | 0.0904 | 0.4809 | 0.6864 |
| glutamine | 1647 | 50 | 9.00E−04 | 0.0067 | 0.1091 | 0.3726 | 0.458 | 0.6864 |
| meso-erythritol | 20699 | 50 | 0.001 | 0.0067 | 0.1995 | 0.463 | 0.2975 | 0.6864 |

TABLE 13-continued

Biomarkers from female subjects with Steatosis compared to Control subjects, steatohepatitis (NASH) compared to Control subjects and Steatosis compared to steatohepatitis (NASH) subjects.

| COMPOUND | COMP_ID | LIB_ID | Control vs. NASH | | Control vs. STEATOSIS | | NASH vs. STEATOSIS | |
|---|---|---|---|---|---|---|---|---|
| | | | p-value | q-value | p-value | q-value | p-value | q-value |
| Metabolite-3183 | 13214 | 61 | 0.001 | 0.0067 | 0.106 | 0.3726 | 0.4805 | 0.6864 |
| docosahexaenoate-DHA- | 19323 | 50 | 0.001 | 0.0067 | 0.0405 | 0.3397 | 0.7884 | 0.6896 |
| Metabolite-4627 | 17068 | 61 | 0.001 | 0.0067 | 0.0268 | 0.2958 | 0.9307 | 0.7199 |
| Isobar-66-includes-glycochenodeoxycholic acid-glycodeoxycholic acid | 22803 | 61 | 0.0011 | 0.0067 | 0.0519 | 0.3465 | 0.7198 | 0.6896 |
| 5-oxoproline | 1494 | 50 | 0.0012 | 0.0076 | 0.1022 | 0.3726 | 0.5195 | 0.6864 |
| Metabolite-10589 | 27801 | 61 | 0.0013 | 0.0078 | 0.2598 | 0.4988 | 0.2575 | 0.6864 |
| mannose | 584 | 50 | 0.0013 | 0.0078 | 0.0435 | 0.3397 | 0.8177 | 0.6937 |
| Metabolite-4360 | 16650 | 50 | 0.0015 | 0.0083 | 0.6433 | 0.6655 | 0.0796 | 0.5826 |
| gamma-L-glutamyl-L-tyrosine | 2734 | 61 | 0.0016 | 0.009 | 0.3615 | 0.5823 | 0.1942 | 0.6864 |
| Metabolite-1086 | 5628 | 61 | 0.0017 | 0.0092 | 0.6934 | 0.6655 | 0.0743 | 0.5826 |
| phenylalanine | 64 | 61 | 0.0019 | 0.0095 | 0.1746 | 0.4408 | 0.4085 | 0.6864 |
| lactate | 527 | 50 | 0.0019 | 0.0095 | 0.1018 | 0.3726 | 0.586 | 0.6868 |
| arachidonate | 1110 | 50 | 0.002 | 0.0098 | 0.8148 | 0.6934 | 0.0194 | 0.4834 |
| Metabolite-7187 | 20267 | 61 | 0.0021 | 0.0098 | 0.747 | 0.6811 | 0.0705 | 0.5824 |
| Metabolite-1914 | 7941 | 61 | 0.0021 | 0.0098 | 0.0075 | 0.1505 | 0.5693 | 0.6868 |
| Metabolite-3109 | 12791 | 50 | 0.0024 | 0.0109 | 0.783 | 0.6934 | 0.0195 | 0.4834 |
| tyrosine | 12780 | 50 | 0.0031 | 0.0138 | 0.0321 | 0.3148 | 0.9228 | 0.7184 |
| xanthine | 3147 | 61 | 0.0032 | 0.0138 | 0.2695 | 0.5014 | 0.3371 | 0.6864 |
| Metabolite-1496 | 6847 | 61 | 0.0035 | 0.0149 | 0.3752 | 0.5823 | 0.005 | 0.432 |
| Metabolite-2041 | 8509 | 61 | 0.0037 | 0.0154 | 0.3041 | 0.5383 | 0.3177 | 0.6864 |
| 3-4-5-trimethoxy-cinnamic acid | 18291 | 61 | 0.0045 | 0.0183 | 0.0182 | 0.2557 | 0.6793 | 0.6896 |
| Metabolite-3951 | 15529 | 61 | 0.0049 | 0.0192 | 0.0586 | 0.3465 | 0.9515 | 0.7253 |
| Metabolite-3994 | 16016 | 61 | 0.005 | 0.0192 | 0.0249 | 0.2887 | 0.7558 | 0.6896 |
| Metabolite-3094 | 12774 | 50 | 0.0055 | 0.0209 | 0.6697 | 0.6655 | 0.0218 | 0.4834 |
| Metabolite-9855 | 24233 | 61 | 0.0058 | 0.0216 | 0.124 | 0.3816 | 0.7024 | 0.6896 |
| Metabolite-5726 | 18657 | 61 | 0.006 | 0.022 | 0.7399 | 0.6781 | 0.1182 | 0.6474 |
| glycerol | 15122 | 50 | 0.0065 | 0.0229 | 0.0928 | 0.3726 | 0.8347 | 0.6975 |
| Metabolite-2395 | 10715 | 61 | 0.0066 | 0.0229 | 0.0016 | 0.0904 | 0.1741 | 0.6654 |
| Metabolite-4986 | 17627 | 50 | 0.0067 | 0.0229 | 0.1963 | 0.4608 | 0.5502 | 0.6868 |
| 3-methyl-2-oxobutyric acid | 21047 | 61 | 0.0069 | 0.0234 | 0.0928 | 0.3726 | 0.8462 | 0.6991 |
| Metabolite-2259 | 10156 | 61 | 0.0071 | 0.0235 | 0.6427 | 0.6655 | 0.1628 | 0.6474 |
| Metabolite-3230 | 13296 | 61 | 0.0072 | 0.0235 | 0.6656 | 0.6655 | 0.1545 | 0.6474 |
| palmitate | 1336 | 50 | 0.0075 | 0.0237 | 0.3757 | 0.5823 | 0.3312 | 0.6864 |
| Metabolite-1911 | 7933 | 61 | 0.0075 | 0.0237 | 0.1736 | 0.4408 | 0.6183 | 0.6868 |
| Metabolite-2291 | 10414 | 61 | 0.0079 | 0.0245 | 0.0098 | 0.1787 | 0.4316 | 0.6864 |
| pyruvate | 599 | 61 | 0.0118 | 0.0359 | 0.9667 | 0.7259 | 0.0792 | 0.5826 |
| Isobar-1-includes-mannose-fructose-glucose-galactose-alpha-L-sorbopyranose-Inositol-D-allose-D--altrose-D-psicone-L--gulose-allo-inositol | 10737 | 61 | 0.0126 | 0.0375 | 0.055 | 0.3465 | 0.8389 | 0.6975 |
| Metabolite-2272 | 10286 | 61 | 0.0128 | 0.0375 | 0.0731 | 0.359 | 0.94 | 0.7208 |
| lysine | 1301 | 50 | 0.0132 | 0.0384 | 0.271 | 0.5014 | 0.5375 | 0.6864 |
| uridine | 606 | 61 | 0.0139 | 0.0397 | 0.1016 | 0.3726 | 0.9509 | 0.7253 |
| Metabolite-2390 | 10672 | 61 | 0.0143 | 0.0402 | 0.0557 | 0.3465 | 0.8179 | 0.6937 |
| Metabolite-9043 | 22600 | 50 | 0.0154 | 0.0427 | 0.0118 | 0.2006 | 0.375 | 0.6864 |
| Metabolite-2329 | 10544 | 61 | 0.0157 | 0.0429 | 0.3917 | 0.5823 | 0.4157 | 0.6864 |
| Metabolite-9033 | 22570 | 50 | 0.0163 | 0.0437 | 0.0719 | 0.359 | 0.883 | 0.7052 |
| Metabolite-4251 | 16496 | 50 | 0.018 | 0.0478 | 0.7335 | 0.6781 | 0.1998 | 0.6864 |

TABLE 13-continued

Biomarkers from female subjects with Steatosis compared to Control subjects, steatohepatitis (NASH) compared to Control subjects and Steatosis compared to steatohepatitis (NASH) subjects.

| COMPOUND | COMP_ID | LIB_ID | Control vs. NASH | | Control vs. STEATOSIS | | NASH vs. STEATOSIS | |
|---|---|---|---|---|---|---|---|---|
| | | | p-value | q-value | p-value | q-value | p-value | q-value |
| Metabolite-4276 | 16518 | 50 | 0.0183 | 0.0479 | 0.3795 | 0.5823 | 0.4523 | 0.6864 |
| Metabolite-10932 | 31510 | 61 | 0.02 | 0.0515 | 0.6694 | 0.6655 | 0.2414 | 0.6864 |
| Metabolite-3323 | 13557 | 61 | 0.0221 | 0.0561 | 0.4812 | 0.657 | 0.3823 | 0.6864 |
| Metabolite-3016 | 12644 | 50 | 0.0229 | 0.0575 | 0.0038 | 0.0977 | 0.1636 | 0.6474 |
| Metabolite-1981 | 8210 | 61 | 0.0248 | 0.0613 | 0.2371 | 0.4917 | 0.7138 | 0.6896 |
| Metabolite-3088 | 12768 | 50 | 0.0272 | 0.0663 | 0.8115 | 0.6934 | 0.0842 | 0.5956 |
| Metabolite-3087 | 12767 | 50 | 0.0295 | 0.0712 | 0.2356 | 0.4917 | 0.7535 | 0.6896 |
| Metabolite-10797 | 30728 | 61 | 0.0309 | 0.0735 | 0.7815 | 0.6934 | 0.2311 | 0.6864 |
| Metabolite-3100 | 12782 | 50 | 0.0316 | 0.0742 | 0.0624 | 0.3465 | 0.6928 | 0.6896 |
| 2-amino butyrate | 12645 | 50 | 0.033 | 0.0756 | 0.3666 | 0.5823 | 0.5717 | 0.6868 |
| threonine | 1284 | 50 | 0.033 | 0.0756 | 0.1048 | 0.3726 | 0.8734 | 0.7052 |
| Metabolite-3707 | 14837 | 61 | 0.0338 | 0.0761 | 0.019 | 0.2557 | 0.3591 | 0.6864 |
| Metabolite-1834 | 7650 | 61 | 0.0343 | 0.0761 | 4.00E−04 | 0.0646 | 0.0289 | 0.4905 |
| Metabolite-10785 | 30633 | 61 | 0.0344 | 0.0761 | 0.0612 | 0.3465 | 0.6678 | 0.6896 |
| Metabolite-2139 | 9130 | 61 | 0.0349 | 0.0762 | 0.4999 | 0.6647 | 0.4382 | 0.6864 |
| Metabolite-4613 | 17033 | 61 | 0.0375 | 0.0808 | 0.4934 | 0.663 | 0.4563 | 0.6864 |
| gluconate | 587 | 50 | 0.039 | 0.083 | 0.9105 | 0.7087 | 0.1966 | 0.6864 |
| N-acetylglycine | 27710 | 50 | 0.0396 | 0.083 | 0.1303 | 0.3923 | 0.9192 | 0.7177 |
| Metabolite-10507 | 27275 | 50 | 0.0398 | 0.083 | 0.8432 | 0.6996 | 0.1135 | 0.6474 |
| threonate | 27738 | 50 | 0.0404 | 0.0834 | 0.5847 | 0.6655 | 0.3906 | 0.6864 |
| p-hydroxyphenyl-lactate-HPLA- | 1431 | 50 | 0.0411 | 0.0837 | 0.7669 | 0.6934 | 0.0954 | 0.6428 |
| palmitoleate | 1507 | 50 | 0.0427 | 0.0854 | 0.6825 | 0.6655 | 0.3285 | 0.6864 |
| Metabolite-3995 | 16019 | 61 | 0.0428 | 0.0854 | 0.6036 | 0.6655 | 0.3849 | 0.6864 |
| Metabolite-2231 | 9905 | 61 | 0.0463 | 0.0913 | 0.3818 | 0.5823 | 0.6207 | 0.6868 |
| Metabolite-3165 | 13142 | 61 | 0.0481 | 0.0939 | 0.0439 | 0.3397 | 0.4996 | 0.6864 |
| stearate | 1358 | 50 | 0.0486 | 0.0939 | 0.7225 | 0.6781 | 0.3214 | 0.6864 |
| Metabolite-9726 | 24076 | 50 | 0.0504 | 0.0954 | 0.6042 | 0.6655 | 0.0688 | 0.5824 |
| serine | 12663 | 50 | 0.0504 | 0.0954 | 0.578 | 0.6655 | 0.4331 | 0.6864 |
| Metabolite-5774 | 18723 | 61 | 0.0514 | 0.0964 | 0.8537 | 0.6996 | 0.254 | 0.6864 |
| Metabolite-10933 | 31518 | 50 | 0.0578 | 0.1062 | 0.2685 | 0.5014 | 0.0197 | 0.4834 |
| Metabolite-2321 | 10501 | 61 | 0.0918 | 0.1468 | 0.3393 | 0.5814 | 0.0402 | 0.4905 |
| Isobar-60-includes-s-2-hydroxybutyric acid-2-hydroxyiso-butyric acid | 22261 | 61 | 0.1198 | 0.1696 | 0.2887 | 0.5228 | 0.0389 | 0.4905 |
| threonine | 12666 | 50 | 0.131 | 0.18 | 0.3057 | 0.5383 | 0.0454 | 0.5204 |
| Metabolite-2821 | 11923 | 61 | 0.1533 | 0.1987 | 5.00E−04 | 0.0646 | 0.0098 | 0.4834 |
| creatine | 27718 | 61 | 0.1942 | 0.2211 | 0.1218 | 0.3816 | 0.0183 | 0.4834 |
| paraxanthine | 18254 | 61 | 0.2253 | 0.247 | 0.0823 | 0.3726 | 0.013 | 0.4834 |
| Metabolite-3443 | 14125 | 61 | 0.2434 | 0.258 | 0.1778 | 0.4408 | 0.0371 | 0.4905 |
| fructose | 577 | 50 | 0.2708 | 0.2732 | 0.2032 | 0.4674 | 0.0487 | 0.5204 |
| theophylline | 18394 | 61 | 0.3262 | 0.301 | 0.15 | 0.414 | 0.0399 | 0.4905 |
| alpha-keto-glutarate | 528 | 61 | 0.364 | 0.3232 | 0.0187 | 0.2557 | 0.004 | 0.432 |
| Metabolite-6346 | 19402 | 50 | 0.4153 | 0.3451 | 0.0919 | 0.3726 | 0.029 | 0.4905 |
| Metabolite-8506 | 21762 | 61 | 0.4328 | 0.3491 | 0.0711 | 0.359 | 0.0227 | 0.4834 |
| Metabolite-1667 | 7132 | 61 | 0.4557 | 0.3628 | 0.1102 | 0.3726 | 0.0398 | 0.4905 |
| caffeine | 569 | 61 | 0.462 | 0.3658 | 0.036 | 0.3397 | 0.0114 | 0.4834 |
| Metabolite-4238 | 16471 | 61 | 0.9278 | 0.51 | 0.0226 | 0.2804 | 0.0282 | 0.4905 |

Example 5 Analytical Characteristics

Analytical Characterization of Unnamed Biomarkers Compounds:

Table 14 below includes analytical characteristics of each of the isobars and the unnamed metabolites listed in Tables 1-3 and 8-13 above. The table includes, for each listed Metabolite, the Metabolite ID (ID), the retention time (RT), retention index (RI), mass, library, and polarity obtained using the analytical methods described above. "Metabolite ID" refers to the unique identifier for that compound in our internal chemical library database. "Mass" refers to the mass of the C12 isotope of the parent ion used in quantification of the compound. The values for "Library" give an indication of the analytical method used for quantification: "50" indicates GC-MS and "61", "200" and "201" indicate LC-MS. "Polarity" indicates the polarity of the quantitative ion as being either positive (+) or negative (−).

TABLE 14

Analytical Characteristics of Unnamed Metabolites.

| ID | Biomarker | Library | RT | RI | MASS | Polarity |
|---|---|---|---|---|---|---|
| 1882 | Isobar 47 includes taurochenodeoxycholic acid and taurodeoxycholic acid | 61 | 15.51 | 15700.0 | 498.4 | − |
| 5628 | Metabolite-1086 | 61 | 4.56 | 4811.0 | 294.1 | + |
| 6398 | Metabolite-1335 | 61 | 8.74 | 9162.2 | 367.2 | + |
| 6847 | Metabolite-1496 | 61 | 1.53 | 1562.0 | 133.0 | − |
| 7933 | Metabolite-1911 | 61 | 11.42 | 11799.6 | 464.1 | + |
| 10501 | Metabolite-2321 | 61 | 13.44 | 12940.0 | 314.3 | + |
| 10629 | Metabolite-2386 | 61 | 11.94 | 12150.0 | 539.2 | − |
| 10737 | Isobar 1 includes mannose, fructose, glucose, galactose, alpha-L-sorbopyranose, Inositol, D-allose,D-(+)-altrose, D-psicone,L-(+)-gulose, allo-nositol | 61 | 1.45 | 1481.0 | 215.0 | − |
| 11923 | Metabolite-2821 | 61 | 6.80 | 7980.0 | 119.1 | + |
| 12593 | Metabolite-2973 | 50 | 4.74 | 1213.4 | 281 | + |
| 12604 | Metabolite-2981 | 50 | 5.21 | 1265.2 | 210.9 | + |
| 12626 | Metabolite-3003 | 50 | 6.79 | 1446.6 | 218.1 | + |
| 12754 | Metabolite-3075 | 50 | 10.36 | 1857.9 | 204 | + |
| 12757 | Metabolite-3078 | 50 | 10.65 | 1887 | 203.1 | + |
| 12761 | Metabolite-3081 | 50 | 10.89 | 1911.5 | 204 | + |
| 12763 | Metabolite-3083 | 50 | 10.94 | 1916.1 | 204 | + |
| 12769 | Metabolite-3089 | 50 | 11.28 | 1951.5 | 116.9 | + |
| 12770 | Metabolite-3090 | 50 | 11.31 | 1955 | 243.1 | + |
| 12771 | Metabolite-3091 | 50 | 11.41 | 1966.2 | 232.1 | + |
| 12774 | Metabolite-3094 | 50 | 11.55 | 1980.6 | 299 | + |
| 12781 | Metabolite-3099 | 50 | 11.77 | 2005.2 | 204 | + |
| 12782 | Metabolite-3100 | 50 | 11.85 | 2013.2 | 204 | + |
| 12783 | Metabolite-3101 | 50 | 11.93 | 2022.2 | 290 | + |
| 12785 | Metabolite-3103 | 50 | 12.09 | 2039.8 | 290.1 | + |
| 12789 | Metabolite-3107 | 50 | 12.21 | 2053.2 | 204.1 | + |
| 12790 | Metabolite-3108 | 50 | 12.24 | 2056.5 | 246 | + |
| 13142 | Metabolite-3165 | 61 | 8.38 | 8472.2 | 265.0 | + |
| 13214 | Metabolite-3183 | 61 | 9.37 | 9441.0 | 295.2 | + |
| 13296 | Metabolite-3230 | 61 | 3.10 | 3043.2 | 245.0 | + |
| 13557 | Metabolite-3323 | 61 | 14.47 | 14696.5 | 624.4 | − |
| 13600 | Metabolite-3330 | 61 | 14.06 | 14292.2 | 514.3 | − |
| 15529 | Metabolite-3951 | 61 | 8.41 | 8705.4 | 367.1 | + |
| 16016 | Metabolite-3994 | 61 | 1.63 | 1640.4 | 427.0 | + |
| 16019 | Metabolite-3995 | 61 | 2.19 | 2230.0 | 207.7 | − |
| 16138 | Metabolite-4080 | 50 | 14.02 | 2270.2 | 299 | + |
| 16308 | Metabolite-4147 | 50 | 10.07 | 1767.1 | 290.2 | + |
| 16337 | Metabolite-4167 | 61 | 11.03 | 10920.4 | 286.2 | + |
| 16650 | Metabolite-4360 | 50 | 9.15 | 1678.2 | 347.2 | + |
| 16665 | Metabolite-4364 | 50 | 10.66 | 1852.4 | 232 | + |
| 16666 | Metabolite-4365 | 50 | 11.05 | 1892.9 | 204 | + |
| 16819 | Metabolite-4496 | 50 | 6.76 | 1398.2 | 204 | + |
| 16829 | Metabolite-4503 | 50 | 8.39 | 1589 | 227.2 | + |
| 16865 | Metabolite-4522 | 50 | 12.26 | 2025.4 | 217.1 | + |
| 16959 | Metabolite-4595 | 50 | 5.65 | 1274.4 | 130 | + |
| 17028 | Metabolite-4611 | 50 | 8.07 | 1546.6 | 292.1 | + |
| 17033 | Metabolite-4613 | 61 | 12.73 | 12778.0 | 541.4 | − |
| 17068 | Metabolite-4627 | 61 | 10.84 | 11034.9 | 591.3 | + |
| 17304 | Metabolite-4759 | 61 | 11.80 | 11906.0 | 310.2 | + |
| 17627 | Metabolite-4986 | 50 | 11.56 | 1956.4 | 204.1 | + |
| 18232 | Metabolite-5403 | 50 | 5.92 | 1300.2 | 319 | + |
| 18591 | Metabolite-5646 | 61 | 8.96 | 8750.0 | 228.0 | − |
| 18657 | Metabolite-5726 | 61 | 14.05 | 13757.0 | 417.3 | − |
| 18706 | Metabolite-5769 | 61 | 11.12 | 10753.2 | 485.2 | − |
| 18868 | Metabolite-5847 | 50 | 12.35 | 2040 | 288.2 | + |
| 18929 | Metabolite-5907 | 50 | 8.69 | 1643.2 | 229.1 | + |
| 19363 | Metabolite-6227 | 50 | 5 | 1210.5 | 196.1 | + |
| 19368 | Metabolite-6267 | 50 | 9.32 | 1704.5 | 257.1 | + |
| 19370 | Metabolite-6268 | 50 | 9.91 | 1773.8 | 271.1 | + |
| 19374 | Metabolite-6270 | 50 | 11.35 | 1929.6 | 320.2 | + |
| 19402 | Metabolite-6346 | 50 | 8 | 1550.8 | 263.2 | + |
| 19490 | Metabolite-6488 | 50 | 12.25 | 2021.7 | 204.1 | + |
| 19985 | Metabolite-6957 | 50 | 11.71 | 1966 | 290.1 | + |
| 20267 | Metabolite-7187 | 61 | 8.38 | 8500.0 | 328.0 | + |
| 20950 | Metabolite-7846 | 50 | 5.1 | 1208.1 | 145.1 | + |
| 21418 | Isobar 56-pipecolate; aminocyclopentane carboxylic acid | 61 | 2.45 | 2850.0 | 130.1 | + |
| 21762 | Metabolite-8506 | 61 | 8.92 | 8811.0 | 475.1 | + |

TABLE 14-continued

Analytical Characteristics of Unnamed Metabolites.

| ID | Biomarker | Library | RT | RI | MASS | Polarity |
|---|---|---|---|---|---|---|
| 22261 | Isobar 60 includes (s)-2-hydroxybutyric acid,2-hydroxyisobutyric acid | 61 | 4.26 | 4725.0 | 148.9 | − |
| 24233 | Metabolite-9855 | 61 | 11.85 | 11605.3 | 462.2 | − |
| 24285 | Metabolite-10026 | 61 | 9.47 | 9300.3 | 259.1 | − |
| 27801 | Metabolite-10589 | 61 | 15.43 | 17536.8 | 619.3 | − |
| 30633 | Metabolite-10785 | 61 | 11.49 | 12073.4 | 363.0 | + |
| 30728 | Metabolite-10797 | 61 | 10.92 | 11563.3 | 352.2 | − |
| 31510 | Metabolite-10932 | 61 | 11.54 | 11928.0 | 190.0 | + |
| 31529 | Metabolite-10941 | 61 | 3.60 | 4101.0 | 191.8 | + |
| 32514 | Metabolite-11200 | 200 | 5.62 | 5637 | 496.4 | + |
| 32516 | Metabolite-11202 | 200 | 5.8 | 5823 | 524.4 | + |
| 32517 | 1-oleoylglycerophosphocholine (Metabolite-11203) | 200 | 5.65 | 5665 | 522.4 | + |
| 32518 | Metabolite-11204 | 200 | 5.26 | 5263 | 229.2 | + |
| 32519 | 1-linoleoylglycerophosphocholine (Metabolite-11205) | 200 | 5.55 | 5558 | 520.4 | + |
| 32520 | Metabolite-11206 | 200 | 0.59 | 575 | 138.8 | + |
| 32545 | Metabolite-11228 | 201 | 1.15 | 1136 | 278.1 | − |
| 32547 | Metabolite-11230 | 201 | 1.44 | 1438 | 278.1 | − |
| 32548 | Metabolite-11231 | 201 | 1.47 | 1471 | 330 | − |
| 32549 | Metabolite-02269 | 201 | 1.55 | 1551 | 255.1 | − |
| 32550 | Metabolite-02272 | 201 | 1.97 | 1958 | 189 | − |
| 32551 | Metabolite-11234 | 201 | 2.01 | 2001 | 334.1 | − |
| 32552 | Metabolite-11235 | 201 | 2.04 | 2033 | 326.1 | − |
| 32553 | Metabolite-03832 | 201 | 2.2 | 2199 | 173.1 | − |
| 32557 | Metabolite-06126 | 201 | 2.69 | 2684 | 203.1 | − |
| 32559 | Metabolite-11242 | 201 | 2.96 | 2958 | 360 | − |
| 32560 | Metabolite-07765 | 201 | 3.71 | 3705 | 245.1 | − |
| 32561 | Metabolite-11244 | 201 | 3.78 | 3771 | 224.2 | − |
| 32562 | Metabolite-11245 | 201 | 3.91 | 3902 | 238.3 | − |
| 32563 | Metabolite-11246 | 201 | 3.94 | 3930 | 143.2 | − |
| 32564 | Metabolite-11247 | 201 | 3.94 | 3932 | 213.1 | − |
| 32566 | Metabolite-11249 | 200 | 1.24 | 1271 | 280.1 | + |
| 32567 | Metabolite-11250 | 200 | 1.3 | 1339 | 150.2 | + |
| 32571 | Metabolite-11254 | 200 | 2.05 | 2095 | 328.1 | + |
| 32572 | Metabolite-11255 | 200 | 2.38 | 2442 | 247.1 | + |
| 32575 | Metabolite-11258 | 200 | 2.89 | 2941 | 362 | + |
| 32578 | Metabolite-11261 | 200 | 3.69 | 3732 | 286.2 | + |
| 32587 | Metabolite-02249 | 201 | 4.03 | 4025 | 267.2 | − |
| 32588 | Metabolite-01327 | 201 | 4.25 | 4242 | 583.2 | − |
| 32590 | Metabolite-11273 | 201 | 4.56 | 4552 | 369.2 | − |
| 32593 | Metabolite-02036 | 200 | 4.94 | 4985 | 616.2 | + |
| 32596 | Metabolite-02250 | 200 | 5.14 | 5158 | 286.2 | + |
| 32599 | Metabolite-11282 | 201 | 4.77 | 4763 | 254.8 | − |
| 32602 | Metabolite-11285 | 200 | 5.28 | 5260 | 288.1 | + |
| 32609 | Metabolite-01345 | 201 | 4.9 | 4887 | 369.2 | − |
| 32616 | Metabolite-11299 | 201 | 4.9 | 4893 | 507.2 | − |
| 32619 | Metabolite-11302 | 201 | 5.01 | 4998 | 397.3 | − |
| 32620 | Metabolite-11303 | 201 | 5.02 | 5015 | 512.3 | − |
| 32621 | Metabolite-11304 | 200 | 0.8 | 801 | 217.1 | + |
| 32625 | Metabolite-11308 | 201 | 5.15 | 5133 | 365.3 | − |
| 32631 | Metabolite-11314 | 200 | 0.64 | 634 | 243 | + |
| 32632 | Metabolite-11315 | 200 | 1.19 | 1210 | 130.2 | + |
| 32634 | Metabolite-11317 | 201 | 5.81 | 5703 | 219.3 | − |
| 32635 | Metabolite-11318 | 201 | 5.81 | 5699 | 476.3 | − |
| 32636 | Metabolite-11319 | 201 | 5.81 | 5700 | 269.4 | − |
| 32637 | Metabolite-11320 | 201 | 5.85 | 5740 | 593.9 | − |
| 32638 | Metabolite-11321 | 201 | 6.15 | 5997 | 569.9 | − |
| 32641 | Metabolite-11324 | 201 | 6.24 | 6075 | 596 | − |
| 32643 | Metabolite-11326 | 201 | 6.35 | 6160 | 213.2 | + |
| 32644 | Metabolite-11327 | 200 | 5.16 | 5176 | 269.2 | + |
| 32648 | Metabolite-11331 | 201 | 0.69 | 686 | 164.2 | − |
| 32651 | Metabolite-11334 | 200 | 0.96 | 982 | 259.1 | + |
| 32652 | Metabolite-11335 | 200 | 0.97 | 991 | 229.2 | + |
| 32654 | Metabolite-11337 | 200 | 1 | 1020 | 160.2 | + |
| 32656 | Metabolite-11339 | 201 | 0.69 | 689 | 156.2 | − |
| 32670 | Metabolite-11353 | 200 | 0.8 | 811 | 203.2 | + |
| 32671 | Metabolite-11354 | 200 | 0.76 | 770 | 146.2 | + |
| 32672 | Metabolite-02546 | 200 | 0.75 | 764 | 129.2 | + |
| 32675 | Metabolite-03951 | 200 | 1.87 | 1912 | 367.1 | + |
| 32682 | Metabolite-11365 | 201 | 5.61 | 5527 | 303.3 | − |
| 32689 | Metabolite-11372 | 201 | 5.35 | 5303 | 467.4 | − |
| 32691 | Metabolite-11374 | 200 | 0.69 | 690 | 370.9 | + |
| 32692 | Metabolite-11375 | 200 | 0.73 | 732 | 309.1 | + |

TABLE 14-continued

Analytical Characteristics of Unnamed Metabolites.

| ID | Biomarker | Library | RT | RI | MASS | Polarity |
|---|---|---|---|---|---|---|
| 32694 | Metabolite-11377 | 200 | 0.77 | 770 | 249.2 | + |
| 32696 | Metabolite-11379 | 201 | 5.65 | 5566 | 267.3 | − |
| 32697 | Metabolite-11380 | 200 | 1.04 | 1053 | 339.8 | + |
| 32698 | Metabolite-11381 | 200 | 1.11 | 1126 | 186.2 | + |
| 32699 | Metabolite-11382 | 200 | 1.16 | 1180 | 250.8 | + |
| 32702 | Metabolite-11385 | 200 | 1.38 | 1430 | 312.1 | + |
| 32703 | Metabolite-11386 | 200 | 1.47 | 1525 | 344.1 | + |
| 32704 | Metabolite-11387 | 200 | 1.65 | 1699 | 294.1 | + |
| 32707 | Metabolite-11390 | 200 | 2 | 2041 | 100.2 | + |
| 32709 | Metabolite-03056 | 200 | 2.21 | 2264 | 185.2 | + |
| 32710 | Metabolite-11393 | 200 | 2.34 | 2403 | 367.1 | + |
| 32717 | Metabolite-11400 | 200 | 2.81 | 2855 | 710.1 | + |
| 32718 | Metabolite-01342 | 200 | 2.8 | 2848 | 265.1 | + |
| 32722 | Metabolite-11405 | 200 | 3.02 | 3075 | 264.8 | + |
| 32729 | Metabolite-11412 | 200 | 3.78 | 3836 | 204.2 | + |
| 32732 | Metabolite-11415 | 201 | 0.69 | 692 | 313.1 | − |
| 32734 | Metabolite-10954 | 200 | 4.14 | 4229 | 288.2 | + |
| 32735 | Metabolite-01911 | 200 | 4.26 | 4354 | 464.1 | + |
| 32738 | Metabolite-11421 | 200 | 4.54 | 4634 | 314.2 | + |
| 32739 | Metabolite-11422 | 201 | 0.89 | 884 | 151.1 | − |
| 32740 | Metabolite-11423 | 201 | 1.05 | 1038 | 260.1 | − |
| 32741 | Metabolite-11424 | 200 | 4.58 | 4664 | 227.1 | + |
| 32744 | Metabolite-11427 | 201 | 1.16 | 1145 | 181.1 | − |
| 32746 | Metabolite-11429 | 201 | 1.16 | 1151 | 245.1 | − |
| 32747 | Metabolite-01142 | 201 | 1.19 | 1176 | 117.2 | − |
| 32748 | Metabolite-11431 | 201 | 1.58 | 1575 | 330 | − |
| 32749 | Metabolite-11432 | 201 | 1.89 | 1886 | 292.1 | − |
| 32751 | Metabolite-11434 | 201 | 2.11 | 2107 | 370.1 | − |
| 32752 | Metabolite-11435 | 201 | 2.14 | 2131 | 365.1 | − |
| 32753 | Metabolite-09789 | 201 | 2.62 | 2613 | 153.1 | − |
| 32754 | Metabolite-11437 | 201 | 2.89 | 2888 | 231 | − |
| 32755 | Metabolite-11438 | 201 | 3.1 | 3092 | 241.2 | − |
| 32756 | Metabolite-02276 | 201 | 3.35 | 3339 | 199.1 | − |
| 32757 | Metabolite-11440 | 201 | 3.58 | 3571 | 246.3 | − |
| 32758 | Metabolite-11441 | 201 | 3.78 | 3773 | 331.1 | − |
| 32759 | Metabolite-11442 | 201 | 3.91 | 3902 | 331.1 | − |
| 32760 | Metabolite-11443 | 201 | 3.92 | 3910 | 225.3 | − |
| 32761 | Metabolite-11444 | 201 | 3.99 | 3983 | 541.2 | − |
| 32762 | Metabolite-11445 | 201 | 4.01 | 3995 | 239.3 | − |
| 32764 | Metabolite-11447 | 200 | 0.98 | 989 | 278.1 | + |
| 32767 | Metabolite-11450 | 201 | 4.11 | 4103 | 224.2 | − |
| 32769 | Metabolite-11452 | 201 | 4.12 | 4109 | 352.1 | − |
| 32776 | 2-methylbutyrylcarnitine (Metabolite-11459) | 200 | 2.49 | 2545 | 246.2 | + |
| 32786 | Metabolite-11469 | 200 | 3.82 | 3874 | 239.1 | + |
| 32787 | Metabolite-11470 | 201 | 4.16 | 4151 | 525.2 | − |
| 32792 | Metabolite-11475 | 201 | 4.25 | 4240 | 383.2 | − |
| 32793 | Metabolite-11476 | 200 | 4.52 | 4616 | 189.1 | + |
| 32795 | Metabolite-11478 | 201 | 4.3 | 4286 | 165.2 | − |
| 32797 | Metabolite-11480 | 201 | 4.42 | 4406 | 229 | − |
| 32800 | Metabolite-11483 | 201 | 4.45 | 4443 | 505.2 | − |
| 32802 | Metabolite-11485 | 201 | 4.49 | 4478 | 378.2 | − |
| 32807 | Metabolite-11490 | 201 | 4.77 | 4762 | 279.8 | − |
| 32808 | Metabolite-11491 | 201 | 4.85 | 4846 | 567.3 | − |
| 32813 | Metabolite-11496 | 201 | 5.58 | 5508 | 271.3 | − |
| 32814 | Metabolite-11497 | 201 | 5.37 | 5324 | 233.3 | − |
| 32815 | Metabolite-11498 | 201 | 5.78 | 5674 | 500.3 | − |
| 32822 | Metabolite-11505 | 201 | 1.61 | 1614 | 101.2 | − |
| 32825 | Metabolite-11508 | 201 | 2.97 | 2987 | 173.2 | − |
| 32827 | Metabolite-11510 | 201 | 3.92 | 3925 | 385.2 | − |
| 32829 | Metabolite-03653 | 200 | 0.82 | 826 | 144.2 | + |
| 32838 | Metabolite-11521 | 200 | 3.71 | 3755 | 286.2 | + |
| 32839 | Metabolite-11522 | 201 | 4.76 | 4754 | 313.2 | − |
| 32845 | Metabolite-11528 | 200 | 4.74 | 4832 | 316.3 | + |
| 32846 | Metabolite-11529 | 201 | 4.85 | 4845 | 624.3 | − |
| 32847 | Metabolite-11530 | 201 | 4.87 | 4866 | 313.2 | − |
| 32848 | Metabolite-11531 | 201 | 4.86 | 4850 | 391.3 | − |
| 32854 | Metabolite-11537 | 200 | 5.14 | 5160 | 366.3 | + |
| 32855 | Metabolite-11538 | 201 | 4.93 | 4920 | 311.3 | − |
| 32858 | Metabolite-11541 | 201 | 4.99 | 4984 | 399 | − |
| 32863 | Metabolite-11546 | 201 | 5.02 | 5015 | 448.4 | − |
| 32865 | Metabolite-11548 | 201 | 5.09 | 5081 | 391.3 | − |
| 32866 | Metabolite-11549 | 201 | 5.11 | 5093 | 339.3 | − |
| 32878 | Metabolite-11561 | 201 | 1.26 | 1252 | 267.1 | − |
| 32879 | Metabolite-11562 | 201 | 0.98 | 972 | 197.1 | − |
| 32880 | Metabolite-11563 | 201 | 0.98 | 971 | 115.2 | − |

TABLE 14-continued

Analytical Characteristics of Unnamed Metabolites.

| ID | Biomarker | Library | RT | RI | MASS | Polarity |
|---|---|---|---|---|---|---|
| 32881 | Metabolite-11564 | 201 | 1.2 | 1188 | 177.1 | − |
| 32910 | Metabolite-11593 | 201 | 0.79 | 790 | 189.2 | − |
| 32912 | Metabolite-11595 | 201 | 0.92 | 919 | 665 | − |
| 32914 | Metabolite-11597 | 201 | 1 | 991 | 665 | − |
| 32926 | Metabolite-11609 | 201 | 1.48 | 1490 | 310.1 | − |
| 32945 | Metabolite-11628 | 201 | 3.14 | 3133 | 360.1 | − |
| 32952 | Metabolite-02277 | 201 | 3.61 | 3604 | 201.1 | − |
| 32954 | Metabolite-06132 | 201 | 3.66 | 3655 | 321.1 | − |
| 32965 | Metabolite-11648 | 201 | 4.84 | 4819 | 534.3 | − |
| 32970 | Metabolite-11653 | 201 | 5.82 | 5686 | 331.3 | − |
| 32971 | Metabolite-11654 | 200 | 2.53 | 2500 | 246.2 | + |
| 32978 | Metabolite-11656 | 200 | 0.6 | 612 | 227 | + |
| 33012 | Metabolite-11674 | 200 | 1.14 | 1151 | 189.1 | + |
| 33072 | Metabolite-11727 | 200 | 0.71 | 709 | 241 | + |
| 33073 | cysteine-glutathione disulfide (Metabolite-11728) | 200 | 0.8 | 804 | 427 | + |
| 33084 | Metabolite-11739 | 200 | 3.15 | 3239 | 769 | + |
| 33131 | Metabolite-11786 | 200 | 0.87 | 864 | 136 | + |
| 33132 | Metabolite-11787 | 200 | 1.13 | 1126 | 148.1 | + |
| 33133 | Metabolite-11788 | 200 | 1.17 | 1161 | 245 | + |
| 33138 | Metabolite-11793 | 200 | 3.57 | 3634 | 601.1 | + |
| 33140 | Metabolite-11795 | 200 | 1.46 | 1457 | 148.1 | + |
| 33154 | Metabolite-11809 | 200 | 5.23 | 5248 | 381.5 | + |
| 33159 | Metabolite-11814 | 200 | 2.39 | 2372 | 152.1 | + |
| 33163 | Metabolite-11818 | 200 | 2.56 | 2535 | 146.1 | + |
| 33169 | Metabolite-11824 | 201 | 1.4 | 1402 | 326.1 | − |
| 33171 | Metabolite-11826 | 201 | 1.48 | 1489 | 194.1 | − |
| 33173 | Metabolite-11828 | 201 | 1.69 | 1703 | 246.1 | − |
| 33174 | Metabolite-11829 | 201 | 1.8 | 1813 | 230 | − |
| 33178 | Metabolite-11833 | 201 | 1.97 | 1977 | 260.1 | − |
| 33183 | Metabolite-11838 | 201 | 2.3 | 2314 | 276 | − |
| 33188 | Metabolite-11843 | 201 | 2.69 | 2710 | 230.1 | − |
| 33190 | Metabolite-11845 | 201 | 2.87 | 2891 | 615 | − |
| 33192 | Metabolite-11847 | 201 | 3.05 | 3074 | 259.2 | − |
| 33194 | Metabolite-11849 | 201 | 3.2 | 3229 | 266.2 | − |
| 33198 | Metabolite-11853 | 201 | 3.59 | 3602 | 187.1 | − |
| 33203 | Metabolite-11858 | 201 | 4.42 | 4400 | 437.1 | − |
| 33206 | Metabolite-11861 | 201 | 4.63 | 4617 | 229.2 | − |
| 33209 | Metabolite-11864 | 201 | 5.02 | 5012 | 280.9 | − |
| 33216 | Metabolite-11871 | 200 | 5.25 | 5249 | 370.3 | + |
| 33219 | Metabolite-11874 | 201 | 5.23 | 5199 | 197.3 | − |
| 33225 | Metabolite-11880 | 201 | 5.44 | 5378 | 537.4 | − |
| 33227 | Metabolite-11882 | 201 | 5.52 | 5445 | 301.3 | − |
| 33228 | 1-arachidonoylglycerophosphocholine (Metabolite-11883) | 200 | 5.54 | 5524 | 544.3 | + |
| 33232 | Metabolite-11887 | 201 | 5.85 | 5736 | 307.4 | − |
| 33237 | Metabolite-11892 | 201 | 0.71 | 710 | 367.1 | − |
| 33242 | Metabolite-11897 | 201 | 1.69 | 1664 | 292.1 | − |
| 33248 | Metabolite-11903 | 201 | 2.53 | 2484 | 283.1 | − |
| 33250 | Metabolite-11905 | 201 | 4.44 | 4401 | 283.2 | − |
| 33252 | Metabolite-11907 | 201 | 5.06 | 5036 | 313.3 | − |
| 33254 | Metabolite-11909 | 201 | 5.3 | 5272 | 297.3 | − |
| 33258 | Metabolite-11913 | 201 | 5.43 | 5402 | 275.3 | − |
| 33265 | Metabolite-11920 | 200 | 0.68 | 686 | 268.1 | + |
| 33323 | Metabolite-11977 | 200 | 3.21 | 3287 | 270.1 | + |
| 33366 | Metabolite-12020 | 200 | 5.15 | 5178 | 424.4 | + |
| 33380 | Metabolite-12029 | 201 | 0.68 | 683 | 329.1 | − |

Example 6

Additional metabolomic analysis was performed on the samples obtained from the study cohorts described in Example 1. Additional statistical analysis was also performed as described below.

Metabolomic Analysis

The global, unbiased metabolic profiling platform was based on a combination of 3 independent platforms: ultra-high-performance liquid chromatography/tandem mass spectrometry (UHPLC/MS/MS) optimized for basic species, UHPLC/MS/MS optimized for acidic species, and gas chromatography/mass spectrometry (GC/MS). The major components of the process are summarized as follows:

Sample Extraction:

One hundred microliters of each plasma sample was thawed on ice and extracted using an automated MicroLab STAR system (Hamilton, Salt Lake City, Utah) in 400 μL of methanol containing the recovery standards.

GC/MS and UHPLC/MS/MS Analysis:

UHPLC/MS was carried out using a Waters Acquity UHPLC (Waters, Milford, Mass.) coupled to an LTQ mass spectrometer (Thermo Fisher Scientific, Waltham, Mass.) equipped with an electrospray ionization source. Two separate UHPLC/MS injections were performed on each sample: one optimized for positive ions and one for negative ions. Derivatized samples for GC/MS were analyzed on a Thermo-Finnigan Trace DSQ fast-scanning single-quadrupole MS operated at unit mass resolving power. Chromatographic separation followed by full-scan mass spectra was carried out to record retention time, molecular weight (m/z), and MS/MS of all detectable ions presented in the samples.

Metabolite Identification:

Metabolites were identified by automated comparison of the ion features in the experimental samples to a reference library of chemical standard entries that included retention time, molecular weight (m/z), preferred adducts, and in-source fragments as well as their associated MS/MS spectra. This library allowed the rapid identification of metabolites in the experimental samples with high confidence.

Data Imputation and Statistical Analysis:

The samples were analyzed over the course of 2 days. After the data were corrected for minor variations resulting from instrument interday tuning differences, the missing values for a given metabolite were imputed with the observed minimum detection value on the assumption that they were below the limits of detection. For the convenience of data visualization, the raw area counts for each biochemical were rescaled by dividing each sample value by the median value for the specific biochemical. Statistical analysis of the data was performed using JMP (SAS, Cary, N.C.), a commercial software package, and "R", which is a freely available open-source software package. A log transform was applied to the observed relative concentrations for each biochemical because, in general, the variance increased as a function of a biochemical's average response. Welch t tests were performed to compare data obtained from experimental groups. Multiple comparisons were accounted for with the false discovery rate method, and each false discovery rate was estimated using q values. Random forest (RF) analysis was performed on untransformed data using R. Random forest is a supervised classification technique based on an ensemble of decision trees. For a given decision tree, a subset of samples is selected to build the tree; and then the remaining samples are predicted from this tree. This process is repeated thousands of times to produce a forest. The final classification is determined by computing the frequencies ("votes") of predictions for each group over the whole forest. This method is unbiased because the prediction for each sample is based on trees built from a subset of samples not including it; thus, the prediction accuracy is an unbiased estimate of predicting a new data set. To see which variables contribute the most to the separation, an "importance" measure is computed. We used the "mean decrease accuracy" as this metric. This value is determined by randomly permuting a variable and then running the values through the trees and reassessing the prediction accuracy. If a variable is not important, then this procedure will have little change in the accuracy (permuting random noise will give random noise), whereas if a variable is important, the accuracy will drop after such a permutation.

Metabolomic Analysis Results

Using LC/MS and GC/MS analysis, 437 distinct metabolites were identified in the plasma sample. Of these, 228 biochemicals matched a named structure in the reference library. The remaining 209 biochemicals represent distinct chemical entities, but they do not match a named biochemical in the reference library. The changes in the metabolites between the experimental groups were calculated by the ratio of their group means. The statistical significance of the changes was analyzed by Welch t test, with $P<0.05$ deemed to be significant. Some of the results are described below.

Bile Acids

Figure 8:
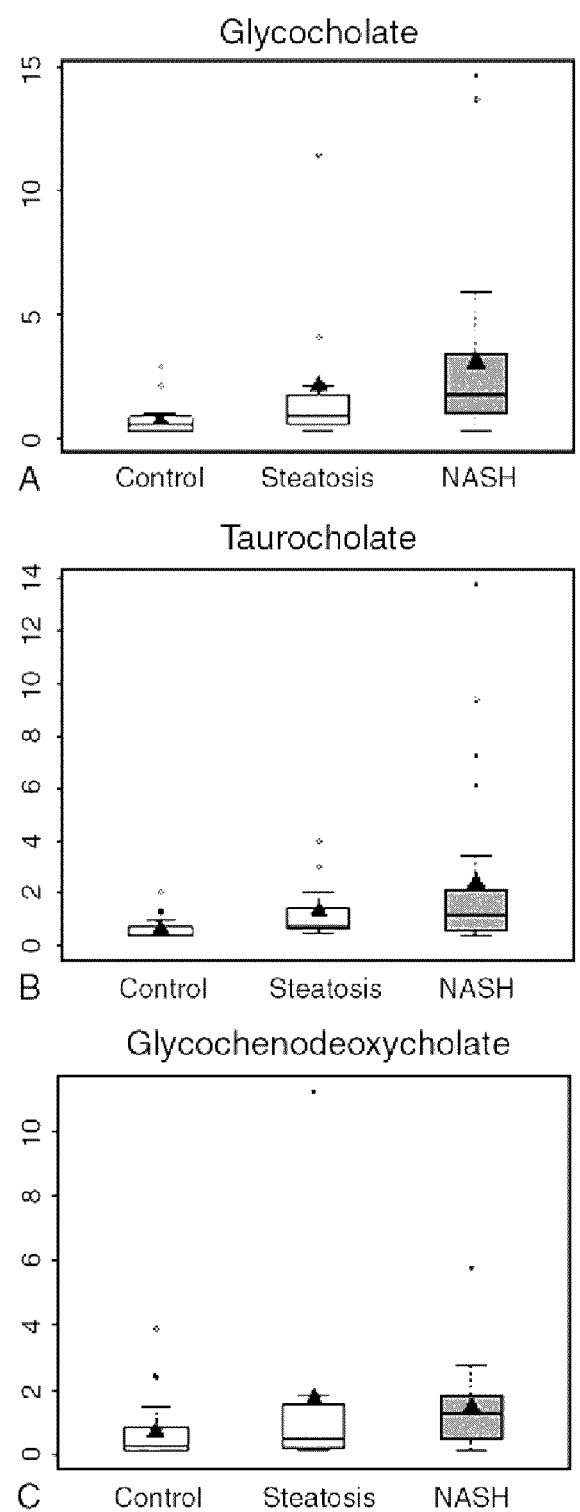
FIG. 8 (A-C) provides box plots of plasma levels of bile salts in healthy controls and subjects with steatosis and NASH as described in Example 6. Median scaled values are presented on the y-axis. Only bile salts that were significantly different ($P<0.05$) between controls and NASH are shown.

As shown in FIG. 8, there was a 4-fold increase in the plasma concentration of glycocholate and taurocholate and a 2-fold increase in glycochenodeoxycholate in subjects with NASH as compared with controls. These bile acids were also higher in the steatosis group compared with controls; however, only taurocholate met the statistical significance cutoff of $P<0.05$.

Table 15 provides additional statistical data for the bile acids (from the bile acid metabolism subpathway). The P values for the listed biomarkers were all <0.1.

TABLE 15

Bile acid biomarkers

| | | | % Change | | |
| --- | --- | --- | --- | --- | --- |
| Name | Kegg | HMDB | (NASH)/ (CONTROL) | (STEATOSIS)/ (CONTROL) | (STEATOSIS)/ (NASH) |
| cholate | C00695, C04661, C01558 | HMDB00619 | 125% | 42% | −37% |
| glycocholate | C01921 | HMDB00138 | 331% | 205% | −29% |
| taurocholate | C05122 | | 303% | 115% | −47% |
| taurochenodeoxy-cholate | C05465 | HMDB00951 | 24% | 85% | 48% |
| taurodeoxycholate | C05463 | HMDB00896 | 115% | 11% | −48% |
| glycodeoxycholate | C05464 | HMDB00631 | 247% | 23% | −65% |
| glycochenodeoxy-cholate | C05466, C05462 | HMDB00708, HMDB00637 | 103% | 144% | 21% |

Glutathione Metabolism

Figure 9:
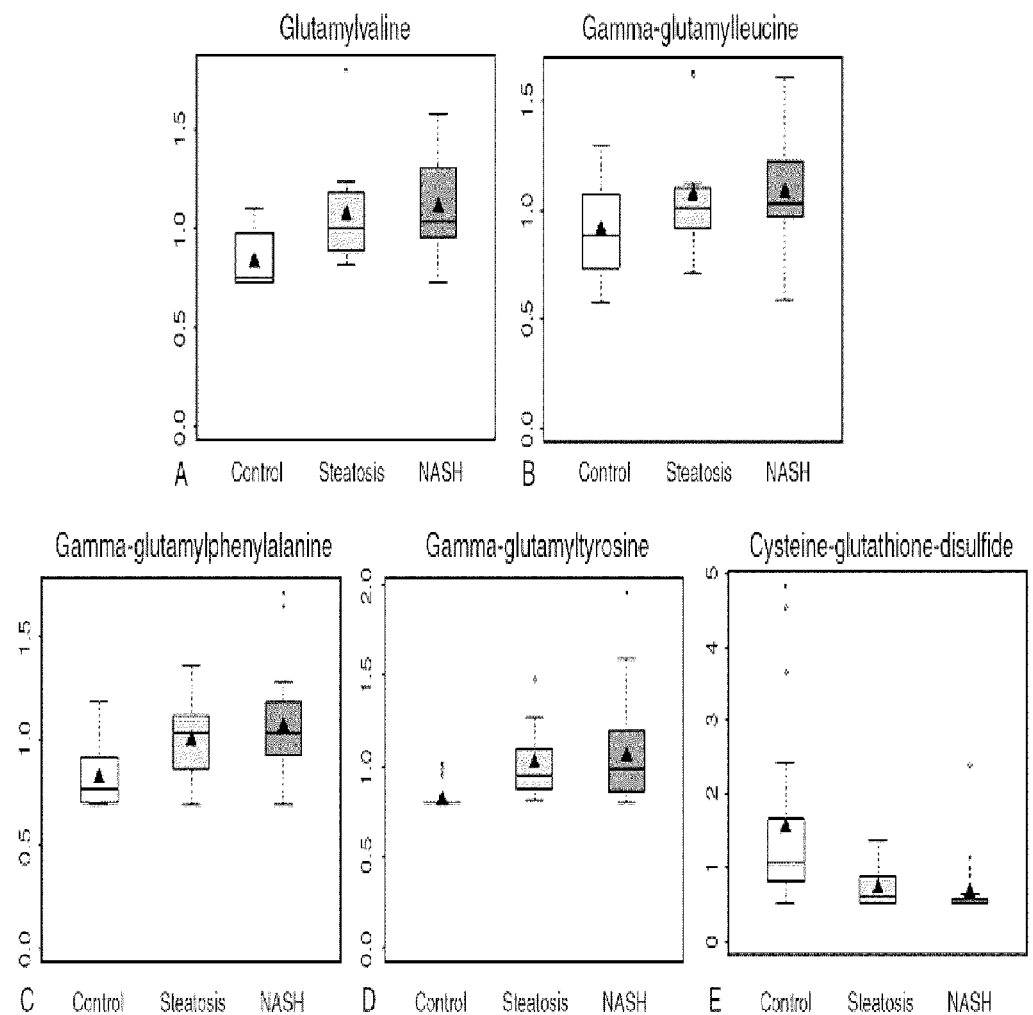
FIG. 9 (A-E) provides box plots of plasma levels of glutamyl amino acids in healthy controls and subjects with steatosis and NASH as described in Example 6. All are significantly different ($P<0.05$) in NASH and steatosis compared with controls except γ-glutamylleucine, which is significantly higher in NASH only. Glutathione metabolism is up-regulated in subjects with NAFLD.

Consistent with decreased plasma glutathione in subjects with steatosis and NASH (Table 16), the concentration of cysteine-glutathione disulfide, a product of glutathione and cysteine conjugate, was significantly lower in subjects with steatosis and NASH (FIG. 9E). In addition, several glutamyl dipeptides—glutamyl valine, glutamyl leucine, glutamyl phenylalanine, and glutamyl tyrosine—were higher in both NASH and steatosis. The increase was of similar magnitude in both groups.

In Table 16, the rows represent the actual groups and the columns list the predicted groupings by metabolomic analysis.

TABLE 16

Confusion matrix of sample by RF analysis

|  | Healthy | NASH | Steatosis | Class error |
|---|---|---|---|---|
| Healthy | 23 | 0 | 2 | 0.08 |
| NASH | 2 | 11 | 11 | 0.54 |
| Steatosis | 1 | 6 | 4 | 0.64 |

Lipids

Figure 10:
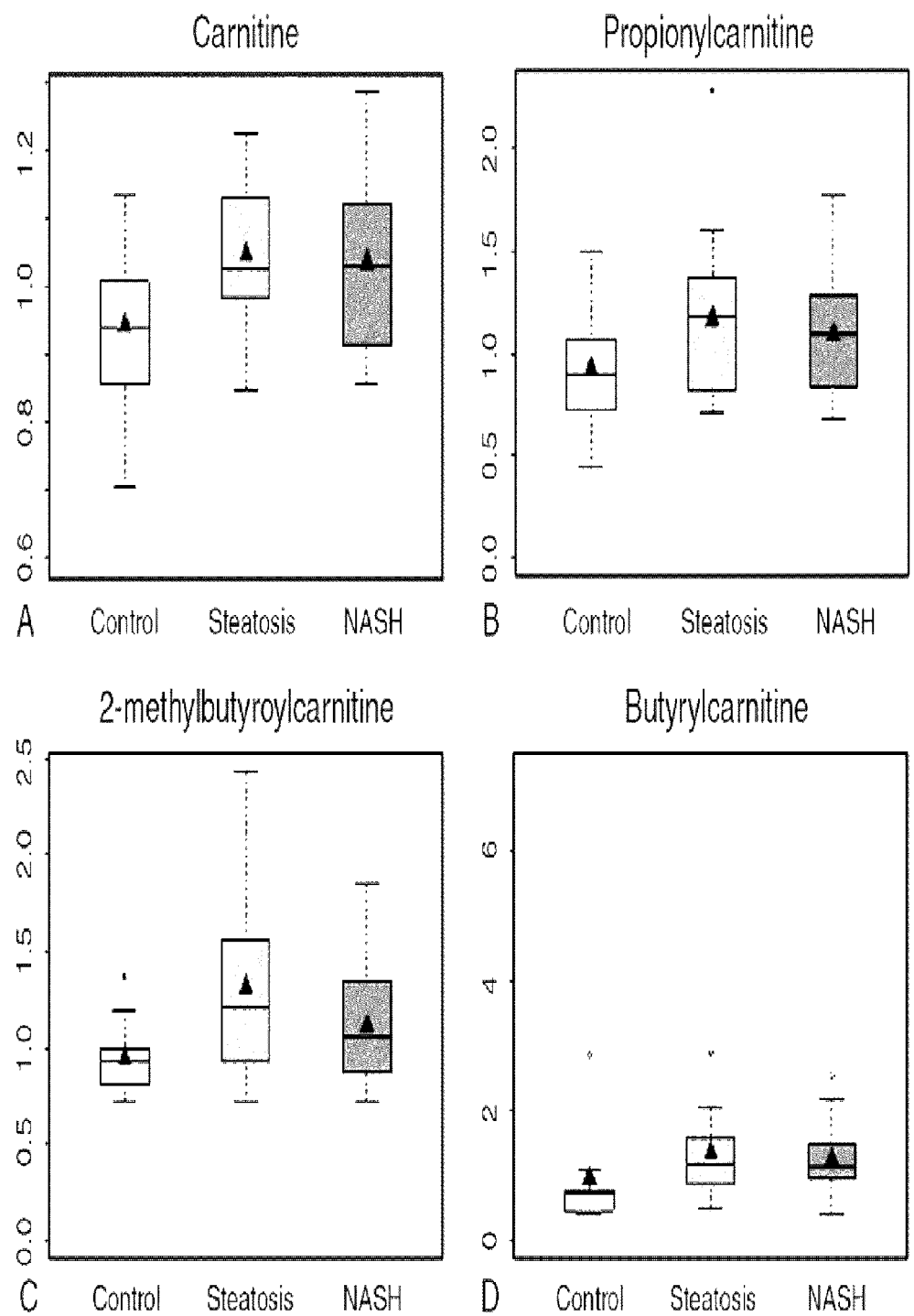
FIG. 10 (A-D) provides box plots of plasma concentration of carnitine and acylcarnitines in subjects with NAFLD and healthy controls as described in Example 6.

Subtle differences in lipid profiles were found between subjects with NAFLD and the healthy controls. Several free fatty acids—eicosapentaenoate (C20:5n3), docosahexaenoate (C22:6n3), 10-undecenoate (C11:1n1), and arachidonate (C20:4n6)—were significantly lower in individuals with NASH as compared with controls. In contrast, only caprate (C10:0) and 10-undecenoate (C11:1n1) were significantly lower in subjects with steatosis as compared with controls. Only linolenate (C18:3n3 or 6) and undecanoate (C11:0) were significantly higher in subjects with steatosis when compared with those with NASH. There were no other differences in the fatty acids profile among steatosis and NASH subjects. Metabolomic analysis could quantify 14 species of carnitine in the plasma. Free carnitine and butyrylcarnitine levels were significantly elevated in both steatosis and NASH compared with controls (FIG. 10A, E). In addition, propionylcarnitine and 2-methylbutyrylcarnitine levels were significantly higher in subjects with NASH only. Significant differences in the levels of lysophosphocholines were observed between individuals with NASH and controls. Specifically, the concentration of glycerophosphocholine, 1-oleoylglycerophosphocholine, 1-linoleoylglycerophosphocholine, and 1-arachidonoylglycerophosphocholine were significantly lower in NASH when compared with controls. Only 1-oleoylglycerophosphocholine was significantly lower in subjects with steatosis.

Carbohydrates

Glucose and pyruvate were significantly higher in subjects with NASH. Mannose and lactate levels were higher in both steatosis and NASH. In addition, erythronate levels were higher in subjects.

Amino Acids

Figure 11:
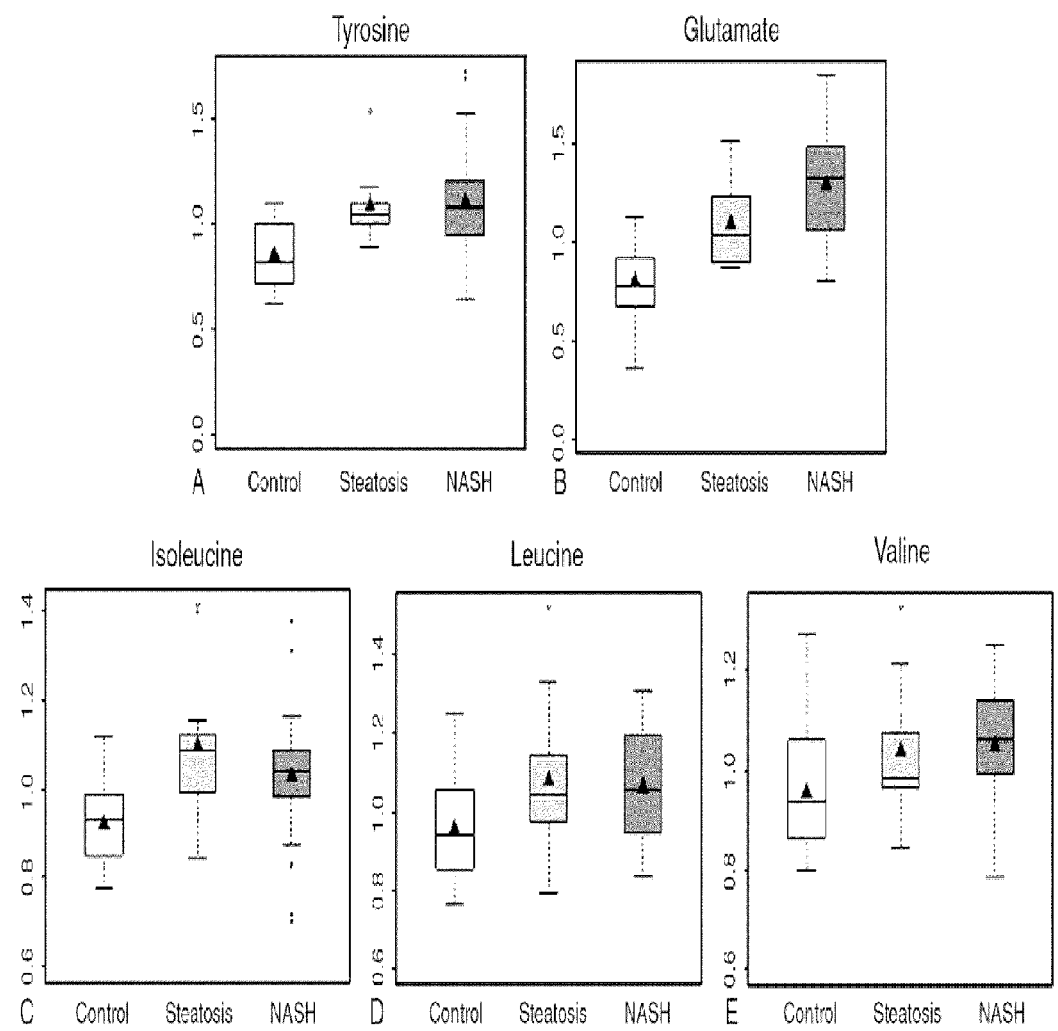
FIG. 11 (A-E) provides box plots of plasma concentration of branched-chain amino acids, tyrosine, and glutamate in healthy controls and subjects with steatosis and NASH as described in Example 6. For NASH vs controls, $P<0.05$ for all. For steatosis vs controls, $P<0.05$ for glutamate, tyrosine, and isoleucine.

Among the essential amino acids, phenylalanine, and branched-chain amino acids, leucine, isoleucine, and valine were higher in subjects with NASH as compared with controls (FIG. 11). Glutamate, aspartate, and tyrosine were also elevated in individuals with NASH. In contrast to subjects with NASH, only glutamate, lysine, tyrosine, and isoleucine were significantly higher in subjects with steatosis compared with controls. There were no significant differences in amino acid levels among subjects with steatosis and NASH.

Others

A number of unnamed biochemicals in the plasma were significantly higher in NAFLD subjects, in particular Metabolite-11546 and Metabolite-11529, which were almost 3-fold higher in NASH compared with controls.

NASH Vs. Steatosis

Plasma levels of very few metabolites were significantly different in subjects with steatosis and NASH. These include glutamate, creatine, pyruvate, and unknown Metabolite-01911_200, which were significantly lower, and undecenoate (C11:0) and linolenate (α or γ), which were significantly higher in subjects with steatosis when compared with those with NASH.

RF Analysis

Figure 12:
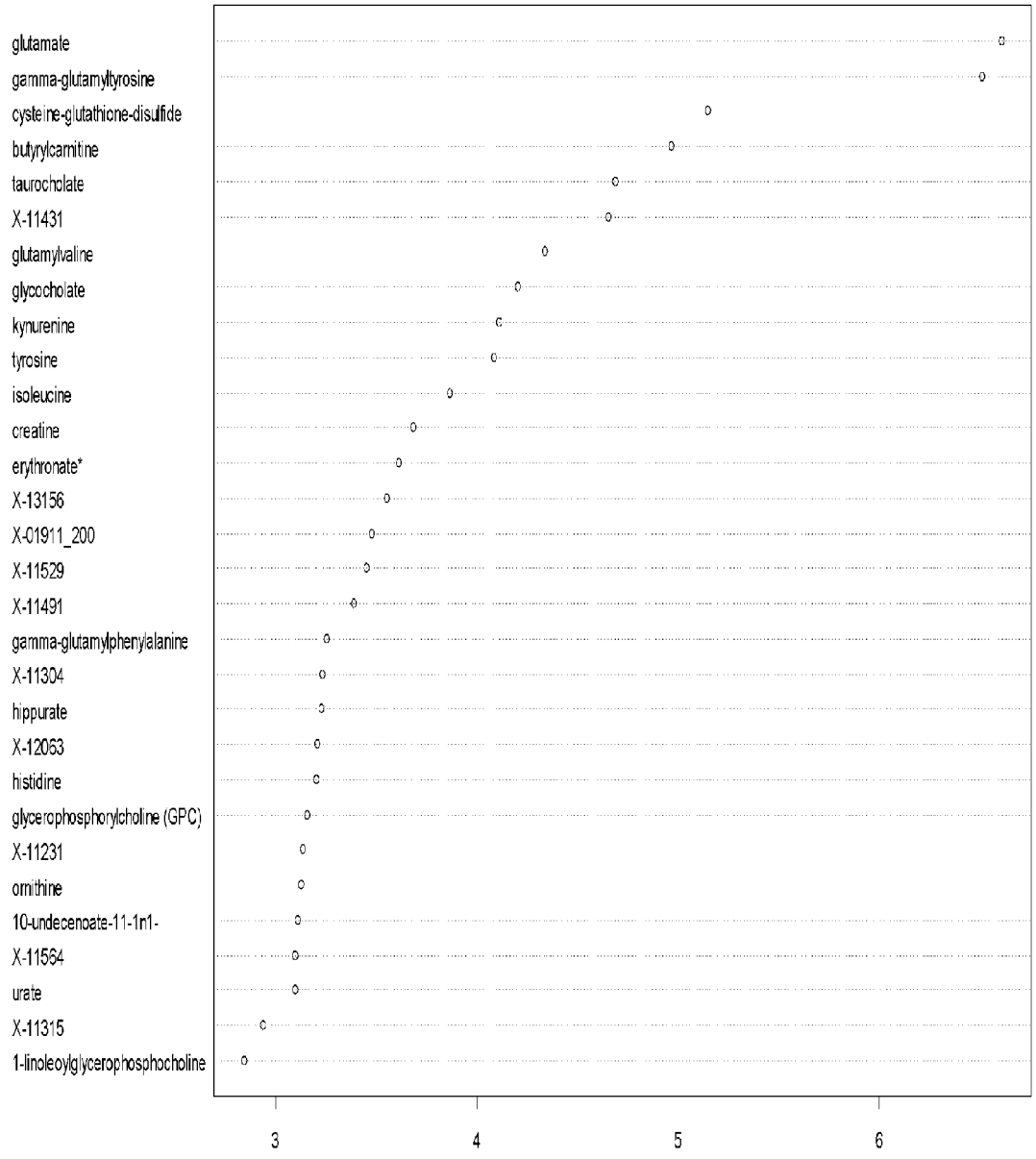
FIG. 12 illustrates a random forest importance plot for all subjects as described in Example 6.

An RF analysis of the plasma biochemical profile data was performed to test the ability of the metabolomic data to correctly classify the samples into their respective groups (Table 16). For the healthy group, 92% of the subjects (23 of 25) could be correctly separated from the individuals with NAFLD (steatosis and steatohepatitis), with a class error of 0.08. Among the NAFLD subjects, the error rate was high for subjects in the NASH and steatosis groups, suggesting that the metabolic profile of the NASH and steatosis group was not distinguishable based on this data set. The metabolites that most effectively separated the groups are shown in the importance plot (FIG. 12). Because the steatosis group was small (not powered enough), we also performed an RF analysis between subjects with NASH only and healthy controls. Twenty-three of 24 subjects with NASH could be separated from healthy controls, with an error rate of 4.1%. The metabolites that most effectively separated the group are shown in the importance plot (FIG. 13).

RF and Principal Component Analysis

To assess the ability to classify subjects as healthy, with steatosis, or with NASH, RF analysis was performed using the entirety of the metabolomic data. An excellent separation of the healthy subjects and NAFLD subjects was achieved. However, the steatosis and NASH subjects were not readily distinguishable (Table 16). This is consistent with the result from Welch t test. Many metabolites were deemed to be statistically significant when either the steatosis group or the NASH group was compared with the healthy control group. Only a few metabolites were significantly different between the steatosis and the NASH groups. It is worth noting that the number of subjects in the steatosis group was rather limited (n=11), and the statistical significance is impacted by the group size. As shown in FIG. 13, a panel of markers that provided the most contribution to the separation of the healthy group and NASH group was discovered. Not surprisingly, these markers matched with the metabolites identified by the Welch t tests (e.g., glutathione metabolites, bile acids, amino acids, etc.)

While the invention has been described in detail and with reference to specific embodiments thereof, it will be apparent to one skilled in the art that various changes and modifications can be made without departing from the spirit and scope of the invention.

What is claimed is:

1. A method of determining the presence, absence or level(s) of one or more metabolites in a sample from a subject, the method comprising
    a) extracting small molecules from a blood or blood plasma sample obtained from the subject to produce an analytical sample; and
    b) performing liquid chromatography-mass spectrometry on the analytical sample to determine a level of cysteine-glutathione disulfide and one or more additional metabolites in the sample, wherein the one or more additional metabolites are selected from the group consisting of kynurenine, glutamyl valine, gamma glutamylphenylalanine, gamma glutamylleucine, 2 amino butyrate, 3-4-5-trimethoxy-cinnamic acid, 3-carboxyl-4-methyl-5-propyl-2-furanpropanoic acid, 3-methyl-2-oxobutyrate, alpha-ketoglutarate, bradykinin, erythritol, gamma tocopherol, gluconate, glycerate, histidine, isocitrate, lysine, mannose, N-acetylglycine, nicotinamide, phenylacetate, p-hydroxyphenyllactate, pyruvate, quinate, serine, threonate, threonine, thyroxine, trans-4-hydroxyproline, urate, uridine, urocanate, xanthine, and combinations thereof.

2. A method of determining the presence, absence or level(s) of one or more metabolites in a sample from a subject, the method comprising
   a) extracting small molecules from a blood or blood plasma sample obtained from the subject to produce an analytical sample;
   b) performing liquid chromatography-mass spectrometry on the analytical sample to determine a level of cysteine-glutathione disulfide and one or more additional metabolites in the sample, wherein the one or more additional metabolites are selected from the group consisting of kynurenine, glutamyl valine, gamma glutamylphenylalanine, gamma glutamylleucine, 2-amino butyrate, 3-4-5-trimethoxy-cinnamic acid, 3-carboxyl-4-methyl-5-propyl-2-furanpropanoic acid, 3-methyl-2-oxobutyrate, alpha-ketoglutarate, bradykinin, erythritol, gamma tocopherol, gluconate, glycerate, histidine, isocitrate, lysine, mannose, N-acetylglycine, nicotinamide, phenylacetate, p-hydroxyphenyllactate, pyruvate, quinate, serine, threonate, threonine, thyroxine, trans-4-hydroxyproline, urate, uridine, urocanate, xanthine, and combinations thereof; and
   c) classifying the subject as either having or not having non-alcoholic steatohepatitis with at least 80% accuracy based on the level of cysteine-glutathione disulfide and the one or more additional metabolites.

\* \* \* \* \*

UNITED STATES PATENT AND TRADEMARK OFFICE
CERTIFICATE OF CORRECTION

PATENT NO.        : 9,977,034 B2                                    Page 1 of 1
APPLICATION NO.   : 14/843356
DATED             : May 22, 2018
INVENTOR(S)       : Bruce J. McCreedy et al.

It is certified that error appears in the above-identified patent and that said Letters Patent is hereby corrected as shown below:

On the Title Page

Item (73) Assignees, the name "Meabolon, Inc." should be replaced with --Metabolon, Inc.--.

Signed and Sealed this
Twenty-seventh Day of November, 2018

Andrei Iancu
*Director of the United States Patent and Trademark Office*